(12) United States Patent
Ayisi

(10) Patent No.: US 7,220,437 B2
(45) Date of Patent: May 22, 2007

(54) ANTIVIRAL AND ANTIBACTERIAL ACTIVITIES OF EXTRACTS FROM EIGHT PLANTS

(76) Inventor: Nana K. Ayisi, c/o Noguchi Memorial Institute for Medical Research, University of Ghana, Legon (GH)

( * ) Notice: Subject to any disclaimer, the term of this patent is extended or adjusted under 35 U.S.C. 154(b) by 150 days.

(21) Appl. No.: 09/978,593

(22) Filed: Oct. 18, 2001

(65) Prior Publication Data

US 2002/0182271 A1     Dec. 5, 2002

Related U.S. Application Data

(60) Division of application No. 09/319,545, filed as application No. PCT/CA97/00971 on Sep. 4, 1998, now abandoned, which is a continuation-in-part of application No. 08/762,260, filed on Dec. 9, 1996, now abandoned.

(51) Int. Cl.
    *A01N 65/00*     (2006.01)
(52) U.S. Cl. ..................................................... 424/745
(58) Field of Classification Search ................. 424/9.1, 424/9.2, 184.1, 207.1, 714; 435/5, 32
    See application file for complete search history.

(56) References Cited

OTHER PUBLICATIONS

Planchon et al. Differential effect of butyrate derivatives on human breast cancer cells grown on organotypic nodules in vitro and as xenografts in vivo, In Vivo (1992) vol. 6, pp. 605-610.*

Kerr et al. The relationship between cytotoxic drug exposure and tumor cell kill in vitro and in vivo, In Vivo (1991) vol. 5, pp. 385-388.*

Chomienne et al., Discrepancy between in vitro and in vivo passaged U-937 human leukemic Cells: Tumerorigenicity and sensitivity to differentiating drugs. In Vivo, 1988.*

Washington Times Article by Joyce Howard Price, Nov. 16, 2001, p. 3.*

Kirsi et al. Broad Spectrum antiviral cavity of 2-beta-d ribofuranosylselenzaole-carboxaimde, a new antiviral agent, Antimicrobial Agents and Chemotherapy (1983) vol. 24, No. 3, pp. 353-361.*

Mitsuya et al. Suramin protection of T Cells in vitro against infectivity and cytopathic effect of HTLV-III. Science, (1984) vol. 226, pp. 172-174.*

Sandström et al. Antiviral Therapy in AIDS: Clinical and pharmacological properties and therapeutic experience to date. Drugs (1987) vol. 34, pp. 372-390.*

El-Said An investigation into the efficacy of *Ocimum gratissimum* as used in Nigerian native medicine. Planta Medicine (1969) vol. 17, No. 2, pp. 195-200.*

The Merck Manual, Seventeenth Edition, Editor Beers et al., Published by Merck Research Laboratories, Whitehouse Station, N.J. (1999) pp. 1293-1296, 1303-1306, 1312-1323, 2320-2324 and 2341-2343).*

* cited by examiner

*Primary Examiner*—Bruce R. Campell
*Assistant Examiner*—Michelle Horning

(57) ABSTRACT

Compositions with antiviral and/or antibacterial activities comprising one or more ingredients from eight plants found in Ghana.

4 Claims, 49 Drawing Sheets

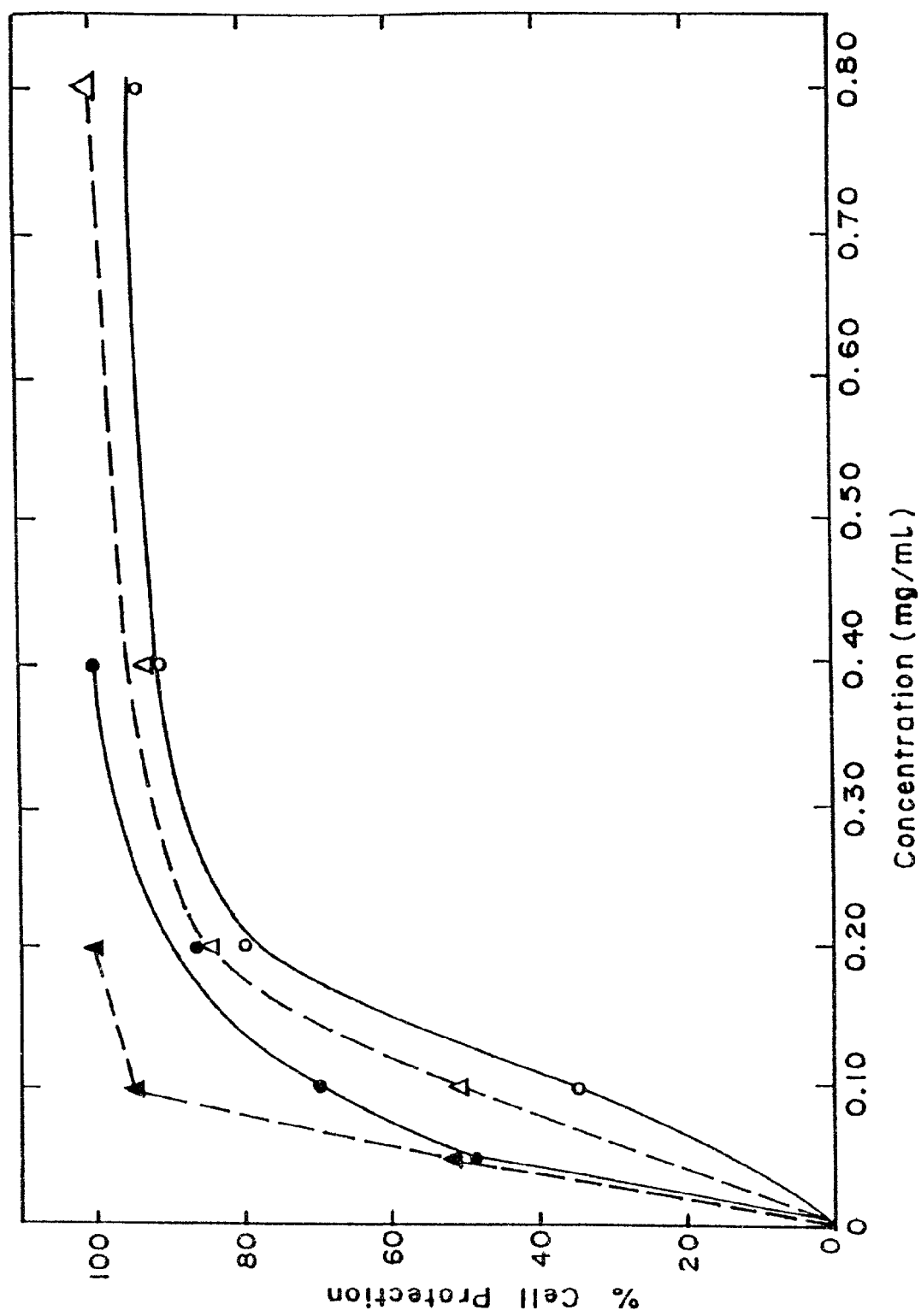

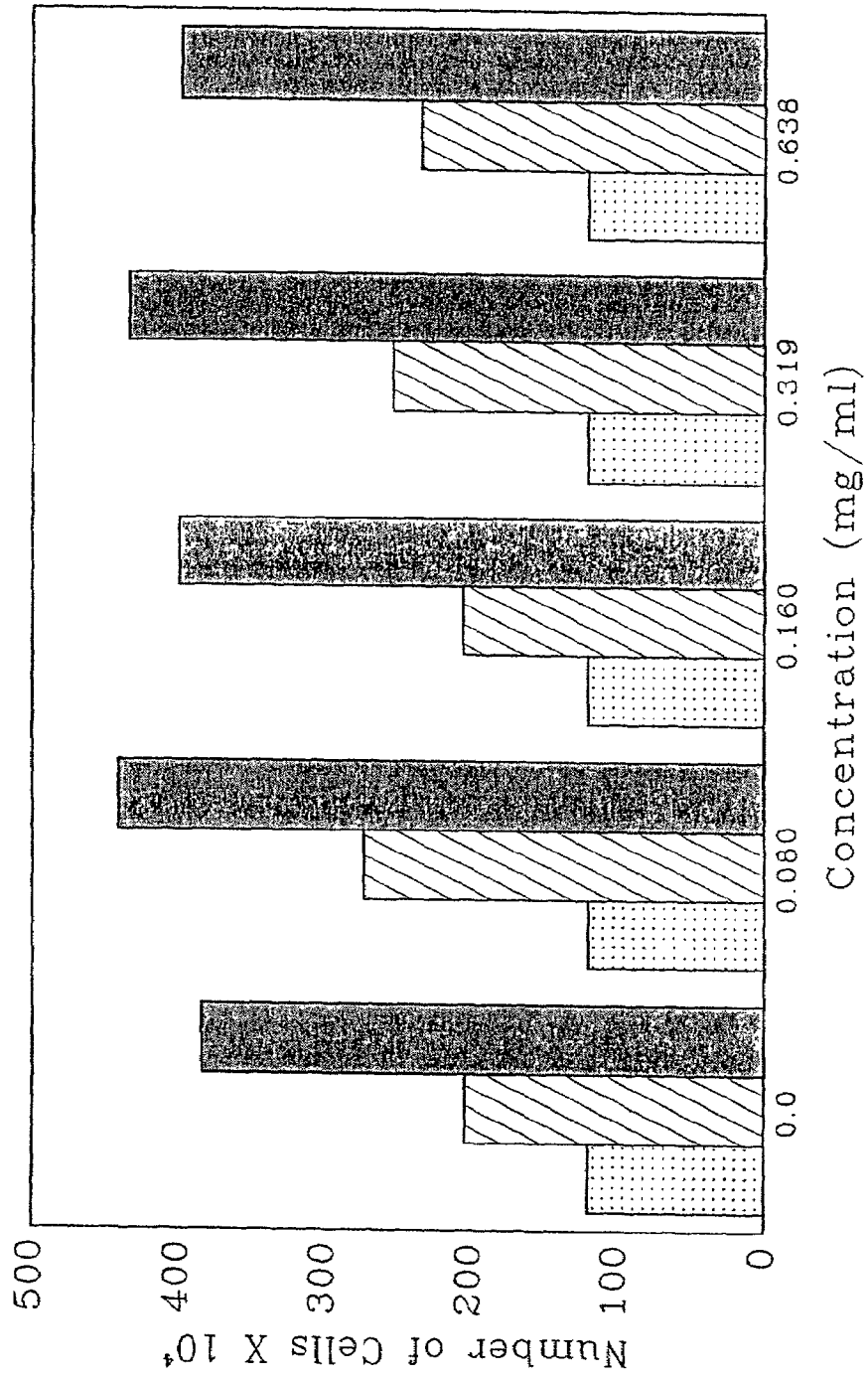

Figure 1:
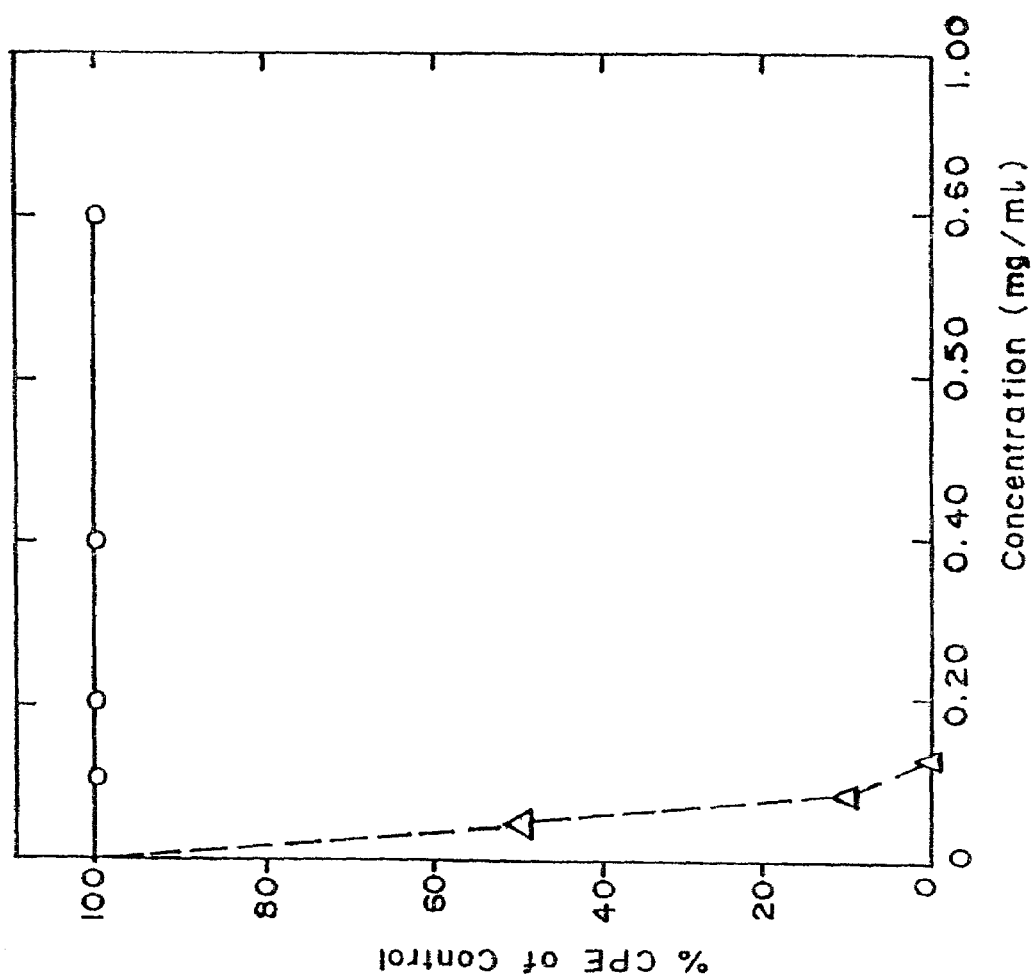
Figure 2A:
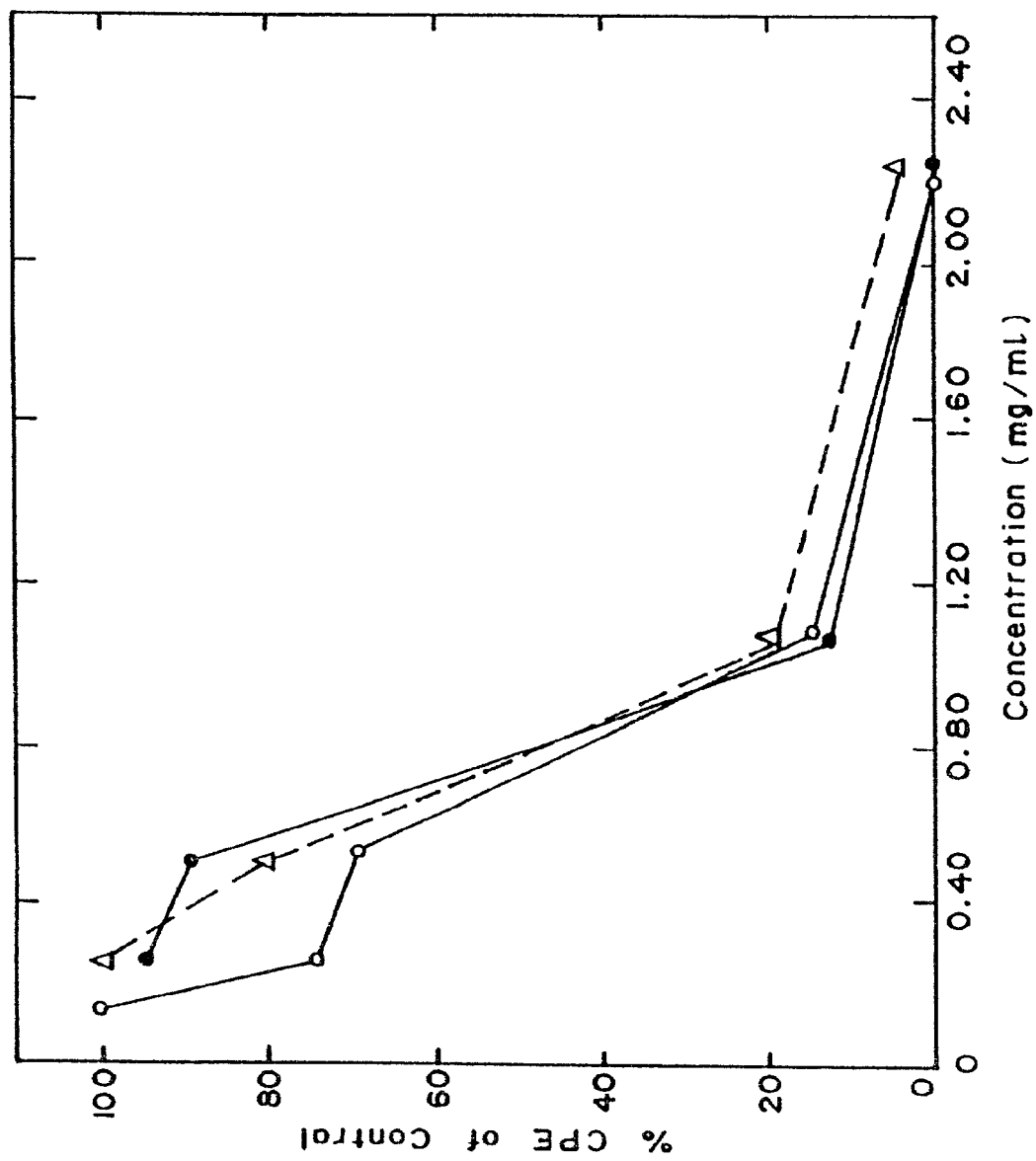
Figure 2B:
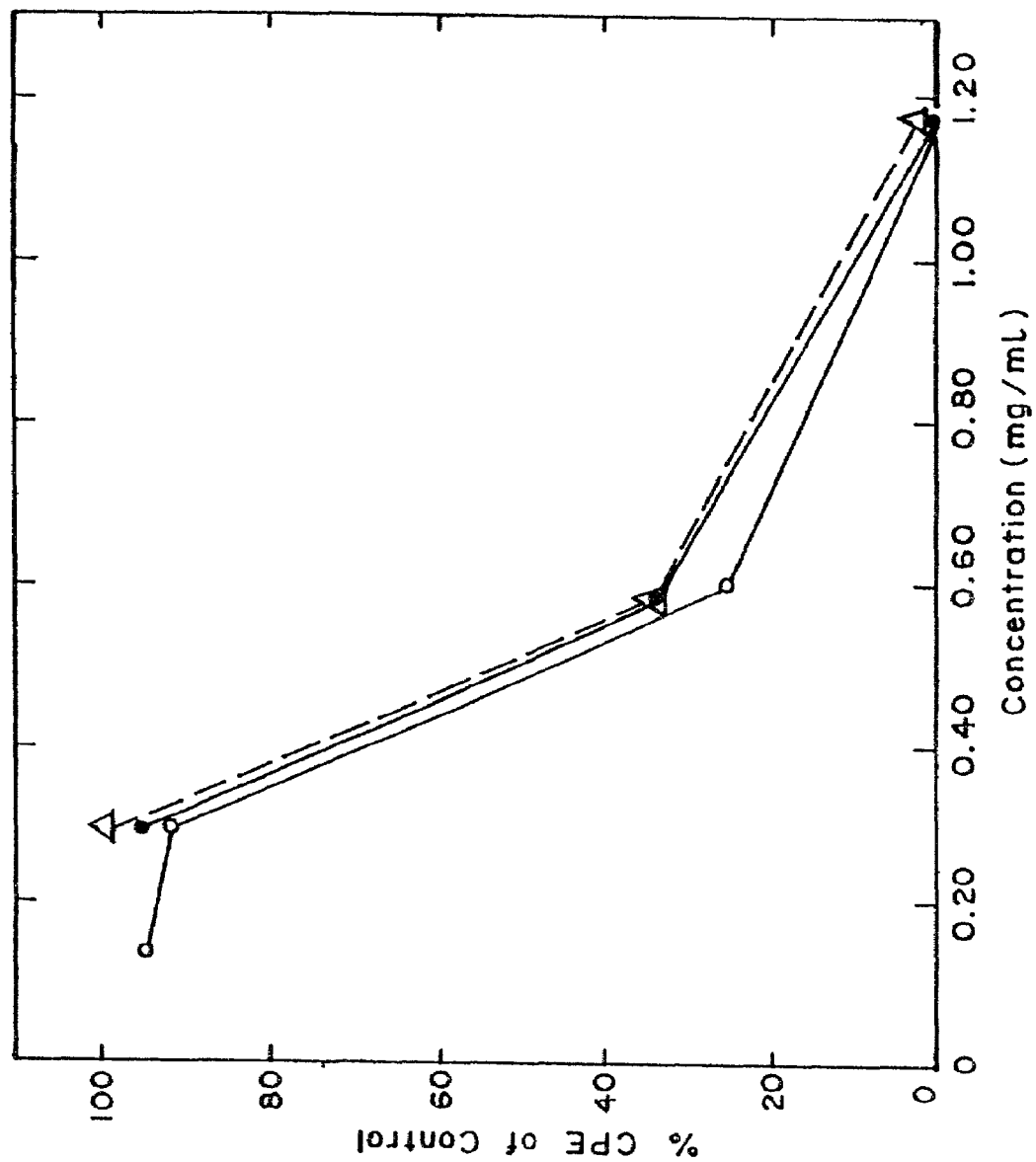
Figure 2C:
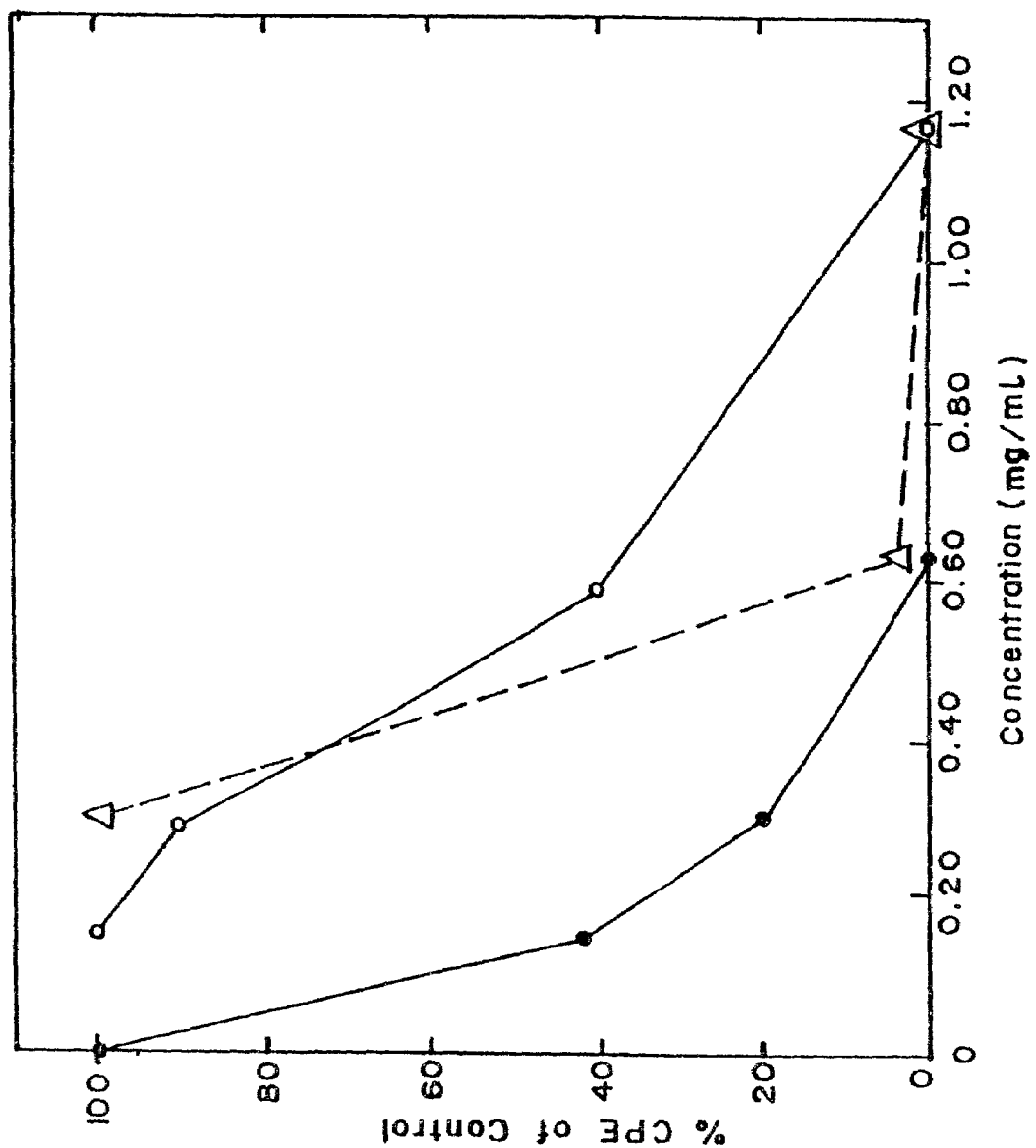
Figure 3A:
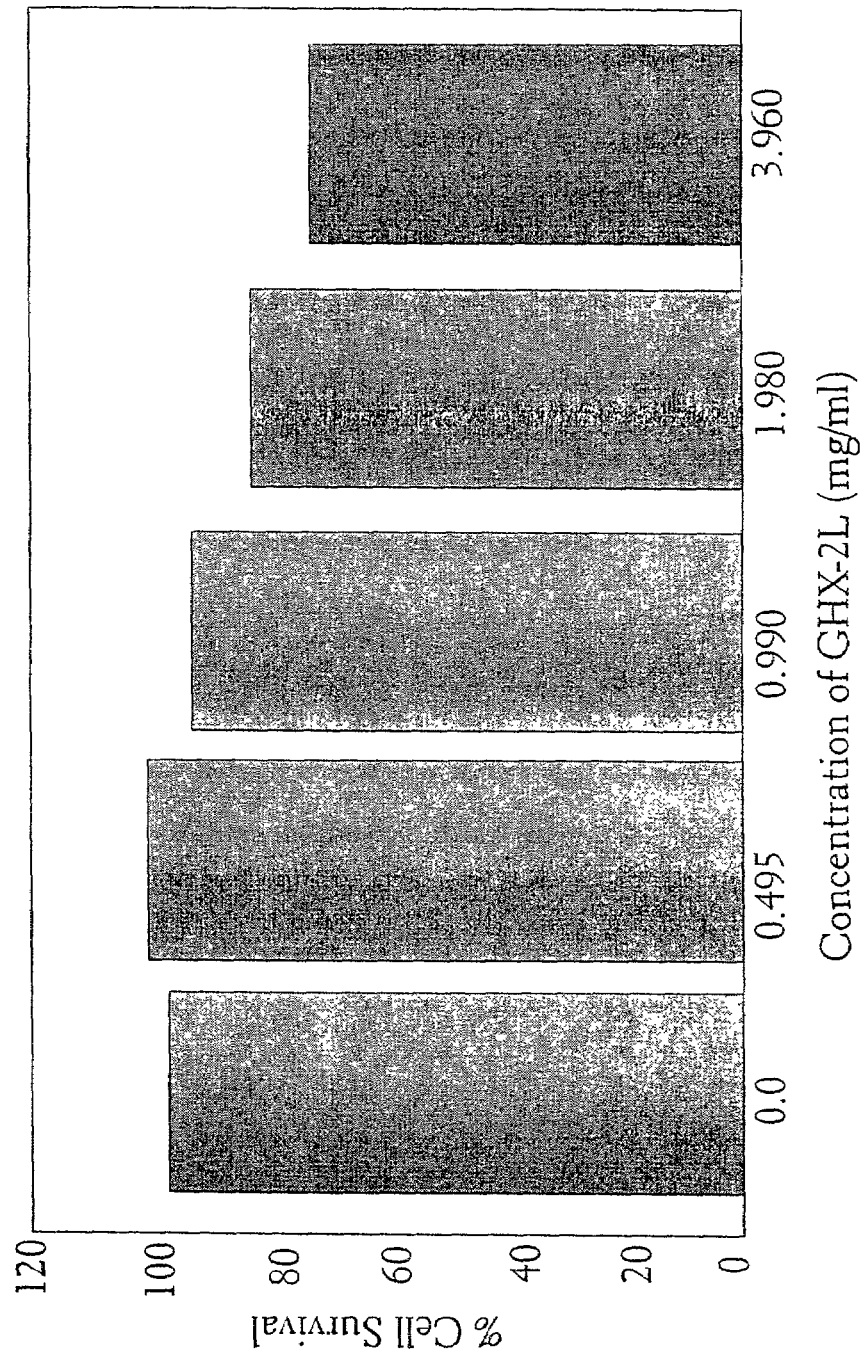
Figure 3B:
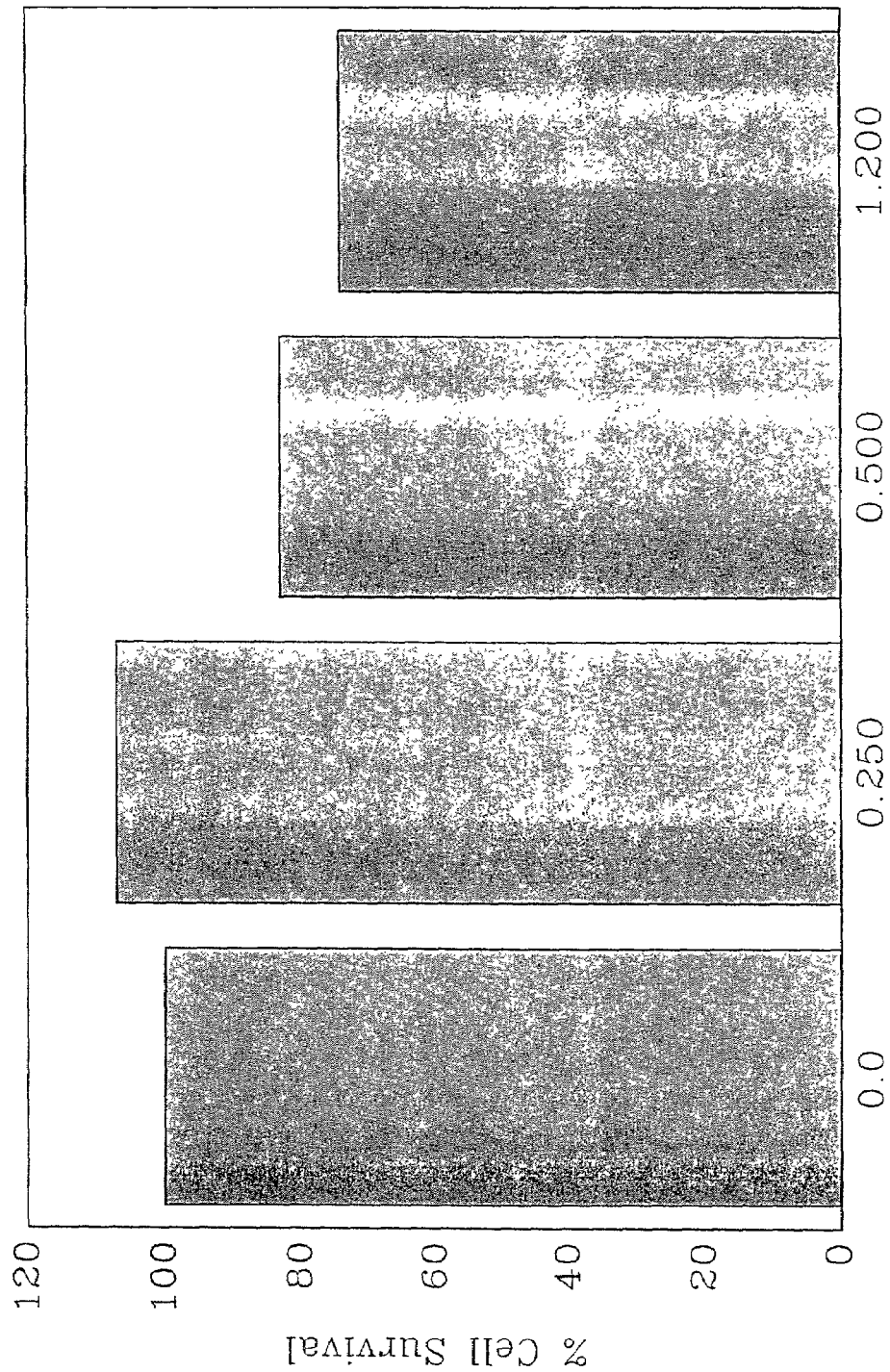
Figure 3C:
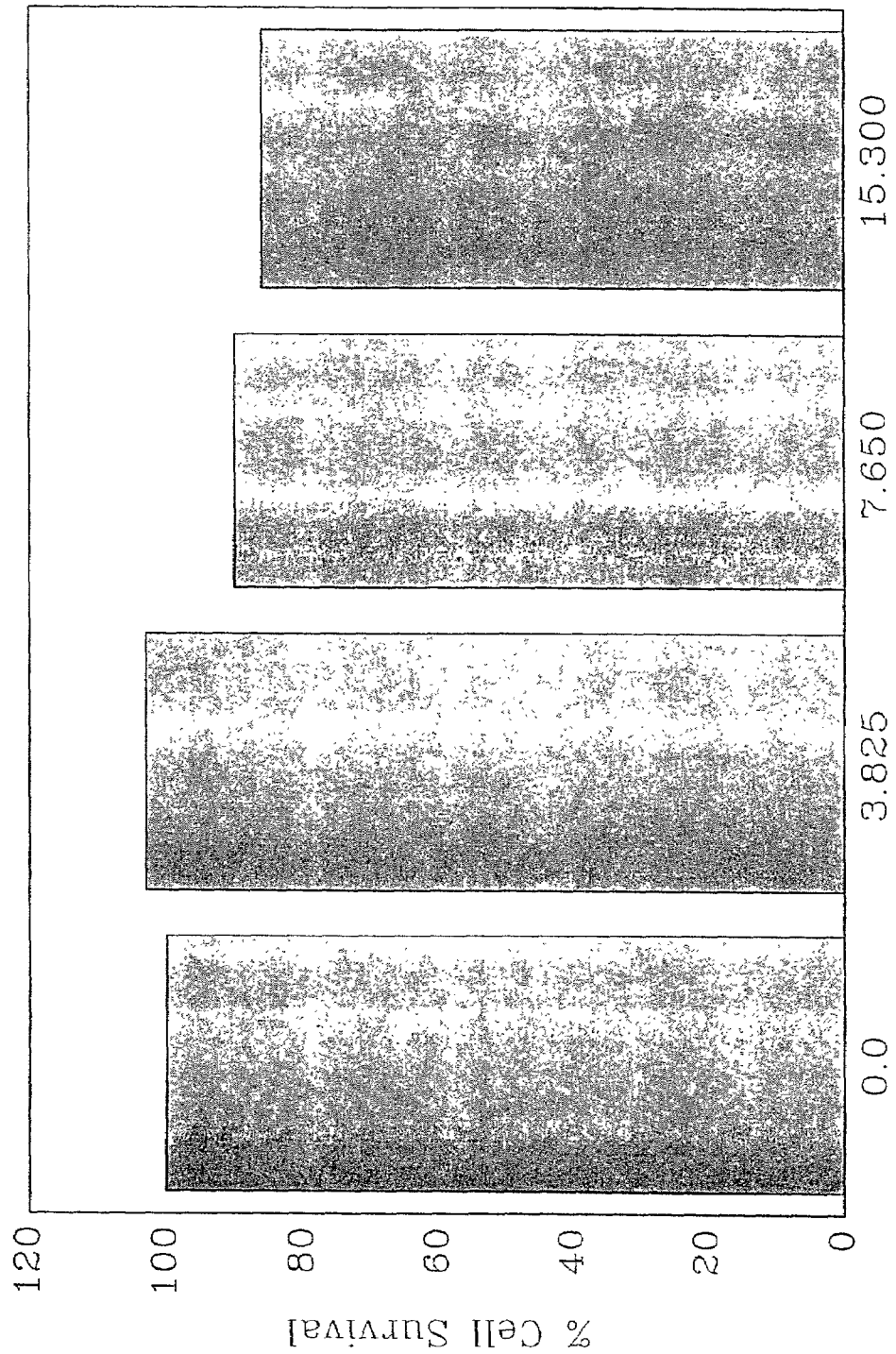
Figure 3D:
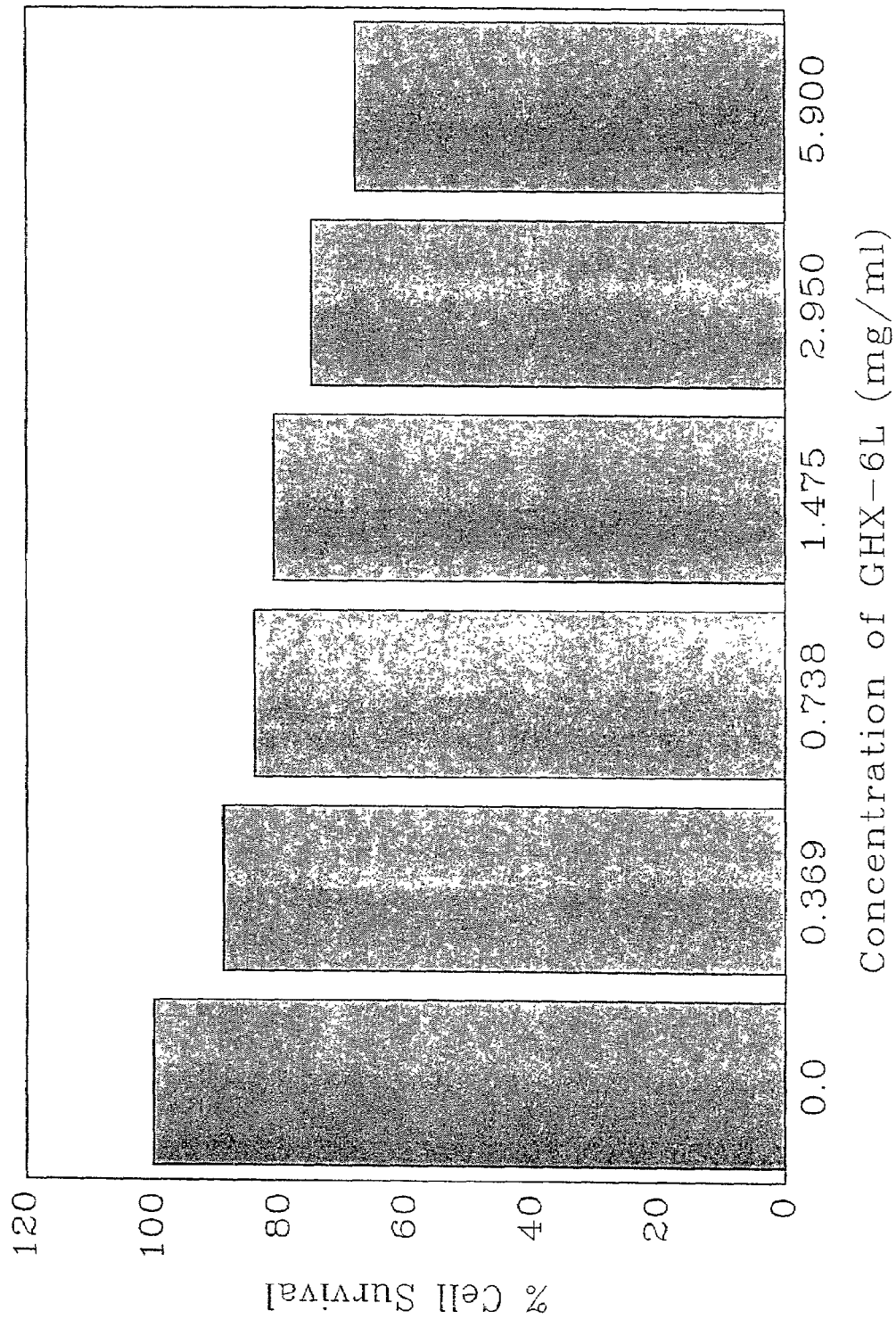
Figure 3E:
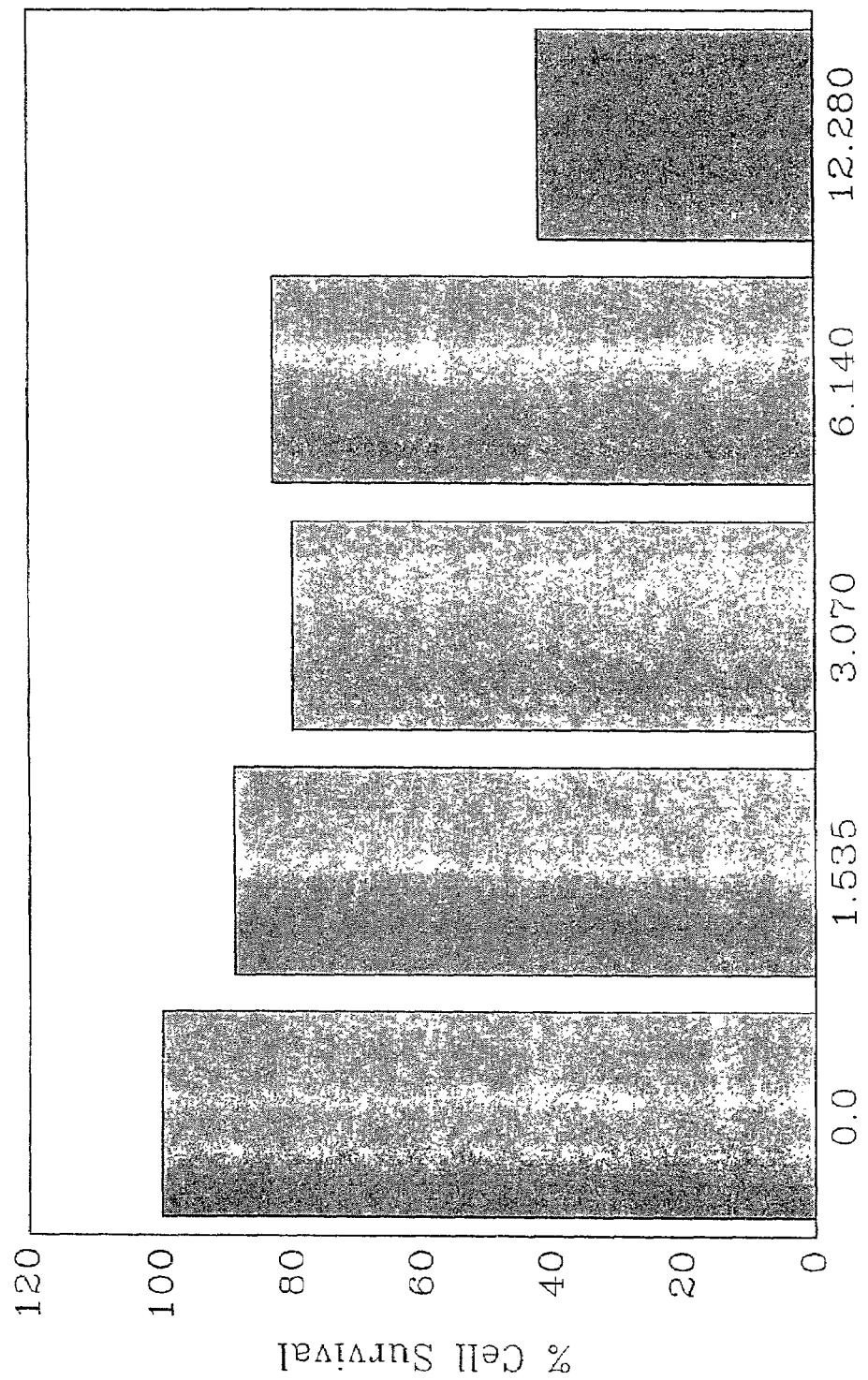
Figure 3F:
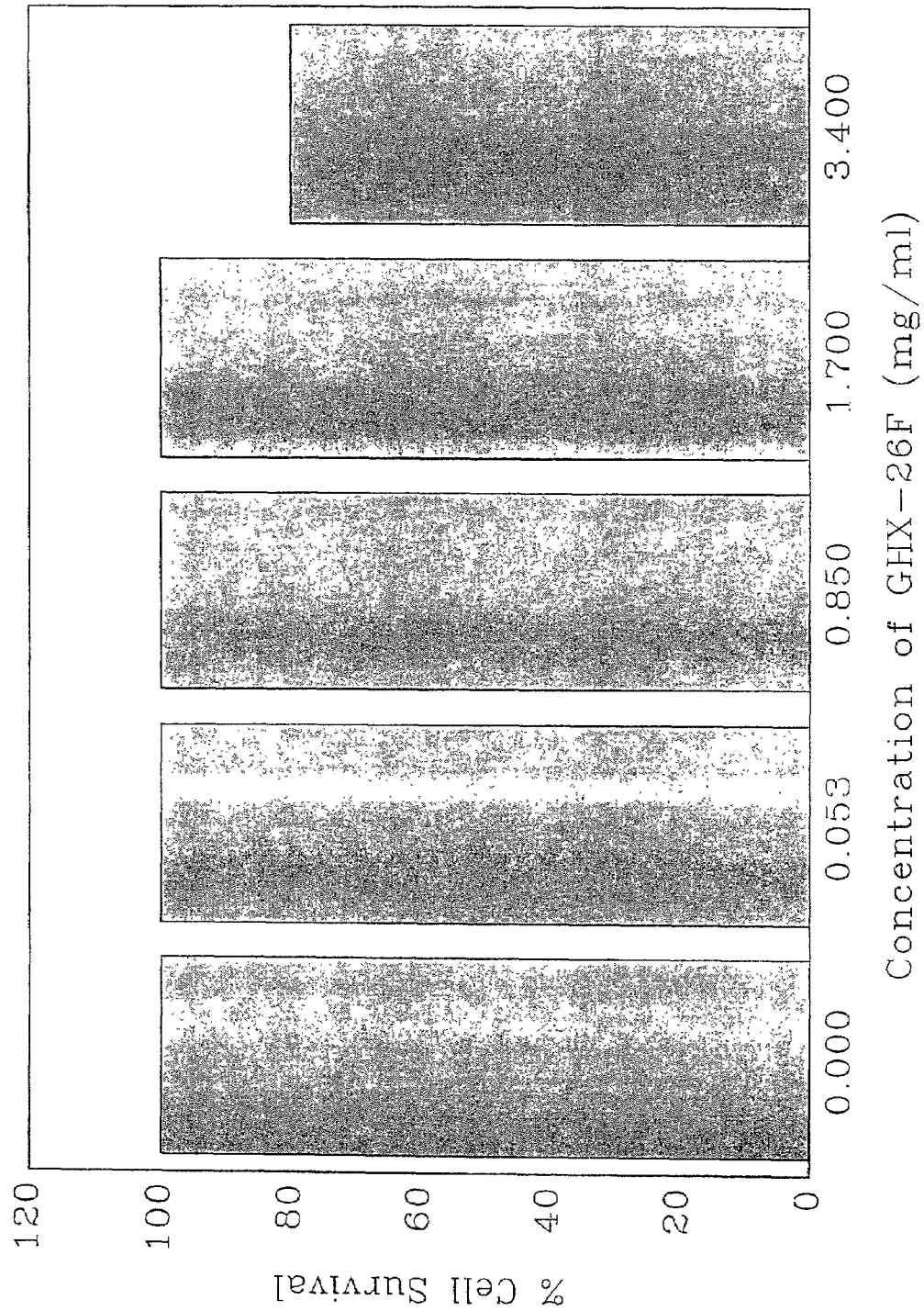

Virus production in Molt4/HIV cells: days 2(▨), and 4(▬)

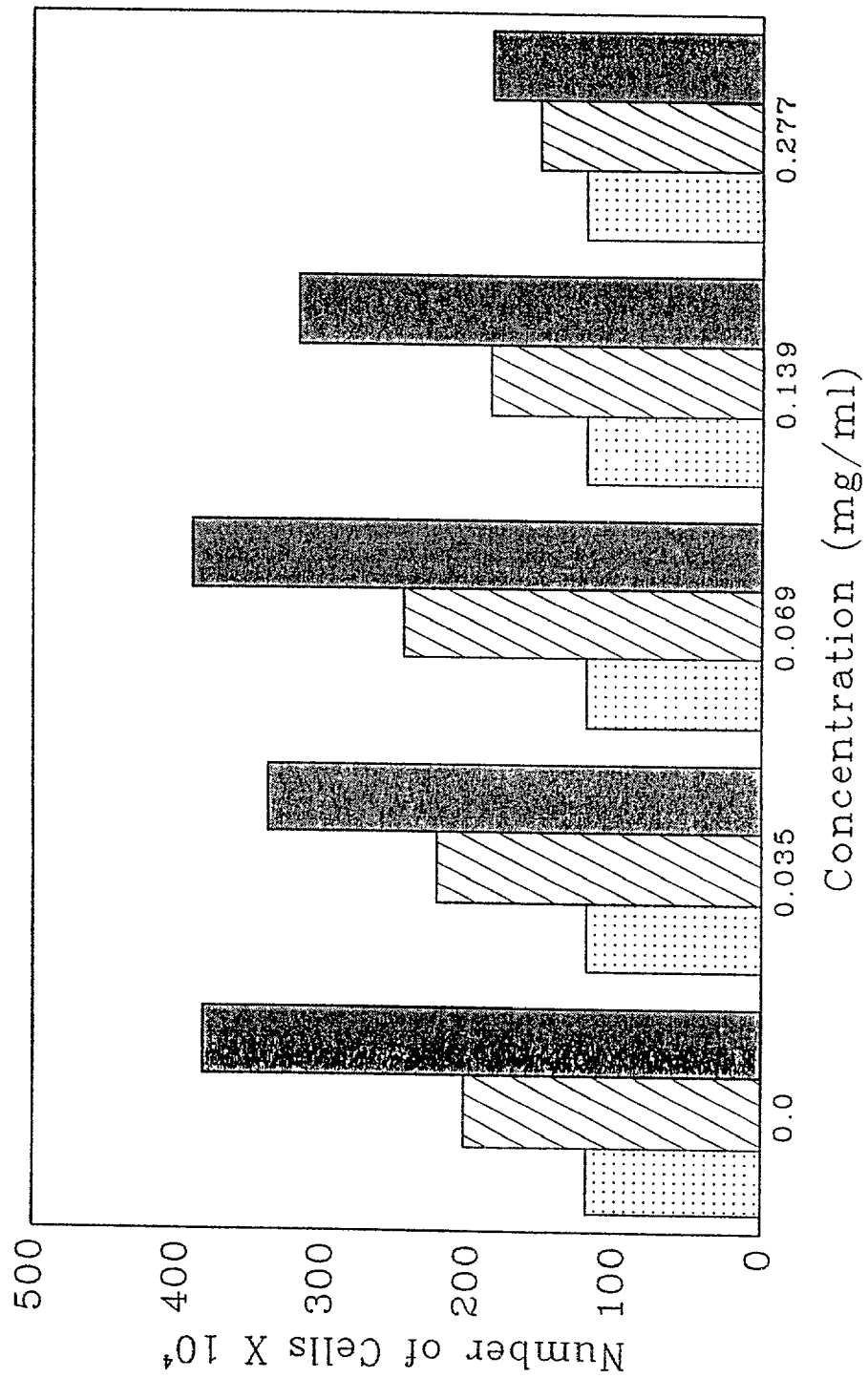

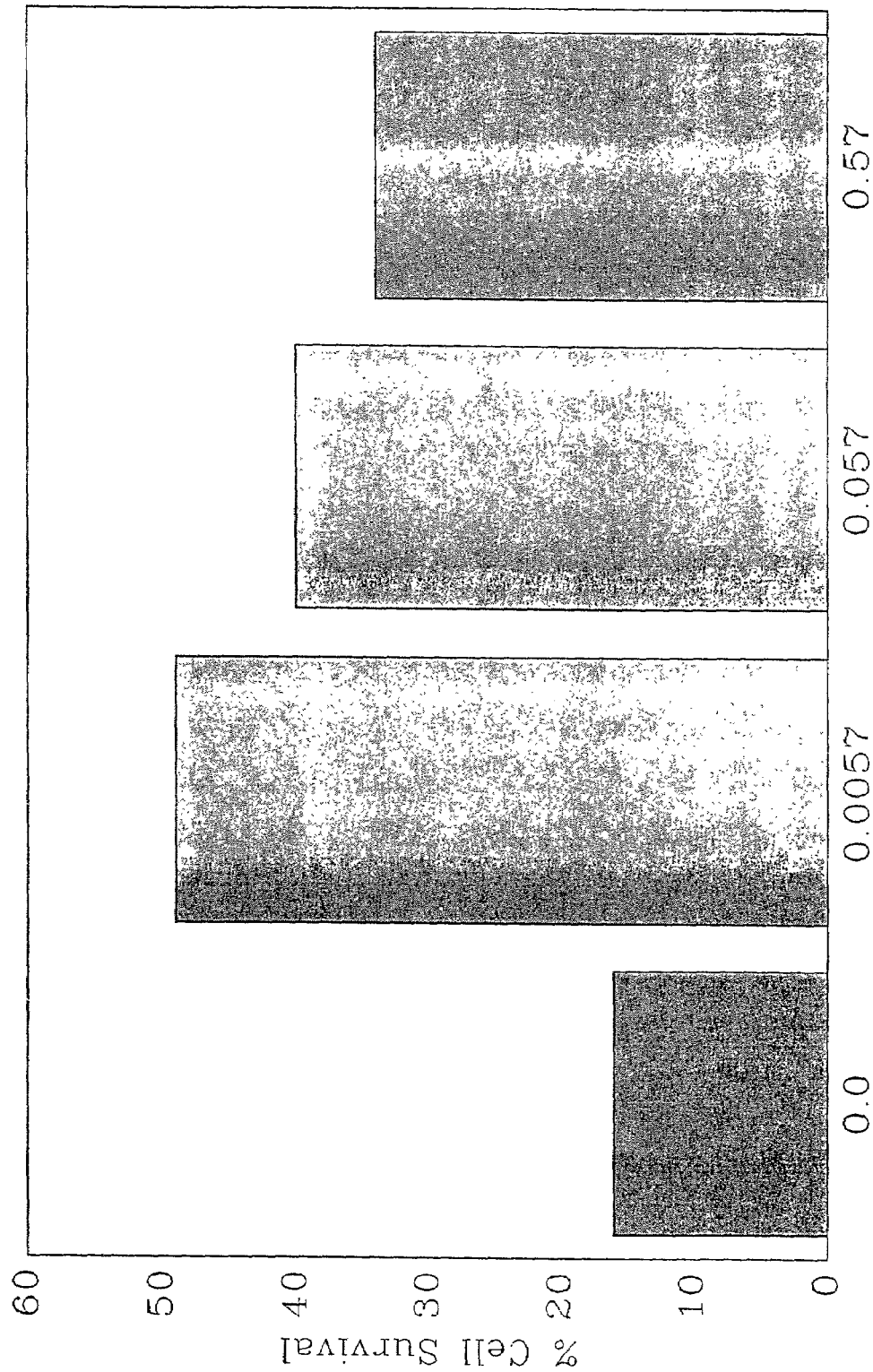

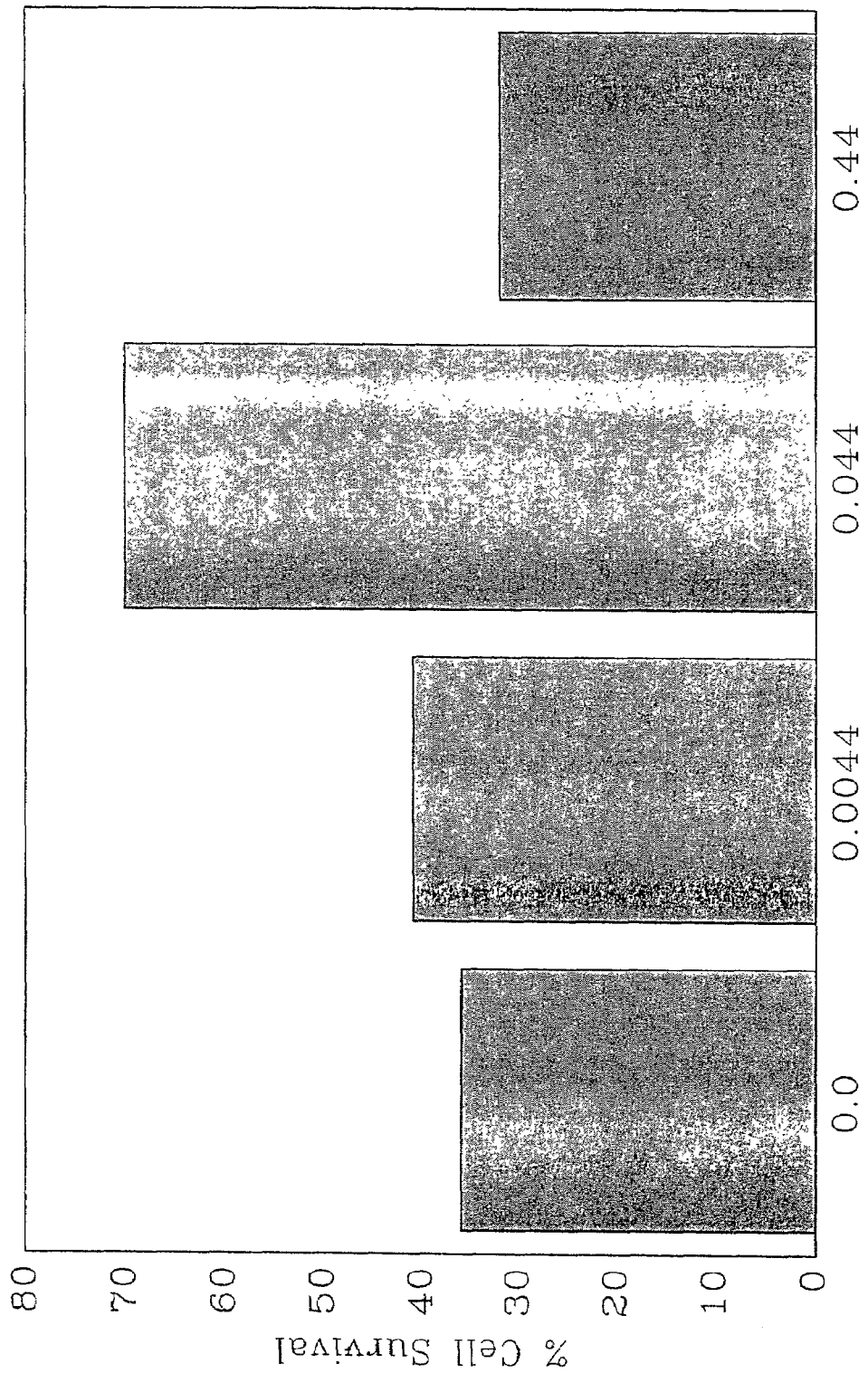

ANTIVIRAL AND ANTIBACTERIAL ACTIVITIES OF EXTRACTS FROM EIGHT PLANTS

This application is a division of U.S. Ser. No. 09/319,545 filed Jun. 9, 1999 now abandoned which is a National Phase Entry of PCT/CA97/00971, filed Sep. 4, 1998 which is a continuation in part of U.S. Ser. No. 08/762,260 filed Dec. 9,1996.

The present invention provides biologically active compositions in the fields of medicine and pharmacology. In particular, the invention relates to extracts from GHX-2, GHX-4, GHX-6, GHX-7, GHX-20, GHX-26, and GHX-27 that inhibit DNA, RNA, or both DNA and RNA viruses including the etiological agent of Acquired Immune Deficiency Syndrome (AIDS) as well as opportunistic viral infections seen in AIDS. The invention further relates to extracts from GHX-2, GHX-8, GHX-20, GHX-26, and GHX-27 that inhibit bacteria.

The acquired immune deficiency syndrome (AIDS) is caused by the lentivirus, human immunodeficiency virus (HIV), which establishes latency in infected hosts (Sarngadharan et al, 1984; Wong-Staal & Gallo, 1985). The incapacitating effect of this virus on the host immune system renders the infected individuals prone to a host of opportunistic infections. The major opportunistic viral infections in AIDS are herpes simplex virus (HSV), varicella-zoster virus (VZV), and human cytomegalovirus (HCMV) (Egbert et al, 1980; Mintz et al, 1983; Frank & Raicht, 1984; Quinnan et al, 1984). The incidence of HCMV infection among AIDS patients is particularly high (Lerner & Tapper, 1984) and the infection can take many forms, including retinitis, pneumonia, colitis, and various syndromes (Egbert et al, 1980; Lerner & Tapper, 1984; Meiselman et al, 1985).

Nucleoside analogs have received considerable attention as anti-HIV drugs. Foremost among these are 3'-azido-2',3'-dideoxythymidine (ddAzThd), 2',3'-dideoxycytidine (ddCyd), and 2',3'-dideoxyinosine (ddino) (De Clercq, 1986; Tuazon & Labriola, 1987; Sandstrom & Kaplan, 1987; Eriksson et al, 1989; Donovan et al, 1991; Johnson et al, 1991; Dickover et al, 1992; Meng et al, 1992). Other major therapeutic agents that have been evaluated for their anti-HIV activities are Suramin, trisodium phosphonoformate (PFA), antimoniotungstate (HPA-23), interferons, and photoactive plants like *Hypericum perforatum* (De Clercq, 1986; Tuazon & Labriola, 1987; Hudson & Towers, 1991; Hudson et al, 1991)

None of the nucleoside analogs used to treat AIDS has any effect on any of the major opportunistic viral infections and would have to be combined with drugs like acycloguanosine (acyclovir, ACV) that are effective against the herpes viruses. PFA is effective against both HIV and herpes viruses but it has been shown to produce resistant mutants in vitro (Eriksson & Oberg, 1979) and accumulates in the bone (Hovi, 1980). The photoactive plants and interferon have broad spectrum activities against HIV and the herpes viruses but their toxicities mitigate against their systemic use (Hudson & Towers, 1991; Sandstrom & Kaplan, 1987). Other major plant products that have exhibited activities against HIV are extracts of pine cone (Lai et al, 1990; Takayama et al, 1991), plants containing lectin (Bazarini et al, 1992), cactus (Skinner & Ezra, 1993), and several Chinese herbal plants (Ho & Li, 1991).

Many families in Ghana have some knowledge of the use of some plants for the treatment of diseases. The traditional use of plants for the treatment of diseases stands the risk of extinction or adulteration unless efforts are made to document and research into such knowledge. The emerging new viral diseases without any available therapies makes it urgent therefore for the identification and testing of plants traditionally used in Ghana and elsewhere to treat viral diseases.

Several plants were collected from Ghanaian families who claimed ancestral knowledge of the use of such plants against genital herpes and shingles. A few other plants were randomly collected. Extracts of the plants were tested against HIV, herpes viruses, and some other viruses that afflict mankind. In addition, their effects on bacteria were tested.

Extracts of seven (7) out of thirty (30) plants (see Table 1), some of which are traditionally claimed as anti-infective drugs, were found to be effective in vitro against some or all of the following viruses: HIV, HSV, CMV, poliovirus, measles virus, and yellow fever virus. Six (6) plants were also inhibitory to some bacteria with two (2) of them being comparable to penicillin G and streptomycin sulfate.

This invention teaches that extracts of species of any of the eight (8) plants have a at least one pharmacologically active component, biological metabolite, derivative thereof, or a combination of the above against all or some of the following: DNA, RNA, or both DNA and RNA viruses, as well as some bacterial opportunistic infections found in immunosuppressed patients as seen in AIDS. The invention also teaches that extracts of species of any of these plants have at least one pharmacologically active component, biological metabolite, derivative thereof, or a combination of the above against some viral and some bacterial infections in immunocompetent patients.

By the term "HIV", is meant the commonly designated HIV series (human immunodeficiency virus) formerly called HTLV, LAV and ARV, and species thereof.

Similarly, the term "AIDS" shall refer to any illness or syndrome caused directly or indirectly by HIV.

Again, the term "opportunistic viral and bacterial infections in AIDS" shall refer to viral infections such as CMV and HSV types 1 and 2, and bacterial infections such as *Mycobacterium tuberculosis* and *Salmonella bacteremia* that take opportunity of immunosuppression in AIDS to establish infection in the host.

And again, the term "GHX" refers to Ghanaian plants discussed in this invention.

It is an object of the present invention to employ the plant extracts as therapeutic agents in hosts infected with HIV. In vitro studies and ex vivo studies, including the antiviral indices (AI) calculated for each extract, suggests that these extracts will be useful in pharmacological preparations as in vivo anti-HIV agents. The pharmacological preparations may contain the pharmacologically active ingredients alone or in admixture with an appropriate excipient or carrier, and may be administered to the HIV infected host by enteral, such as oral or rectal, and parenteral, such as subcutaneous, intramuscular, intraperitoneal, or intravenous route. The pharmacological agent may also be administered in combination with a supplemental antiviral agent, an antibody or a combination thereof. In addition, the pharmacological preparations according to the invention may be, for example, in dosage unit form, such as tablets, capsules, suppositories or ampoules.

It is another object of the invention to use any of the plant extracts or combination of the plant extracts, a biological metabolite, a derivative thereof or a combination of the above, in a pharmacological preparation for the treatment of opportunistic viral infections and bacterial infections in AIDS and other immunosuppressive states.

It is a further object of the invention to use the plant extracts, their active components or combinations of their components, a biological metabolite, a derivative thereof, or a combination of the above, in a pharmacological preparation for the treatment of viral and bacterial infections in immunocompetent patients.

It is still a further object of this invention to use the plant extracts, their active components or combinations of their components, a biological metabolite, a derivative thereof, or combination of the above, in a pharmacological preparation for differentiating between poliomyelitis virus types I, II, and III.

FIGURE LEGEND

FIG. 1. Concentration dependent antiviral effects of plant extracts GHX-2L (○-○-○) and GHX-2R (Δ-Δ-Δ) against HCMV strain AD169 in HEL cells. All extracts were added 2 h post virus infection.

FIG. 2. Effect of time of initiation of treatment on anti-HSV-2 strain A activities of plant extracts. 40 min (○-○-○), 1 h (Δ-Δ-Δ), 2 h (●-●-●). A. GHX-2L, B. GHX-2R, and C. GHX-6L.

FIG. 3. Toxicity of plant extracts in Vero cells determined by the tetrazolium-based colorimetric method. A. GHX-2L, B. GHX-20L, C. GHX-4R, D. GHX-6L, E. GHX-7L, and F. GHX-26F.

FIG. 4. Effects of multiplicity of infection (MOI) on anti-HIV-1 strain GH3 activities of plant extracts and ddAzThd in M8166 cells. 1. 1424 MOI (○-○-○), 0.2856 MOI (Δ-Δ-Δ), 0.0714 MOI (●-●-●), 0.0357 MOI (▲-▲-▲). A. GHX-2L, B. GHX-6L, and C. ddAzThd.

FIG. 5. Effects of plant extract GHX-2L on HIV chronically infected Molt4 clone 8 cell growth and virus production. A. Molt 4 cell growth, B. Molt 4/HIV cell growth, and C. Virus production from Molt 4/HIV cells.

FIG. 6. Effects of plant extract GHX-6L on HIV chronically infected Molt4 clone 8 cell growth and virus production. A. Molt 4 cell growth, B. Molt 4/HIV cell growth, and C. Virus production from Molt 4/HIV cells.

FIG. 7. Effects of plant extract GHX-26F on HIV chronically infected Molt4 clone 8 cell growth and virus production. A. Molt 4 cell growth, B. Molt 4/HIV cell growth, and C. Virus production from Molt 4/HIV cells.

FIG. 8. Effects of plant extract GHX-27L on HIV chronically infected Molt4 clone 8 cell growth and virus production. A. Molt 4 cell growth, B. Molt 4/HIV cell growth, and C. Virus production from Molt 4/HIV cells.

FIG. 9. In vitro toxicity of plant extracts GHX-2L (○-○-○), GHX-2R (Δ-Δ-Δ), GHX-6L (●-●-●), and GHX-7L (▲-▲-▲) in M8166 cells determined by the tetrazolium-based colorimetric method.

FIG. 10. In vitro toxicity of plant extracts GHX-2L (○-○-○), GHX-2R (Δ-Δ-Δ), GHX-6L (●-●-●), and GHX-7L (▲-▲-▲) in Molt 4 clone 8 cells determined by the tetrazolium-based colorimetric method.

FIG. 11. Effects of plant extracts on PBMCs of HIV negative healthy person. A. GHX-2L, B. GHX-6L, C. GHX-7L, D. ddcyd, and E. ddino.

FIG. 12. Effects of plant extracts on PBMCs of AIDS patient 1. A. GHX-2L, B. GHX-6L, C. GHX-7L, D. ddCyd, and E. ddIno.

FIG. 13. Effects of plant extracts on PBMCs of AIDS patient 2. A. GHX-2L, B. GHX-6L, C. ddCyd.

FIG. 14. Effects of plant extracts on PBMCs of AIDS patient 3. A. GHX-2L, B. GHX-6L, C. GHX-7L, D. ddCyd, and E. ddIno.

FIG. 15. Effects of plant extracts on PBMCs of AIDS patient 4. A. GHX-2L, B. GHX-6L, C. ddCyd, and D. ddIno.

This disclosure describes the effects of aqueous and methanol extracts on various viruses and bacteria. The aqueous extracts were prepared by boiling cut leaves (L), seeds (S), fruits (F), stems (ST), barks (B), or roots (R) in distilled water for about 10 mins. After centrifugation, the supernatants from these extracts were freeze-dried. To obtain the methanol extracts, decreasing concentrations (90%, 75%, 50%, 25%, 0% of methanol in water) were used for stepwise extraction of the freeze-dried aqueous extracts. Briefly, the highest concentration of methanol was used for several extractions until the color of the extract was nearly white. The procedure was repeated on the precipitate with the next highest methanol concentration and so on. Extracts of the same methanol concentration were then combined. The methanol extracts were boiled to near dryness and redissolved in distilled water. They were then freeze-dried. Various concentrations of the aqueous extracts and methanol extracts were made in appropriate media and tested. The plants with anti-infective activities are listed in table 1.

The following experiments are presented to indicate salient features of the invention by way of examples.

1. Inhibitory Effects of Plant Extracts Against Cytopathicity of HSV, HCMV, PV, MV, and YFV.

Cell death or cytopathicity is characteristic of HSV, HCMV, PV, MV, and YFV when these viruses are used to infect cells in vitro. Inhibition of viral induced cell death will therefore be an indication of antiviral activities of the plant extracts.

The procedure used was similar to previously published ones (Ayisi et al, 1980, 1983, 1985). Monolayer Vero cells in 96-well microtitre plates were infected with 100 $TCID_{50}$/well of HSV, PV (types 1, 2, and 3), MV, or YFV. After 40 mins or 1 hr adsorption, unadsorbed virus was removed, the monolayers washed twice, and plant extracts at various concentrations of 2-fold dilutions added. After 3 days of incubation at 37° C. in 5% $CO_2$ humidified incubator, the cytopathic effects (CPEs) were examined and scored as percentages of control untreated-infected wells. Each experiment included plant extract toxicity controls in uninfected monolayers in order to rule out toxic effects of the extracts. From concentration-effect curves, the 50% effective concentrations (EC50) were determined.

Table 2 indicates that aqueous extracts of GHX-2L, GHX-4L, and GHX-6L, had inhibitory activities against all viruses tested. GHX-7L, GHX-20L, and GHX-26F were tested against only HSV and showed selective activities against this virus. The concentrations at which the plants completely inhibited viral CPE, ie, EC100, were minimally toxic to Vero cells (see FIG. 3). There were improved activities for the 90% methanol extracts of GHX-6L and GHX-20L over the aqueous extracts (compare tables 2 and 3). With respect to anti-HCMV activities tested in human embryonic lung (HEL) cells, only the roots of GHX-2 showed activity (FIG. 1).

FIG. 2 shows that variations in the time of initiation of GHX-2L and GHX-2R treatment post virus infection did not alter their activities. GHX-6L on the other hand was more effective when treatment was started early after virus infection. GHX-6L may therefore be acting primarily on early viral events whereas GHX-2L may be acting on late viral events. The significance of example 1 is made much more clear by example 3 (see below).

2. Effects of Plant Extracts on HSV Infectious Particles Yield.

Having observed the antiviral activities by the effects of GHX extracts on cytopathicity, it was important to prove that viral replication itself was inhibited. This was done by determining the effects of the extracts on virus production (infectious virus particles yield). The procedure was the same as described in example 1 above except that at the end of the 3 days incubation, the cultures were freeze-thawed and titred for virus yield by the limiting dilution method (Ayisi et al, 1985). There were concentration dependent decreases in virus yields and this is exemplified by two plants in Table 3. This illustrates that the reductions in cytopathicity observed in example 1 are likely due to inhibitory effects of the extracts on viral replication.

3. Cytotoxicity of Plant Extracts in Vero Cells.

The procedure for plant extract toxicity controls performed in example 1 is not very sensitive to detect cell survival. The tetrazolium-based colorimetry was therefore performed to confirm results of the cytotoxicity studies obtained in example 1. Uninfected monolayer Vero cultures were exposed to various concentrations of plant extracts. After 3 days of incubation, the cultures were trypsinized and resuspended in maintainance medium. Percent cell survival compared to the control untreated cultures were determined by the tetrazolium metabolism method (Ayisi et al, 1991). The optical density (OD) values from treated wells without cells were substracted from OD values of treated wells with cells. The resultant values were expressed as percentages of control untreated wells with cells (percent cell survival).

FIG. 3 shows the effects of various aqueous extracts of plants on Vero cell monolayers. 50% toxicity was not attained at any of the concentrations tested except in the case of GHX-7L where the very high concentration of 12.28 mg/ml caused 58% toxicity. The 50% effective concentrations (EC50s) of the seven plant extracts given in Table 2, did not cause any cytotoxicities. Likewise, the 100% effective concentrations (EC100s) of the seven plant extracts caused no or minimal cytotoxicities. The plant extracts are therefore selective and true antivirals.

4. Inhibitory Effects of Plant Extracts Against Cytopathic Effects of HIV-1, Strains HTLV-IIIB and GH3 Acute Infections.

Having established the plant extracts as antivirals, especially against viruses like HCMV and HSV which are important opportunistic infections in immunosuppressed states, it was decided to test the extracts against a causative agent of immunosuppression like HIV. One of the modes of infection by HIV is acute infection whereby syncytia formation is induced by the virus leading to the death of several cells.

Example 4 demonstrates the activities of the plant extracts in HIV acutely infected cells. The determination of anti-HIV activities were similar to a previously published procedure (Ayisi et al, 1991). Briefly, 50 ul of virus or 50 ul of growth medium (plant extract toxicity controls) were added to respective wells of poly-l-lysine coated 96-well microtitre plates. 50 ul of Molt 4 clone 8 cells from $1.6 \times 10^6$ cells/ml stock was added to the wells. The plates were incubated for 1 hr and various concentrations of plant extracts added. After incubation for 5 additional days, the cultures were processed by a modified tetrazolium-based colorimetry (Ayisi et al, 1991). The formula for calculating the percent cell protection from virus induced cell death, inactivity, and/or reduced division has been published (Ayisi et al, 1991). This formula takes into account, the independent effects of the plant extracts on uninfected cells. For determining cytotoxic concentrations from the results in this example, see example 10.

Tables 4 and 5 indicate that plants GHX-2, GHX-6, GHX-7, GHX-26 and GHX-27 were all very effective inhibitors of HIV-1 strain HTLV-IIIB induced cytopathicity. The antiviral indices ranged from 18 to 110 in Molt 4 cells for extracts where 50 percent cytotoxicity values were reached.

Figure 4A:
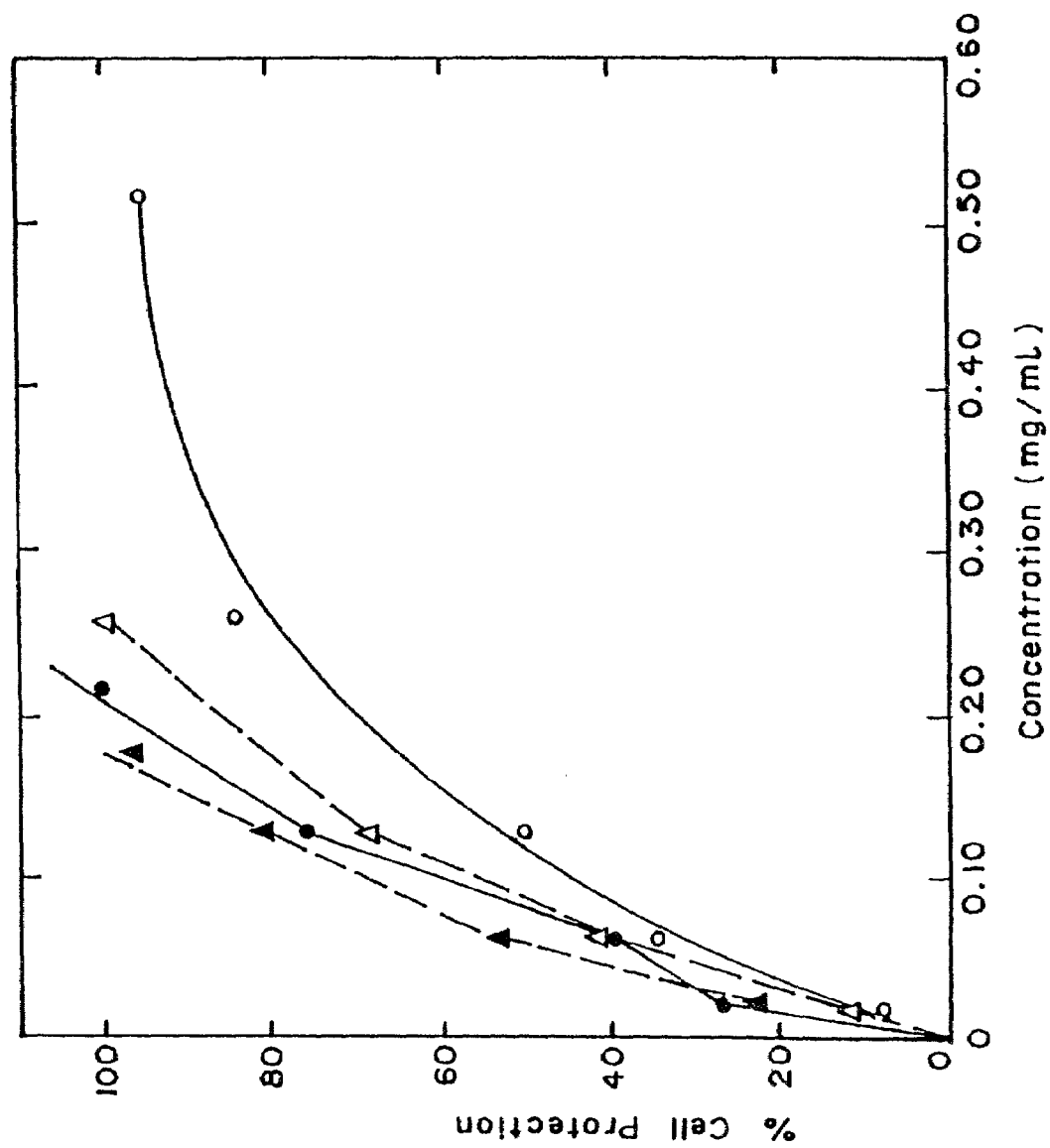
Figure 4C:
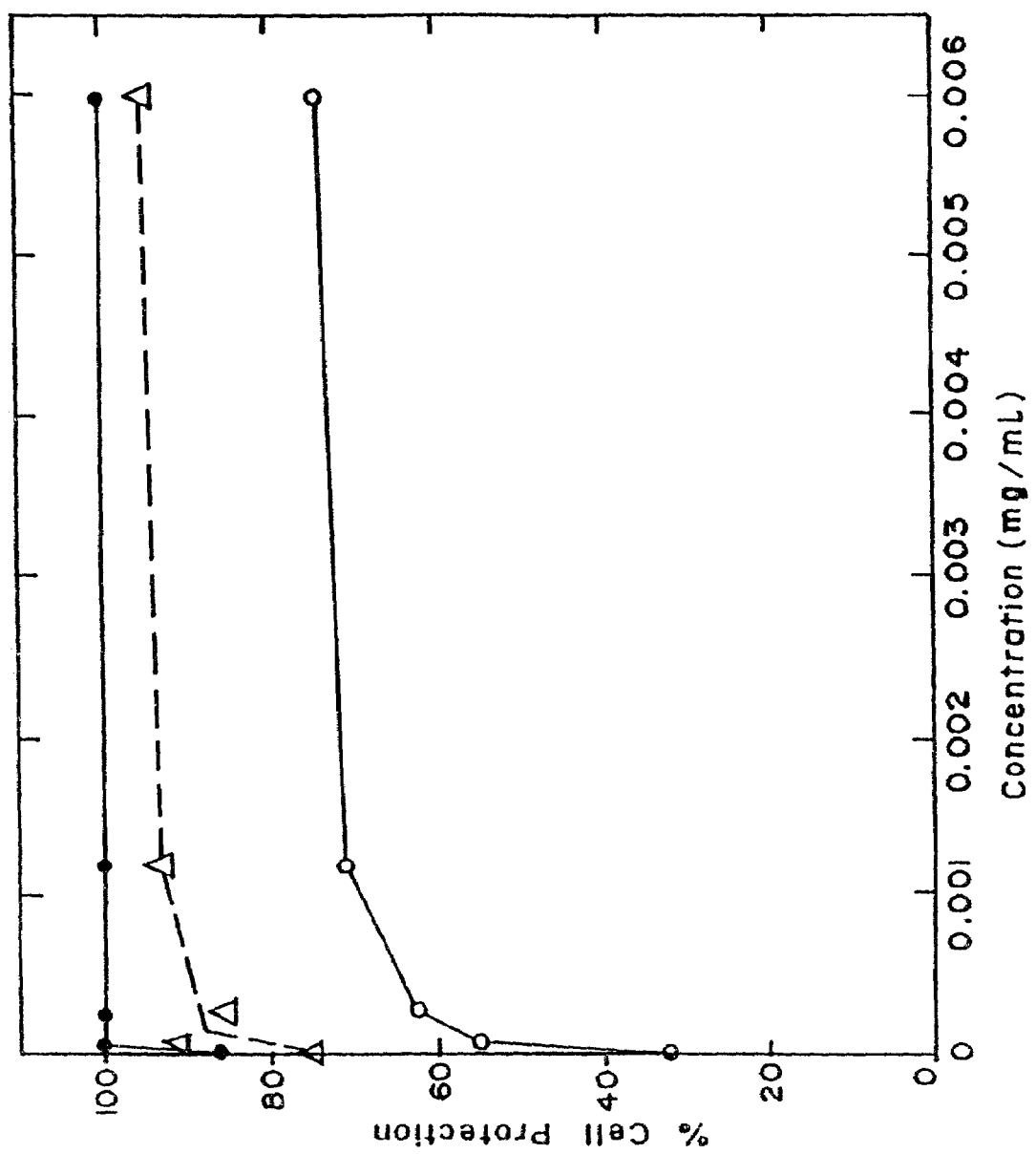
Figure 5A:
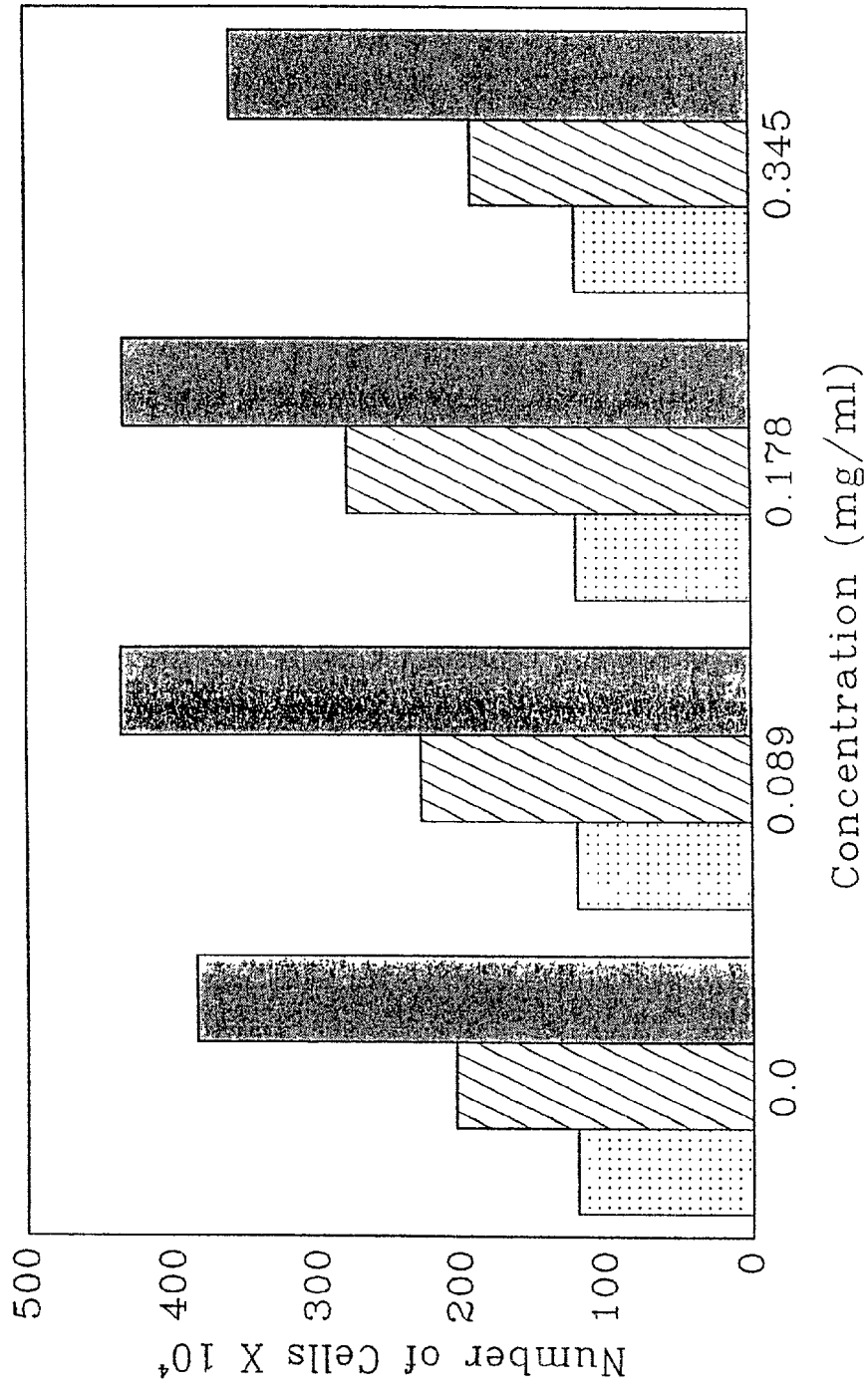
Figure 5B:
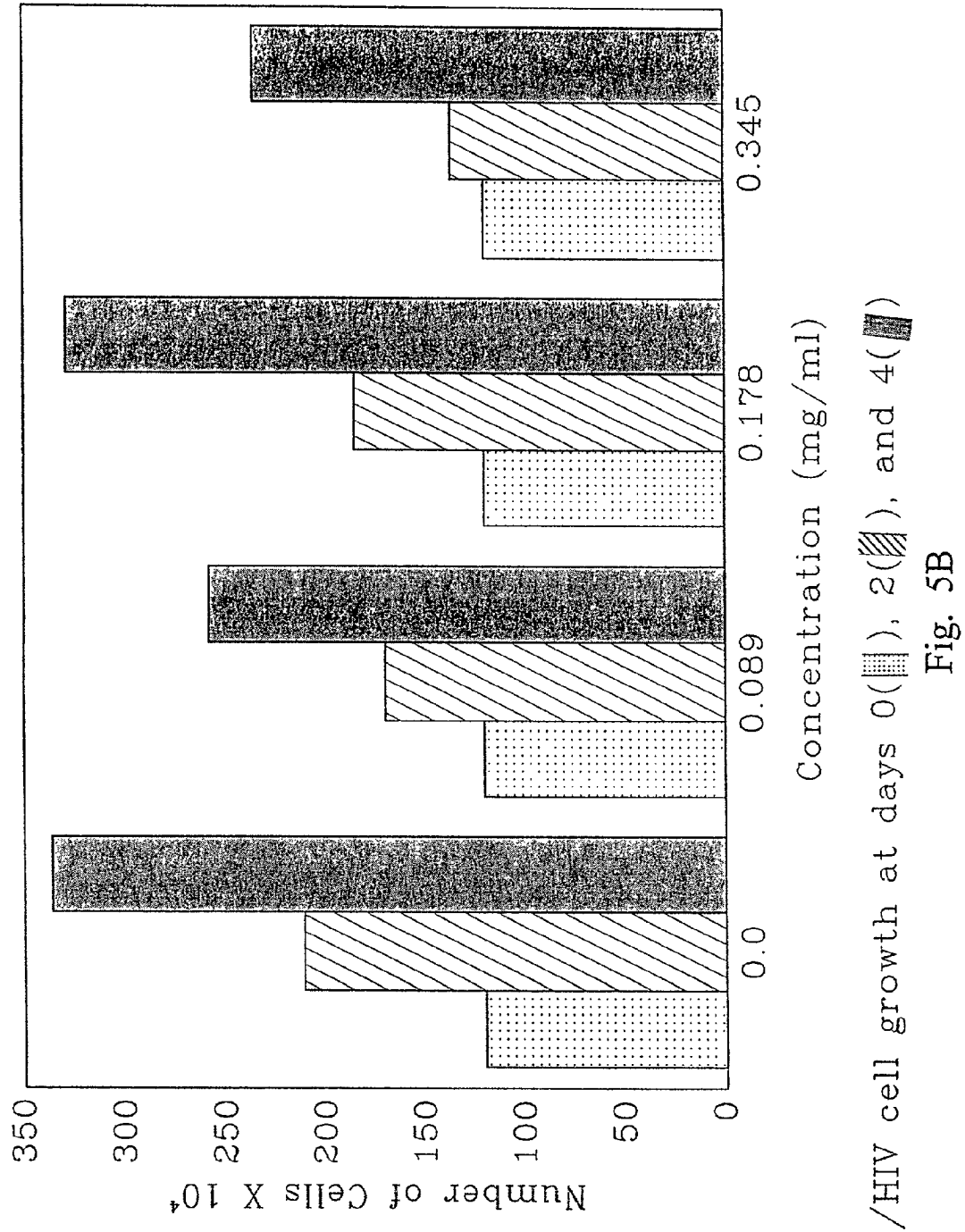
Figure 5C:
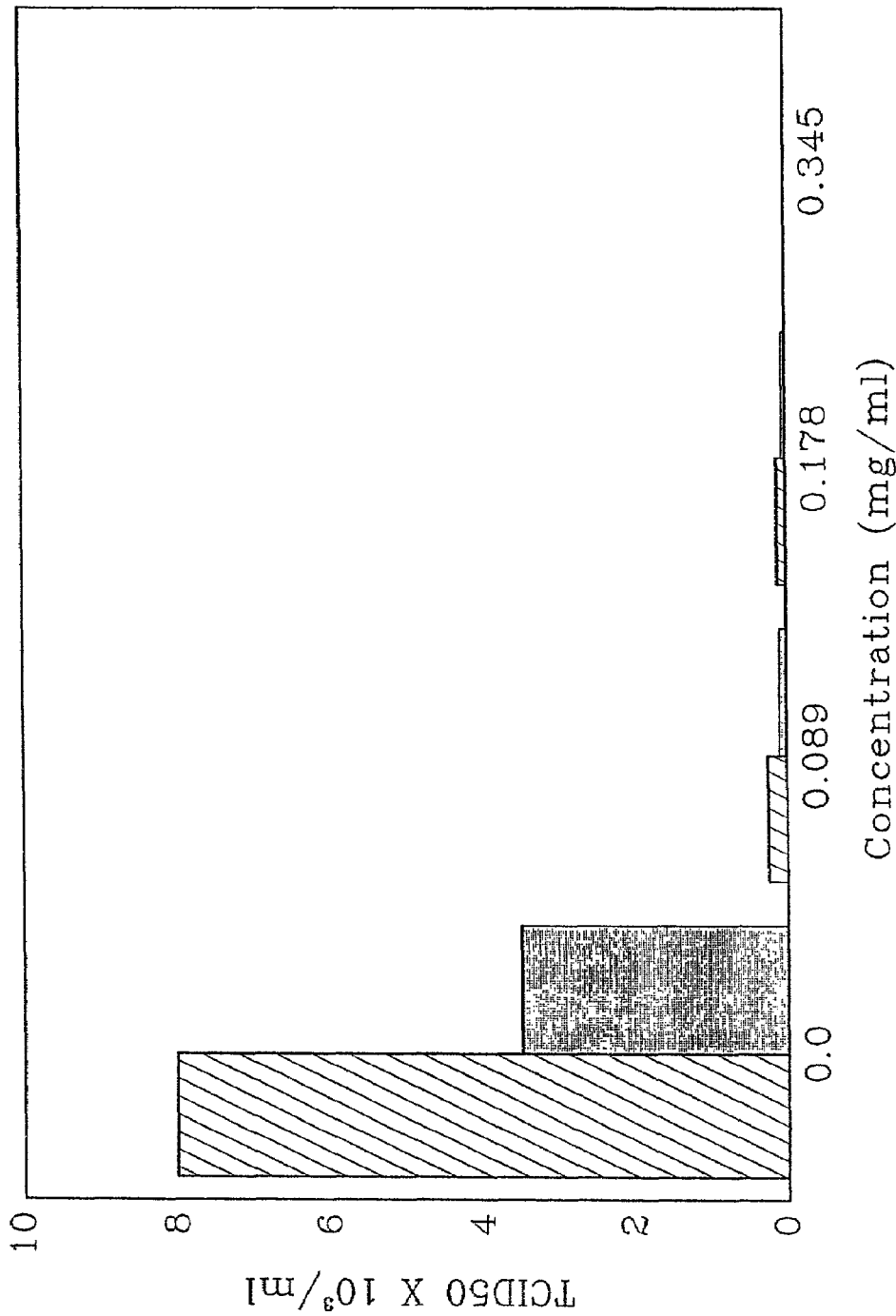
Figure 6B:
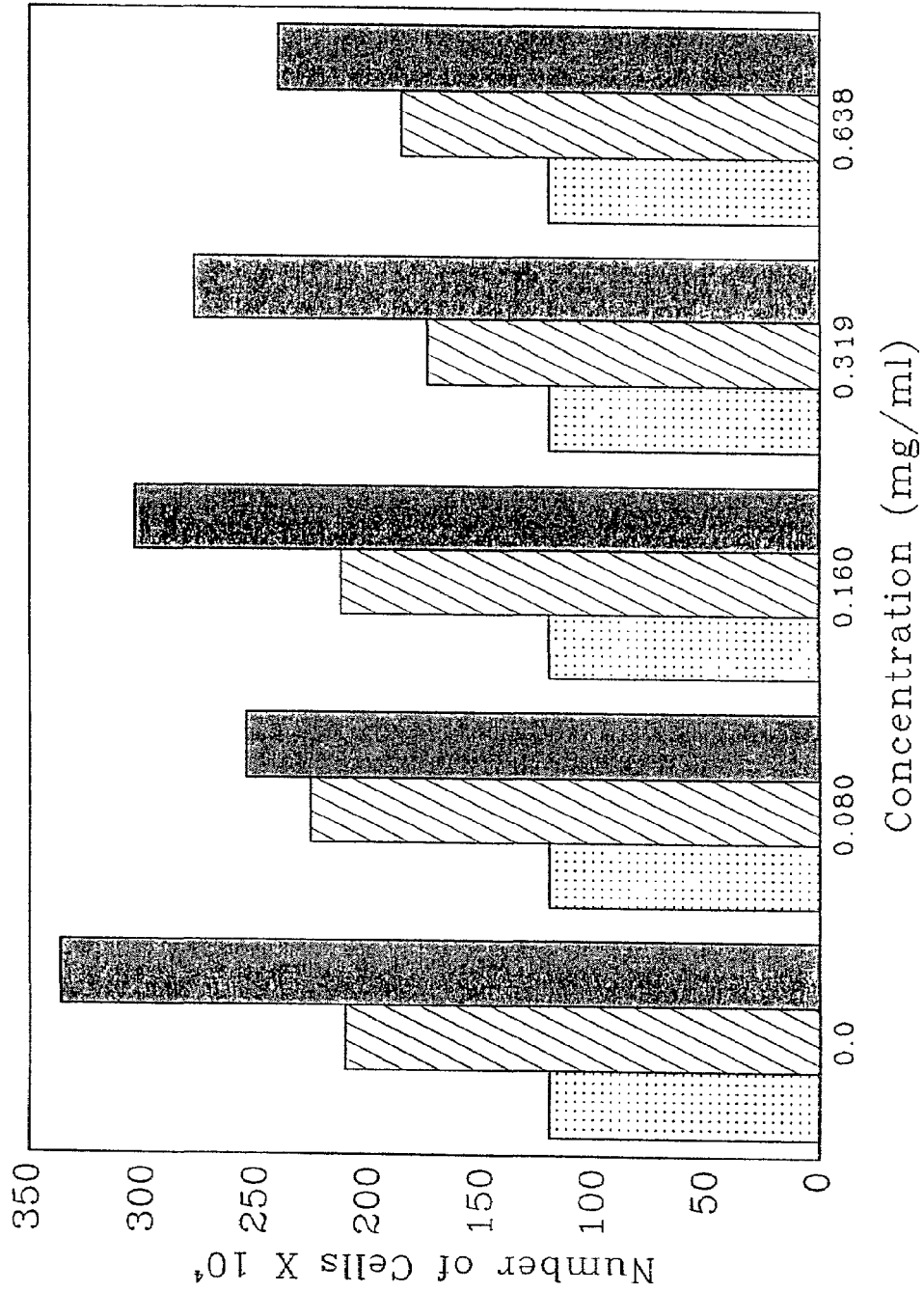
Figure 6C:
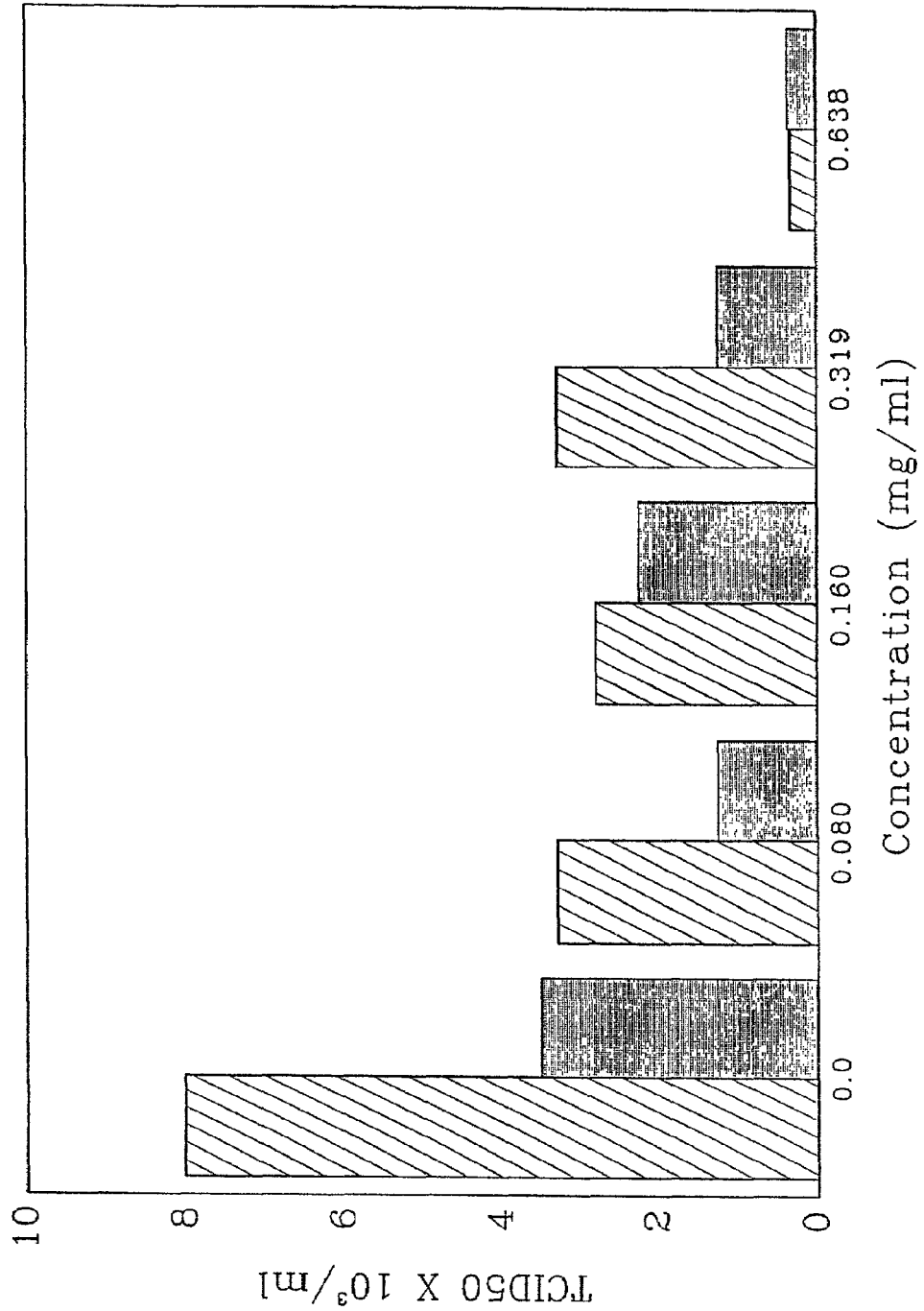
Figure 7A:
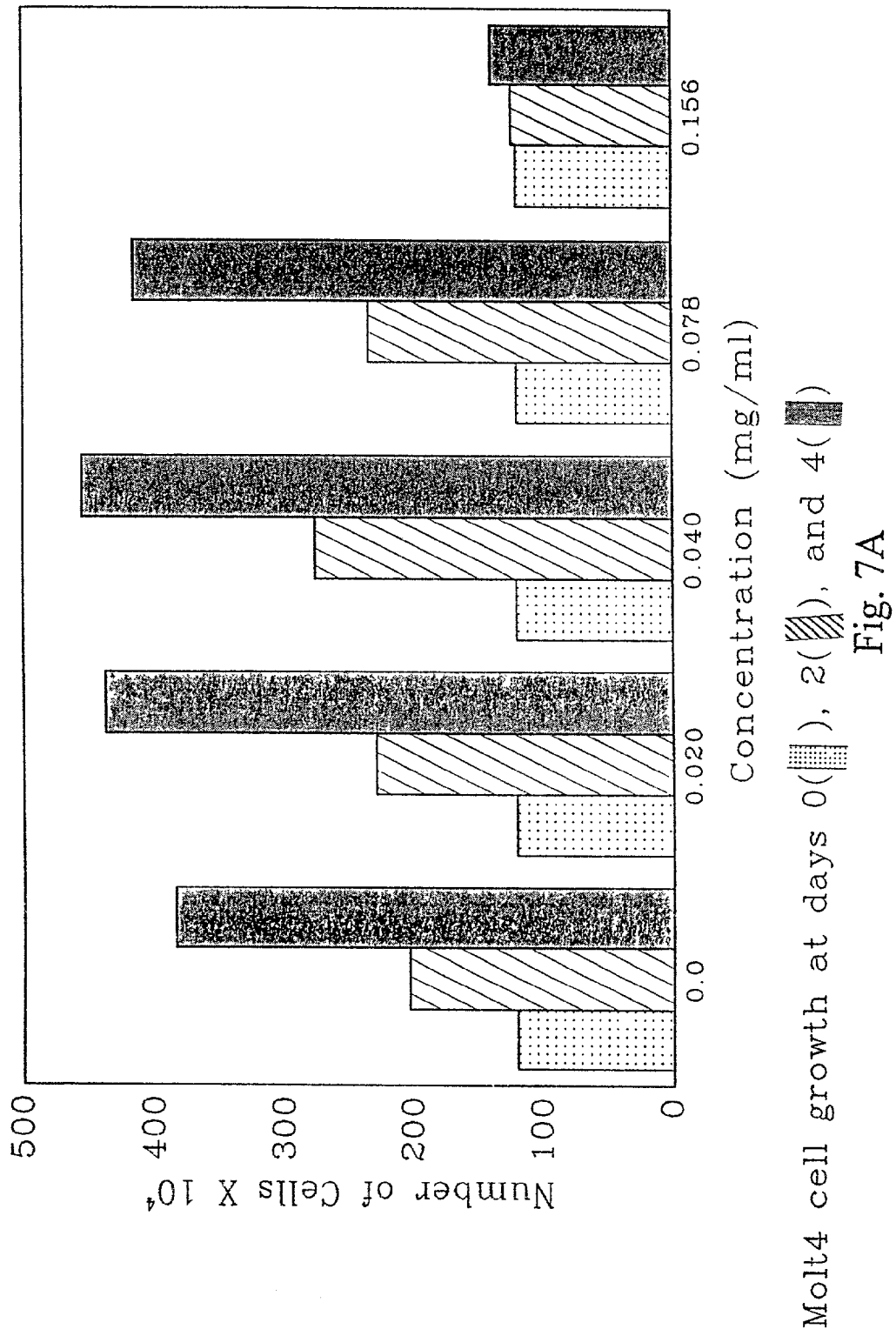
Figure 7B:
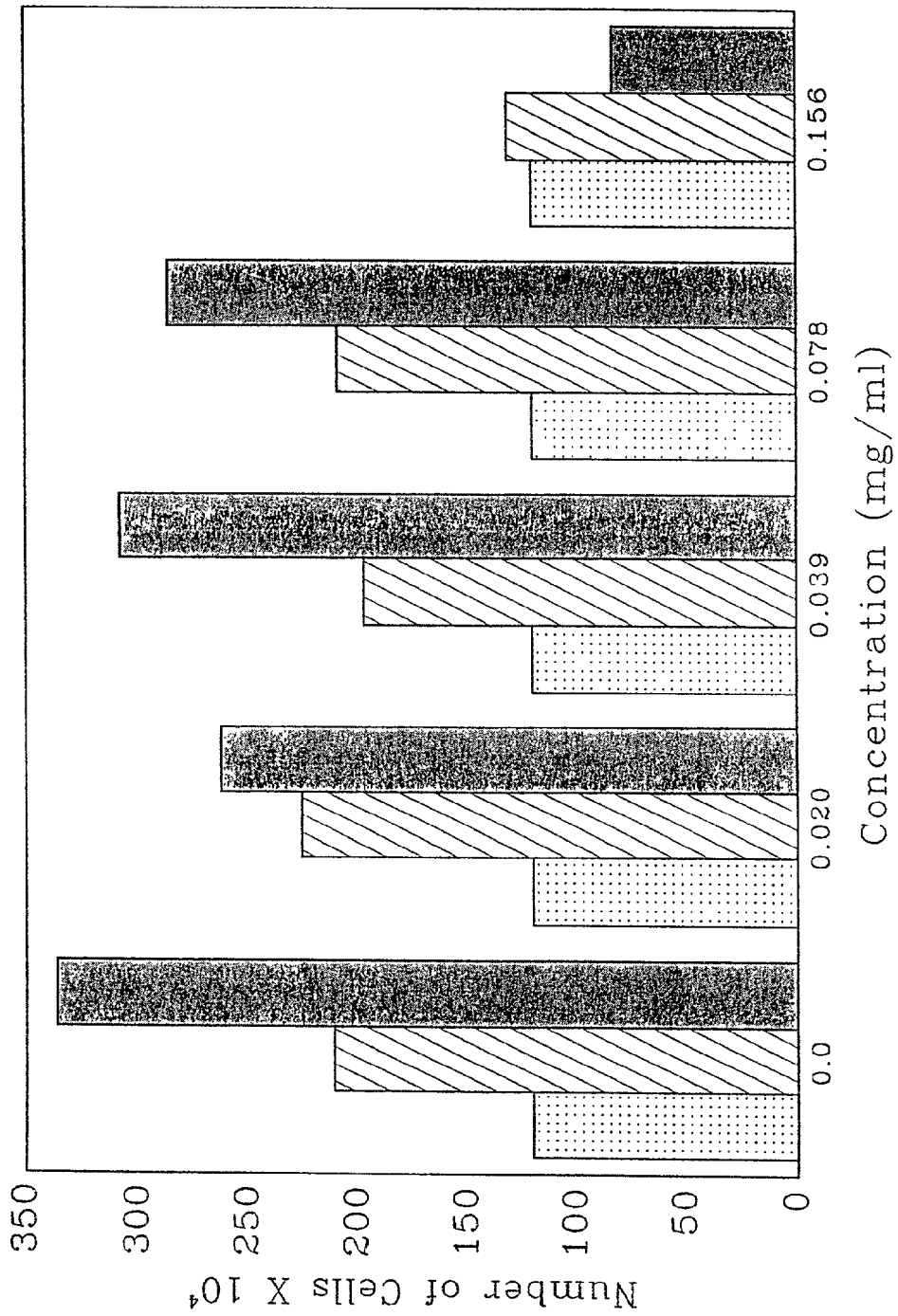
Figure 7C:
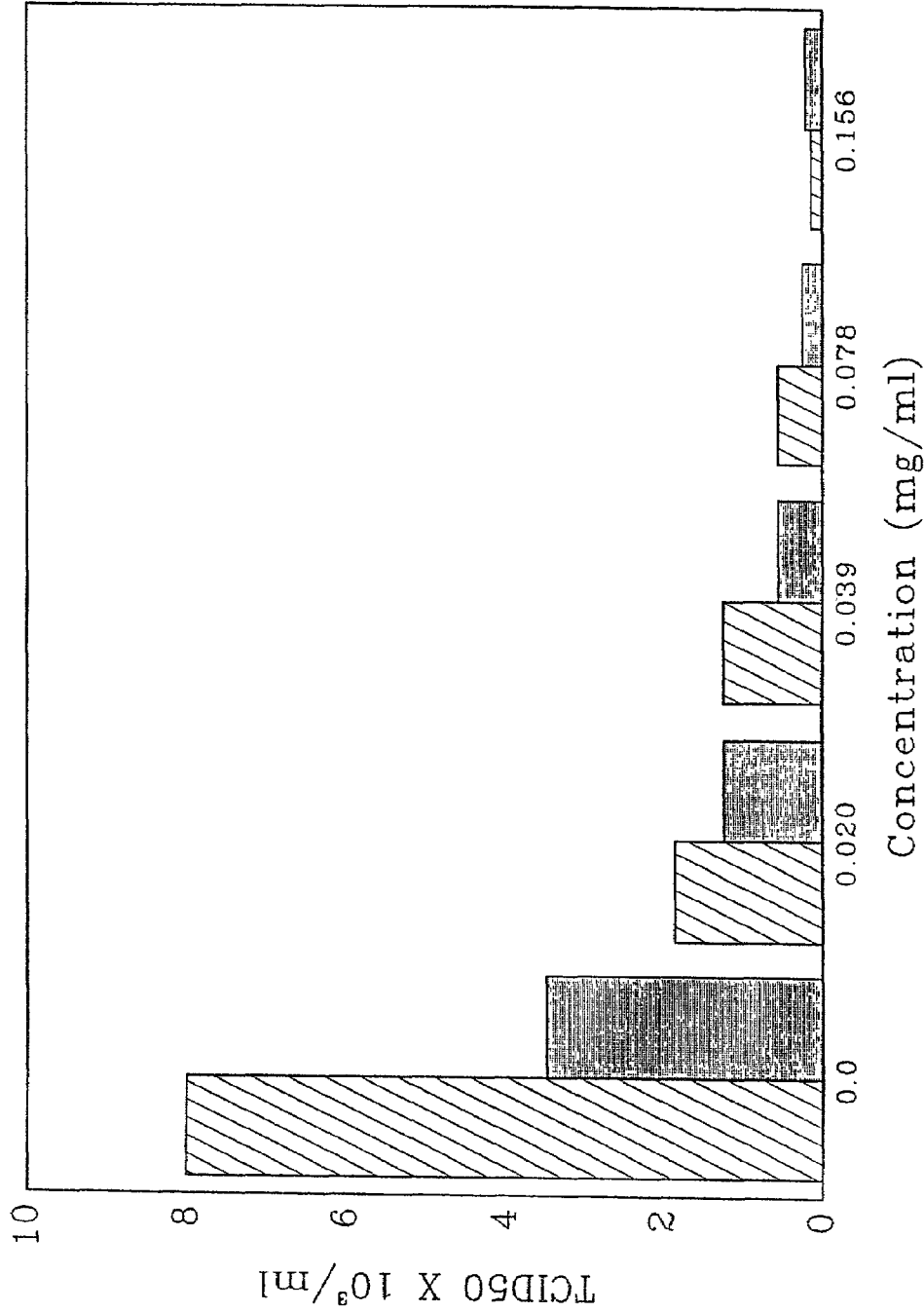
Figure 8B:
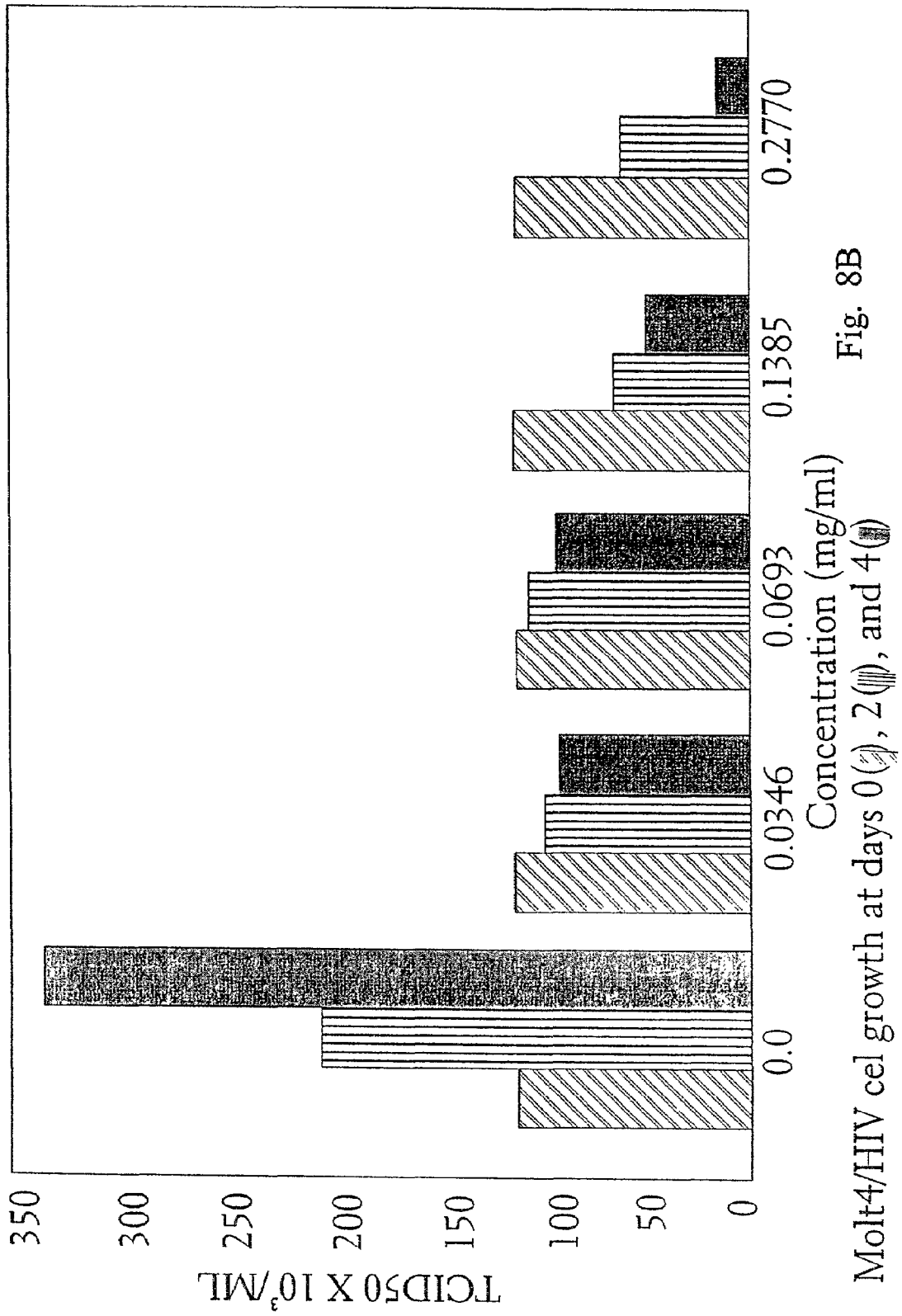
Figure 8C:
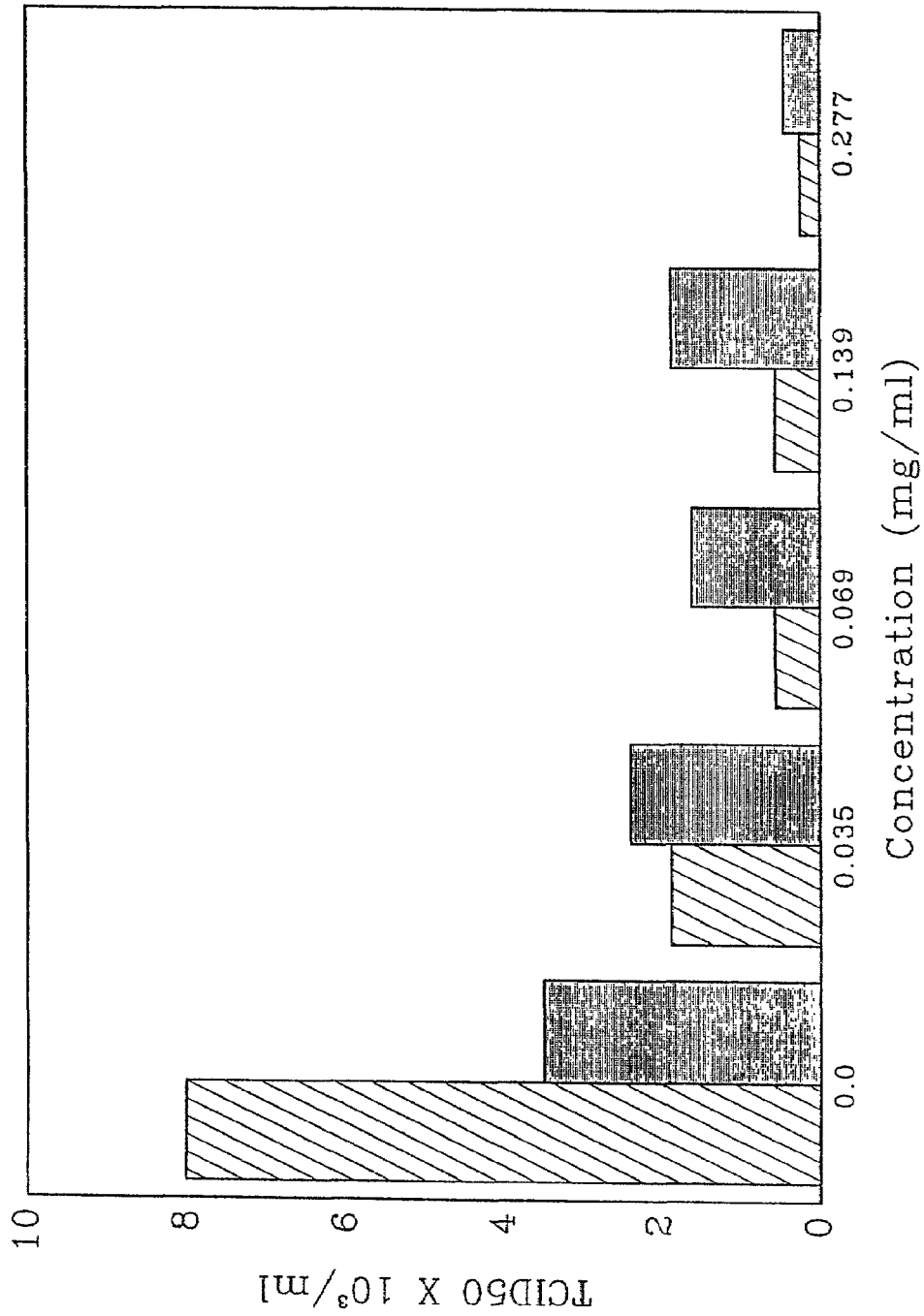

FIG. 4 shows by examples, the effects of two of the plant extracts on HIV-1 strain GH3 at four different multiplicities of infection. Plant extracts GHX-2L and GHX-6L had concentration-dependent effects at the four multiplicities of infection and both extracts were able to attain 90% cell protection even at the high multiplicity of infection of 0.11424. For the purpose of comparison, ddAzThd was included in these experiments and proved to be extremely effective except when the multiplicity of infection was increased to 0.11424 where 90% cell protection against GH3 infection was never attained. Thus under the stringent condition of high multiplicity of infection, plants GHX-2 and GHX-6 were more effective than ddAzThd. The effectiveness of the plant extracts were inversely related to the multiplicities of infection. The demonstration of concentration and multiplicity of infection dependent effects clearly indicates that the plant extracts are truly anti-HIV extracts.

5. Effects of Period of Infection Before Plant Extract Treatment on Anti-HIV-2 Strain GH1 Activities.

This example is presented to demonstrate the anti-HIV activities of the plant extracts in preventing or reducing cytopathicity in yet to be acutely infected cells and also in reducing cytopathicity in already acutely infected cultures. The method was similar to the one described in example 4.

Table 6 shows the effects of early initiation of treatment on the antiviral activities of plant extracts and ddAzThd against HIV-2 strain GH1 in Molt 4 clone 8 cells. Plants GHX-2, GHX-6, GHX-7, GHX-26, and GHX-27 had EC50 values that did not elicit any toxicities. Using EC50 values for comparison, ddAzThd and GHX-6 had time dependent decreases in activities (compare Table 6 with Table 7). The time of initiation of plant extract treatment post virus infection had little or no effect on the activities of GHX-2 and GHX-7. When the more pharmacologically accurate EC90 values were used for comparison, ddAzThd was found to be very effective only when treatment was initiated 40 mins after virus infection. Further delay in the start of treatment rendered ddAzThd ineffective. On the other hand, EC90 values were attained for GHX-2, GHX-6, and GHX-7 with minimal cytotoxicities. In fact, the EC90 values for GHX-2 and GHX-6 were markedly reduced to noncytotoxic concentrations of 0.37 and <<0.106 mg/ml respectively when the multiplicity of infection was reduced to 0.006 and treatment started as late as 15 hrs post virus infection (data not shown). Patients who report to hospital with HIV infection, already have the proviral DNA integrated into host cell genome. At 15 hrs in vitro post virus infection, proviral DNA synthesis is completed and integration into host cell genome has already taken place. Thus drugs that are able to inhibit HIV in vitro under such conditions, are likely to have beneficial effects in the treatment of AIDS. The plant extracts by virtue of their effectiveness against HIV in a system where the virus is already incorporated in the genome of the host, should be more effective than classical anti-reverse transcriptase inhibitors in the treatment of clinical AIDS.

6. Effects of Plant Extracts on Virus Production in HIV Acutely Infected Molt 4 Cells.

It was next decided to find out whether the anti-HIV cytopathicity observed for the plant extracts in example 5 was due to actual inhibition of HIV replication and virus particles production. This is important because a reduction in virus load would bear positively on the outcome of treatment of AIDS. GHX-2L and GHX-6L were selected for this experiment because of their high activities against both HIV-1 and HIV-2. Supernatants of HIV-1 or HIV-2 acutely infected Molt 4 cells were titrated in Molt 4 cells. The results in Tables 8 and 9 indicate that both extracts significantly inhibit HIV production in acute infection. Thus the inhibition of cytopathicity seen in the treatment of acute HIV infection in example 4 was likely due to inhibition of virus production.

7. Comparative Effects of Plant Extracts on the Replication and Viability of Molt-4/HIV (Chronically Infected) and Uninfected Molt-4 Cells.

Chronic HIV infection of CD4+ lymphocytes in AIDS may not play a direct role in CD4+ lymphocytopenia. However, these chronically infected cells may serve as factories of HIV production that would cause acute cytopathic infection in uninfected lymphocytes leading to CD4+ lymphocytopenia. A drug may be effective in reducing or stopping this indirect HIV induced CD4+ lymphocytopenia by two different ways.

First, the drug may selectively kill the HIV chronically infected cells at concentrations that have no adverse effects on uninfected cells. Second, the drug may inhibit HIV production from the chronically infected cells. The first mechanism is tested in example 7 and the second mechanism will be described in example 8.

HIV-1 chronically infected Molt-4 cells (Molt-4/HIV) were extensively washed to remove the previously produced viral particles from the media. After washing, $3 \times 10^4$ cells/ml were cultured in the presence of various concentrations of plant extracts in a humidified $C_2$ incubator at 37° C. Uninfected Molt-4 cells were also cultured in the presence of similar concentrations of plant extracts. The number of viable cells were counted by the trypan blue exclusion method on days 2 and 4.

FIGS. 5, 6, 7, and 8 show that there were very slight reductions in Molt-4/HIV cell numbers as compared to uninfected Molt-4 cell numbers for GHX-2L, GHX-6L, and GHX-26F treated cultures. For each of the three treatments and the untreated control, there were increases in cell number relative to increases in days of culture. On the other hand, GHX-27L caused concentration dependent decreases in Molt-4/HIV cell number with little or no effect on uninfected Molt-4 cells. This indicates that one of the possible mechanisms of GHX-27L anti-HIV activity may be due to selective killing of HIV-infected cells. GHX-27L by selectively killing HIV chronically infected cells, should be able to inhibit indirect acute infection and cytopathicity and thus prevent CD4+ lymphocytopenia in AIDS patients. It is very significant to note that up to date, no other drug or plant extract has been shown to be able to selectively kill HIV chronically infected cells.

8. Effects of Plant Extracts on Virus Production in HIV-1 Chronically Infected Molt 4 Cells.

This example is presented to test whether any of the plant extracts will be able to inhibit HIV production in chronically infected cells and thus indirectly reduce HIV induced acute infection and cytopathicity. Supernatants from treated and untreated HIV-1 chronically infected Molt 4 cells (Molt-4/HIV) were titrated in MT-4 cells.

FIGS. 5, 6, 7, and 8 show that GHX-2L caused very significant concentration dependent reductions in virus yield with a concentration of 0.089 mg/ml causing >97% reduction in virus yield. GHX-26F was also significantly effective in reducing the amount of virus production. GHX-6L and GHX-27L on the other hand, had only moderate effects on virus production from the chronically infected cells. Thus, GHX-2L and GHX-26F significantly inhibit late viral events and would inhibit indirect acute infection and cytopathicity and thus prevent CD4+ lymphocytopenia in AIDS patients. It should be noted that this property is an advantage over the classical nucleoside analogs like ddAzThd which do not affect HIV production from chronically infected cells.

9. Effects of Plant Extracts on HIV Reverse Transcriptase Activity.

This example is presented to illustrate the effects of plant extracts on a key HIV induced enzyme that is essential in HIV acute infection. Inhibition of this enzyme would protect uninfected cells against HIV infections. The effects of plant extracts on reverse transcriptase (RT) activity in vitro were evaluated with enzyme from disrupted HTLV-IIIB particles.

RT assays were performed at 37° C. for 60 min with 50 ul of a reaction mixture containing 50 mM Tris-HCl (pH 8.4), 2 mM dithiothreitol (DTT), 100 mM KCl, 10 mM $MgCl_2$, 0.01% Triton X-100, 1.25 uCi of [3H]-thymidine triphosphate, 50 ug/ml of poly(rA)-oligo(dT), 5 ul of test extract, and 5 ul of RT enzyme. The reaction was stopped by adding 5% trichloroacetic acid (TCA). Precipitates were then collected on glass fiber filters, washed with PBS, dried, and the radioactivity was measured in a liquid scintillation counter. The assays were carried out in triplicate.

All the four plant extracts tested (GHX-2L, GHX-6L, GHX-26F, and GHX-27L) showed concentration dependent reductions in RT activity (see Table 10). GHX-2L, GHX-6L, and GHX-26F caused 90% reduction of RT activity at concentrations between 0.013 and 0.020 mg/ml. On the other hand, GHX-27L was not able to cause 90% reduction in RT activity even at the highest concentration of 0.133 mg/ml tested.

10. Effects of Plant Extracts on Molt 4 Clone 8 and M8166 Cells.

Figure 9:
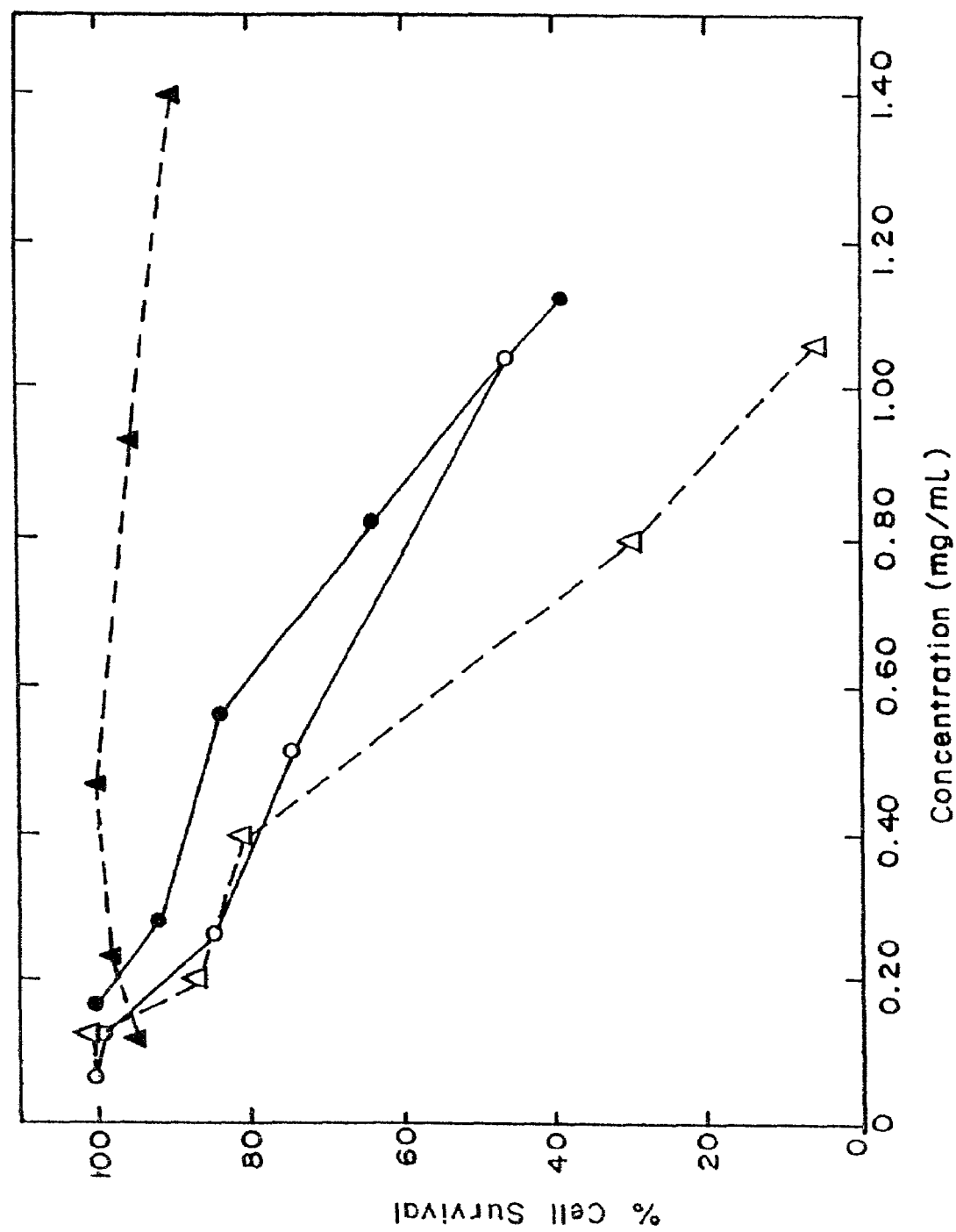
Figure 10:
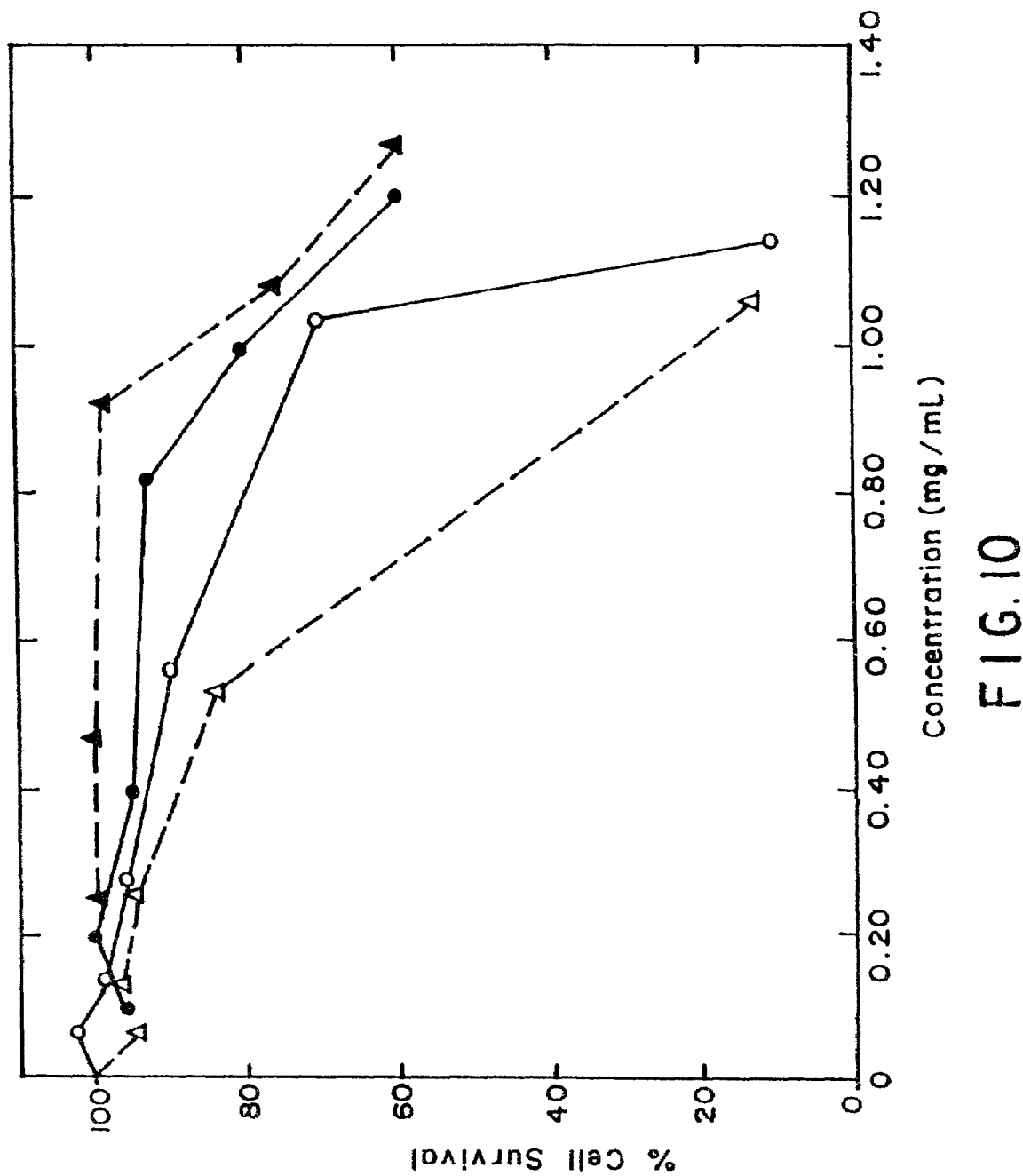
Figure 11A:
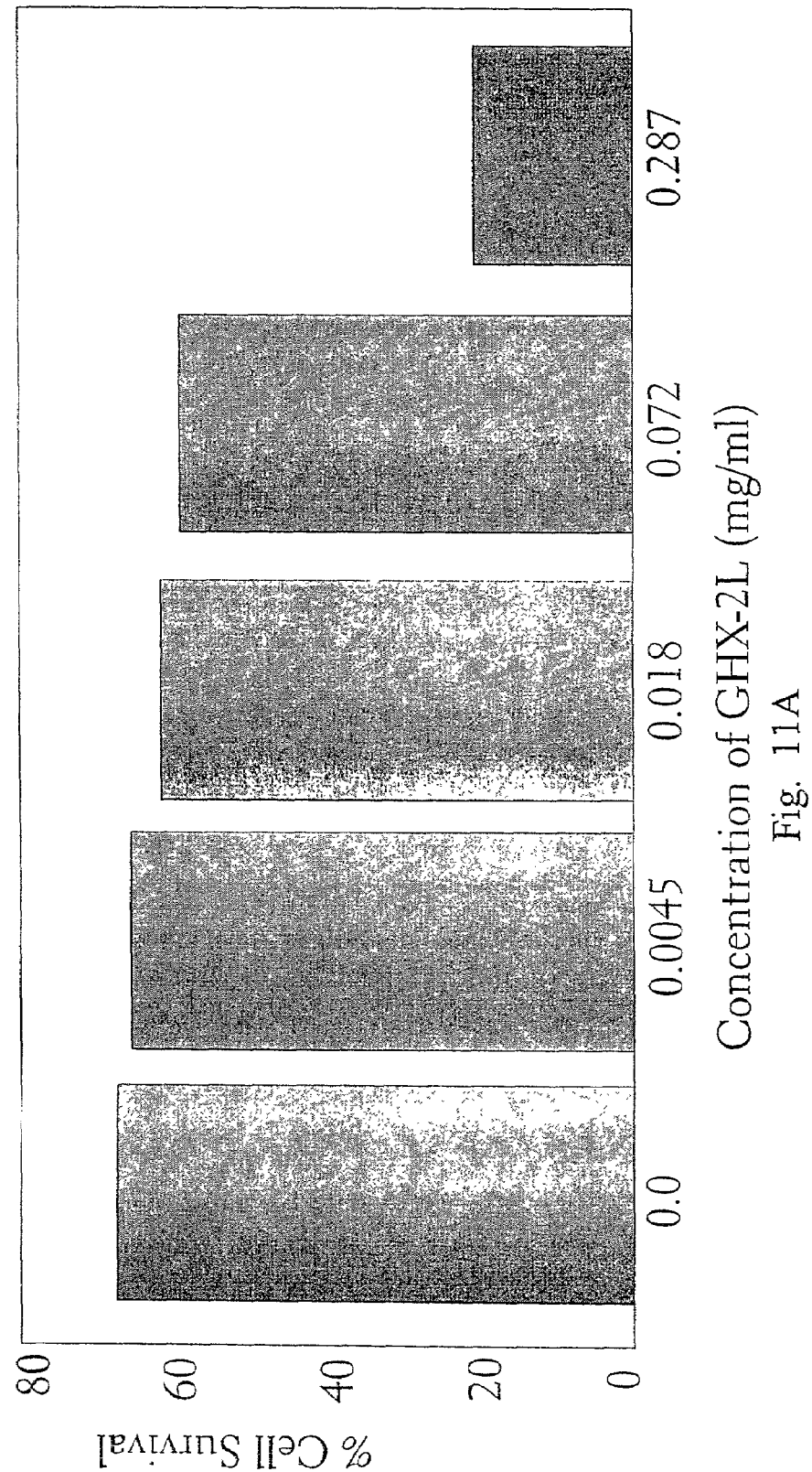
Figure 11B:
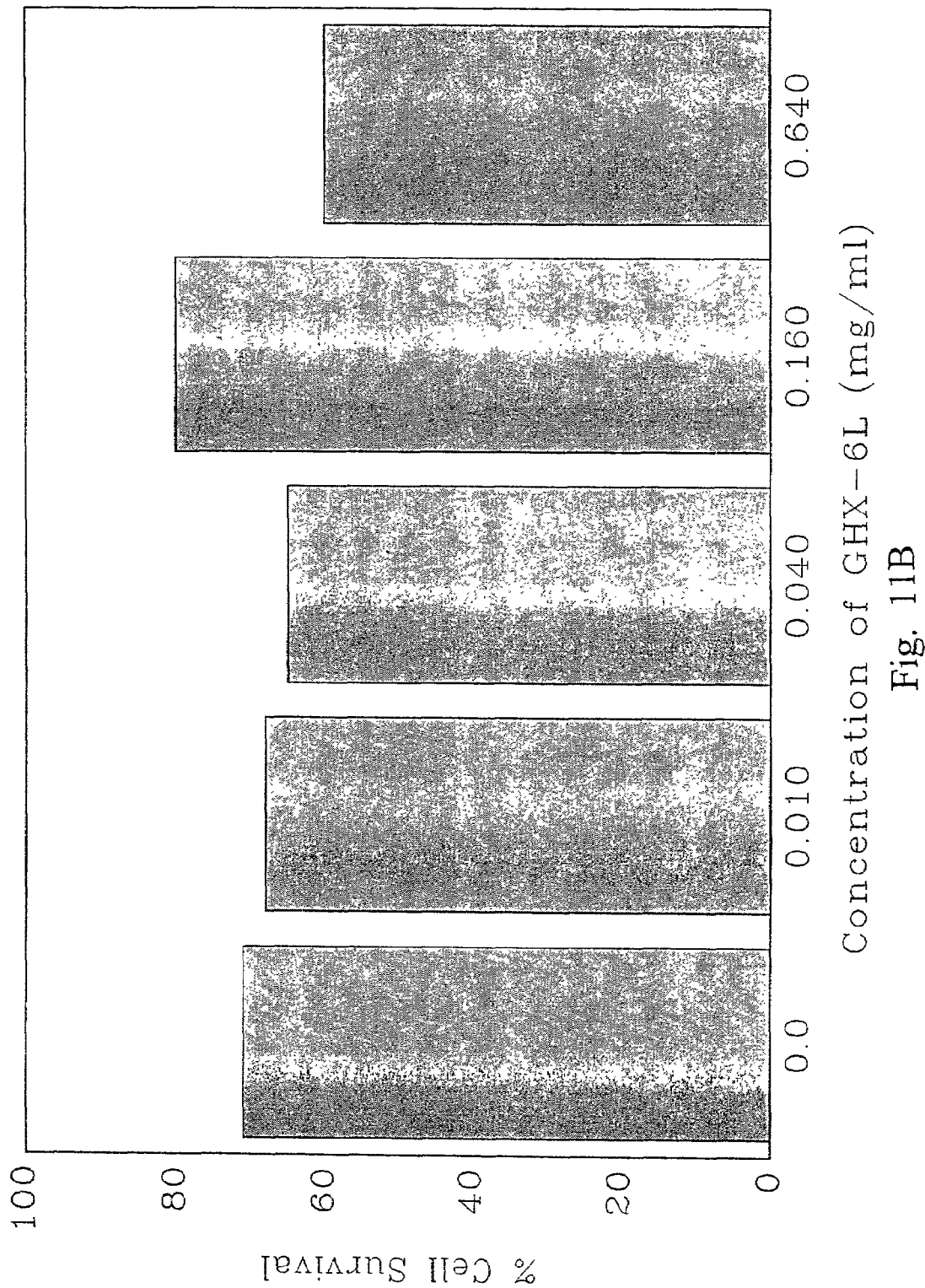
Figure 11C:
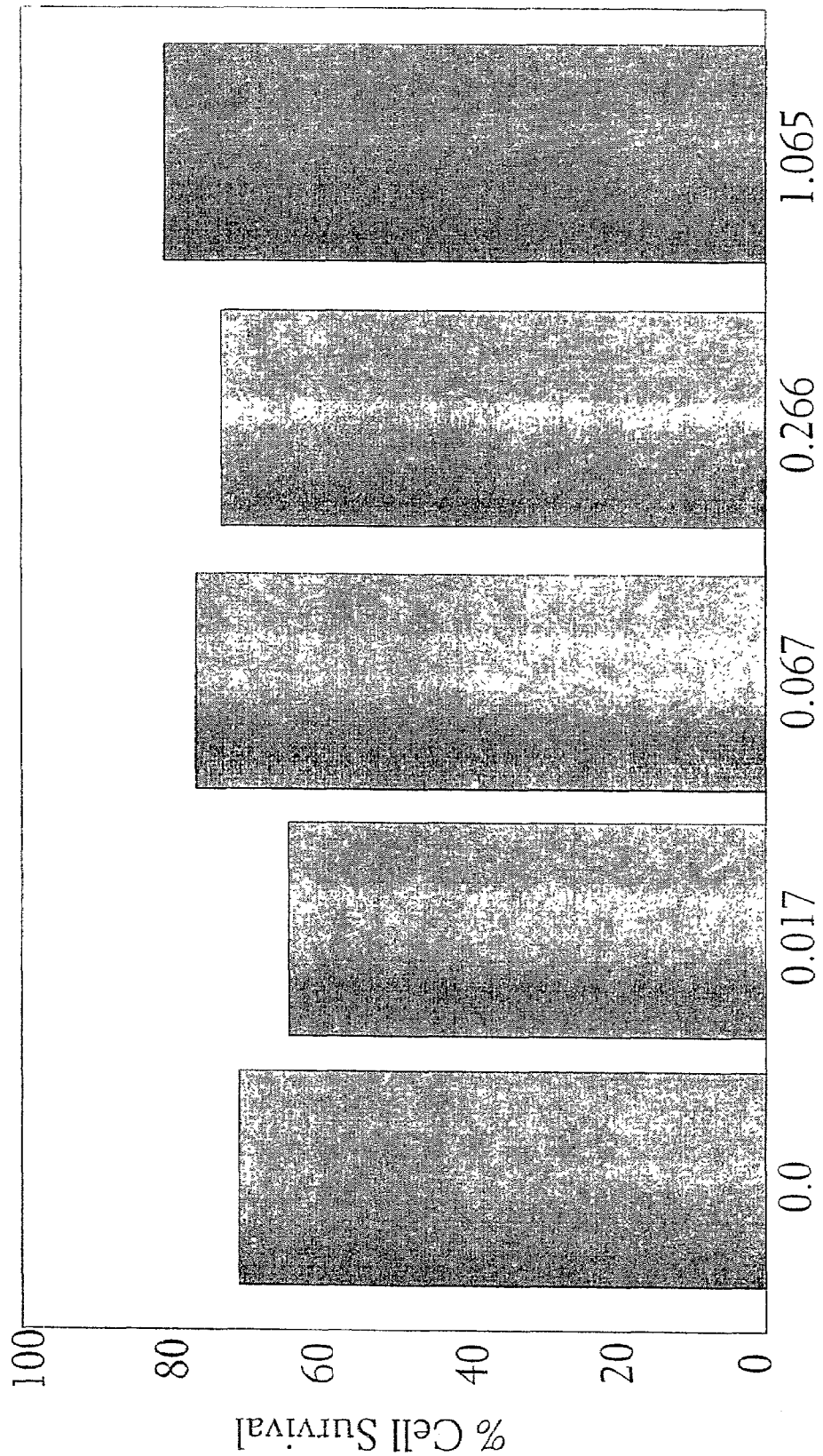
Figure 11D:
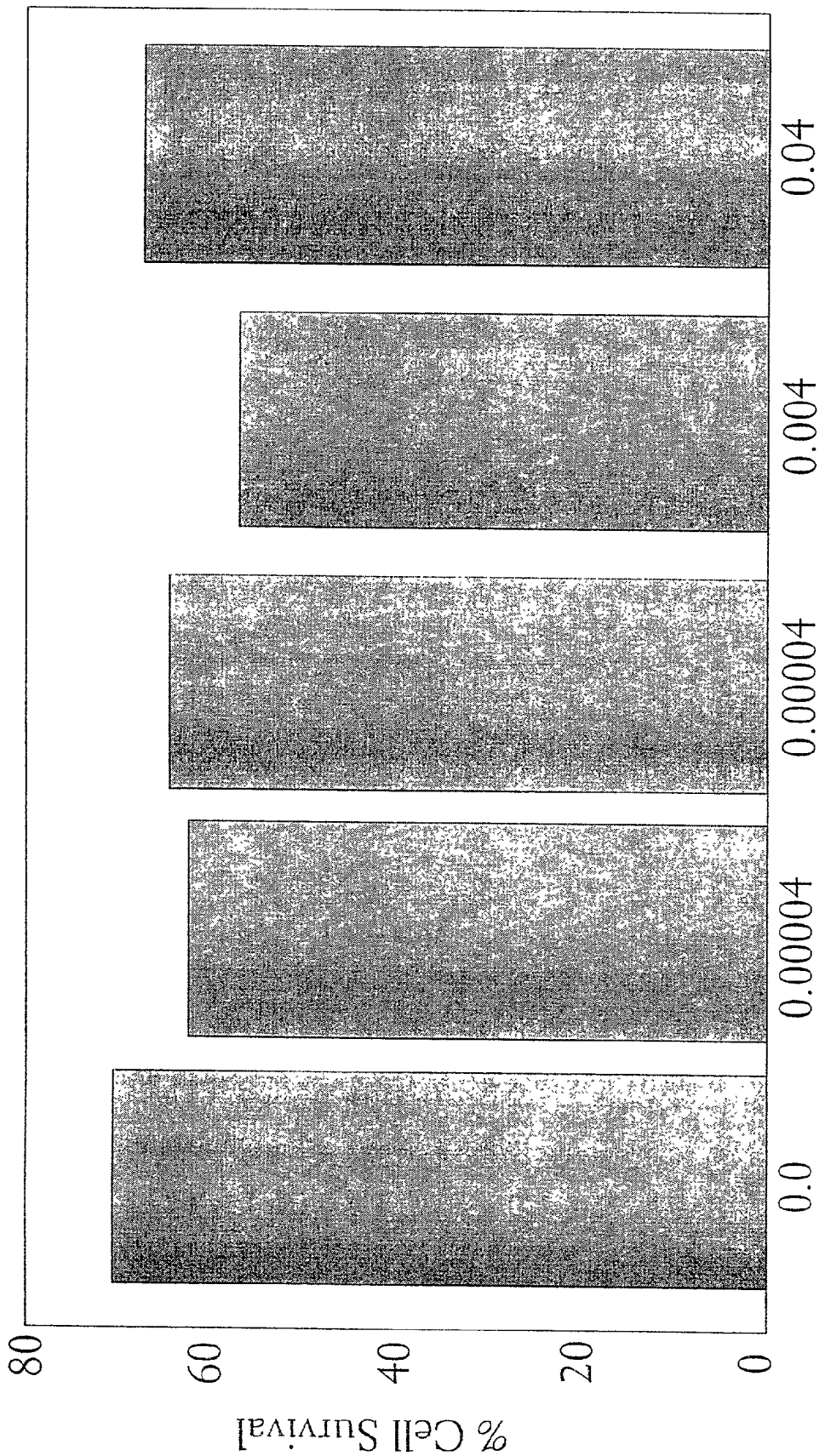
Figure 11E:
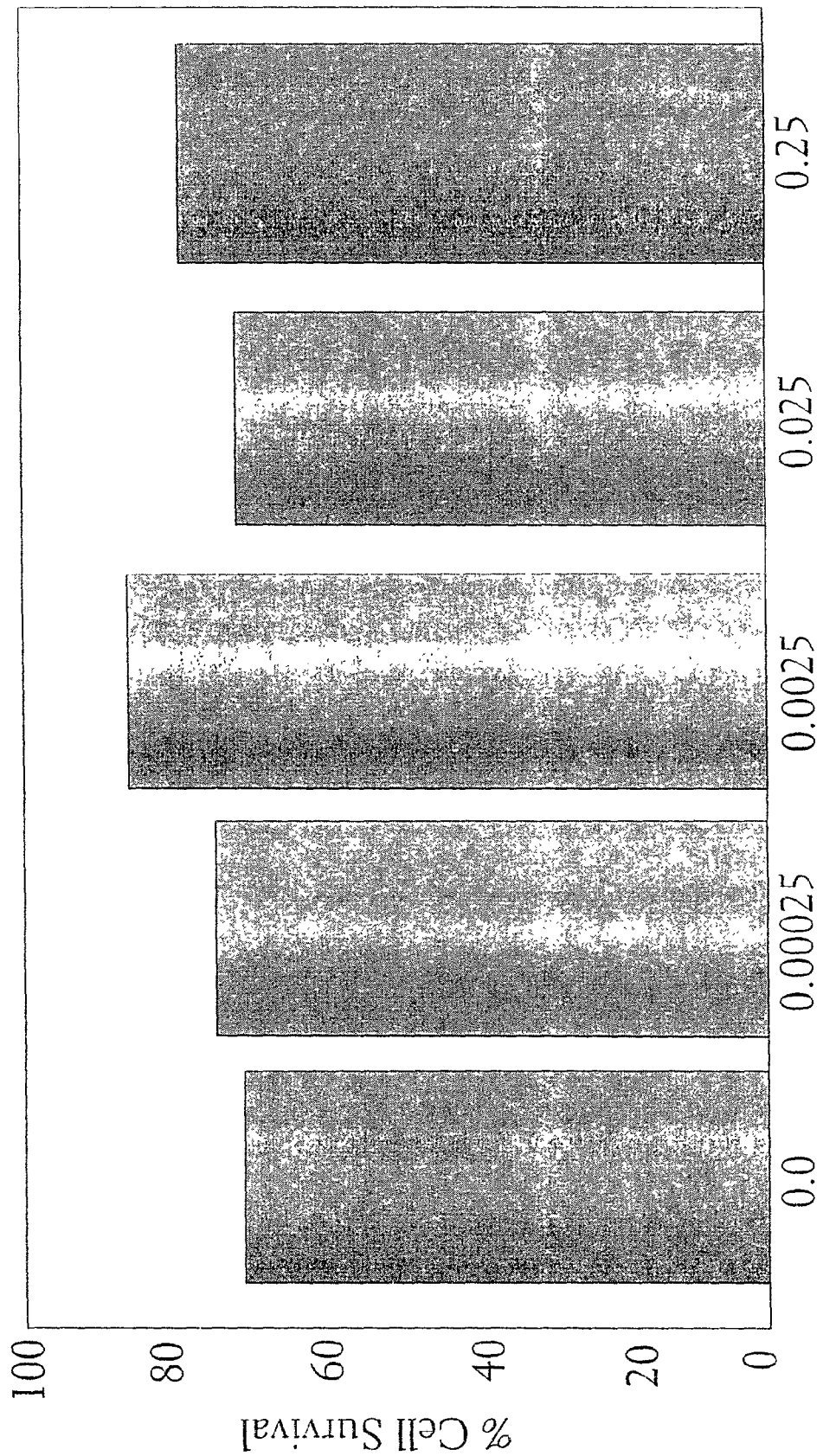
Figure 12A:
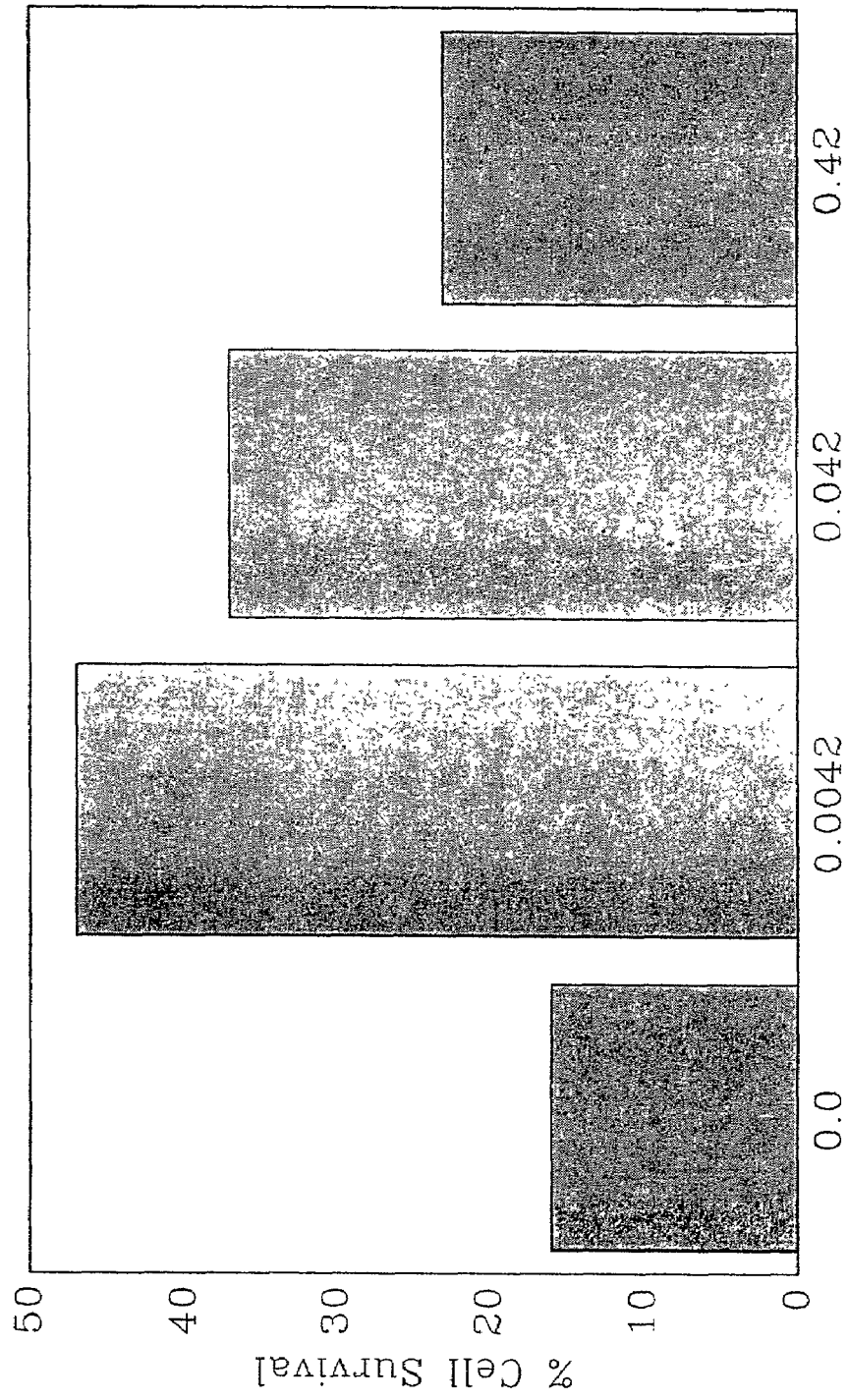
Figure 12C:
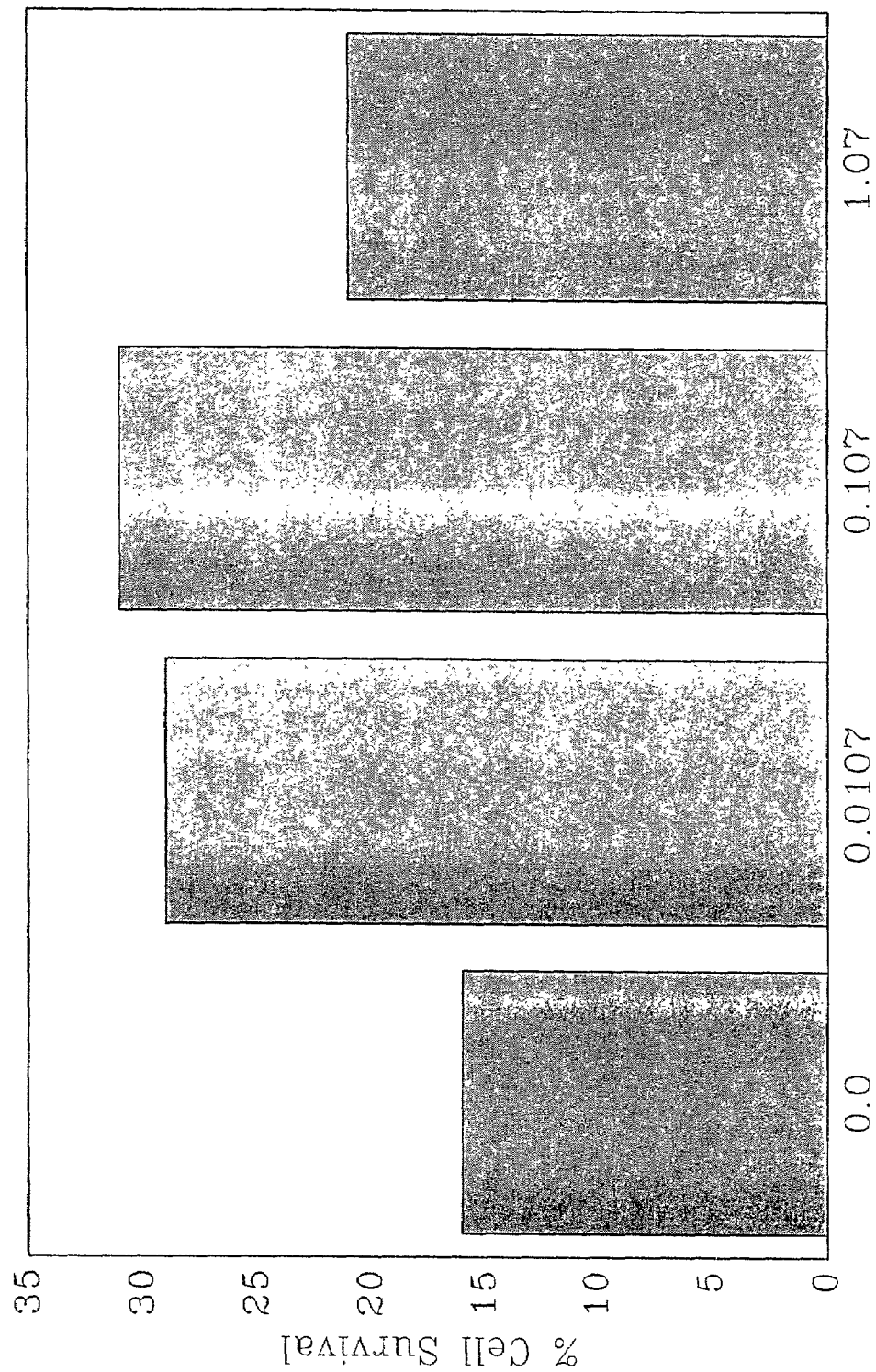
Figure 12D:
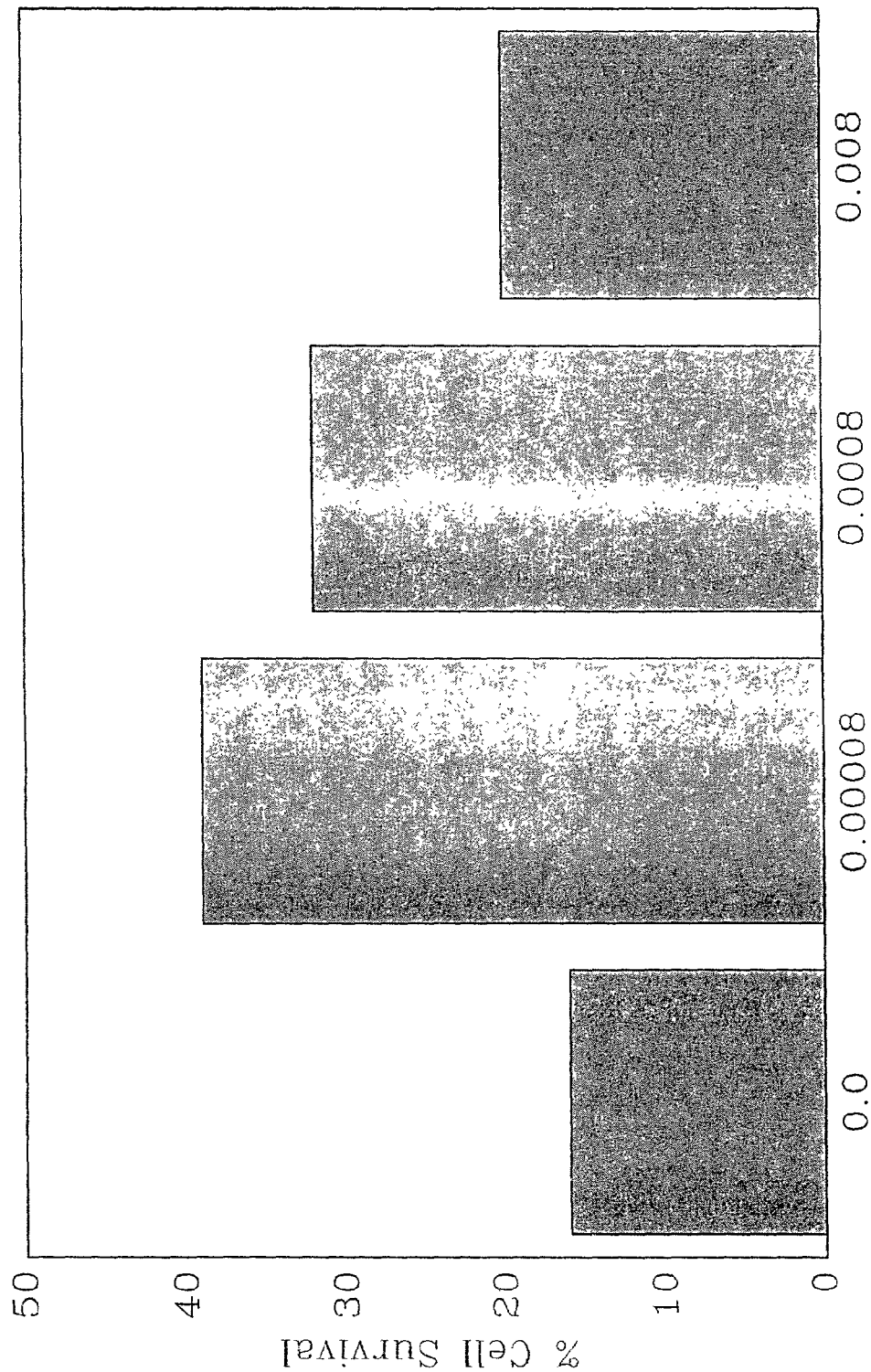
Figure 12E:
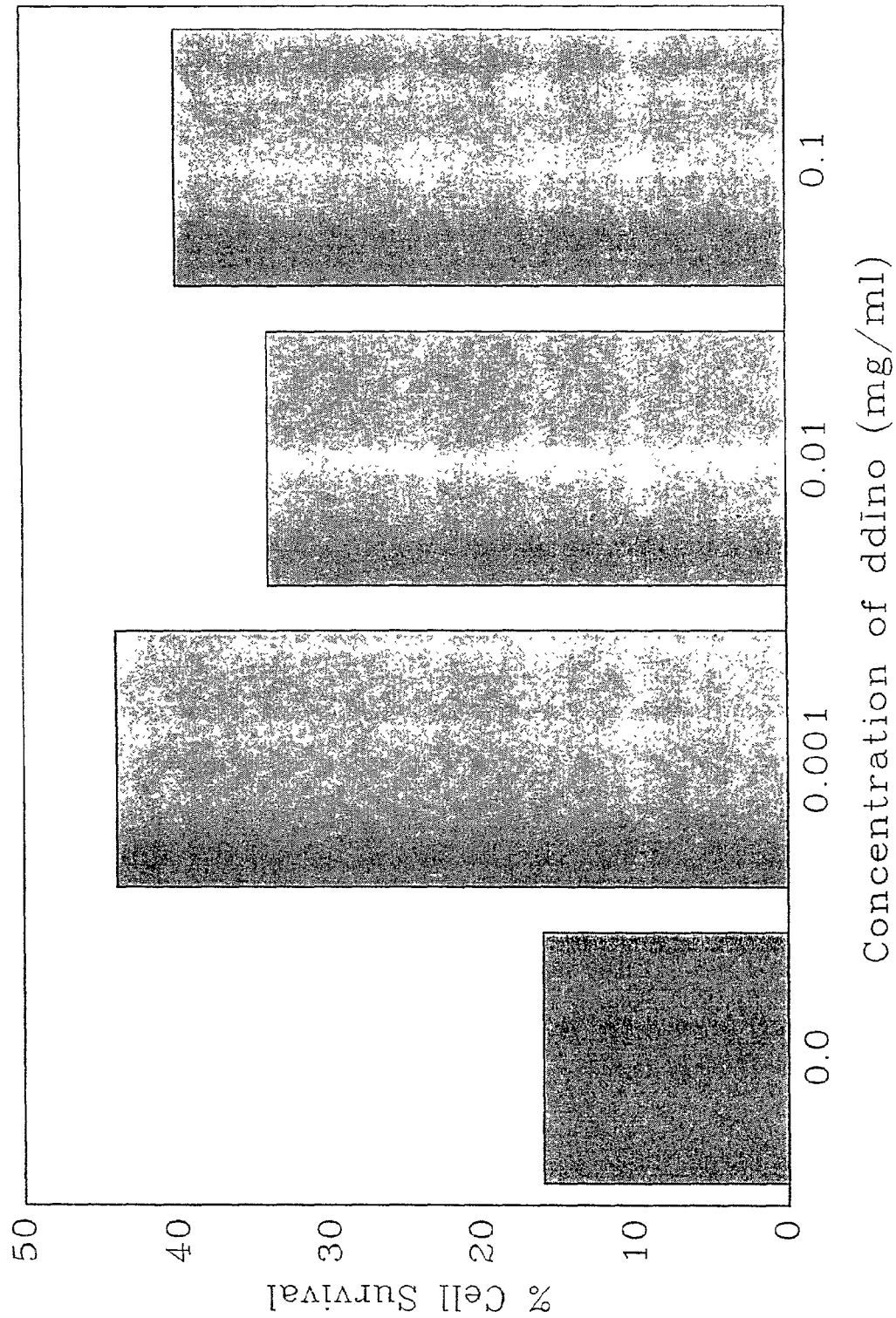
Figure 13A:
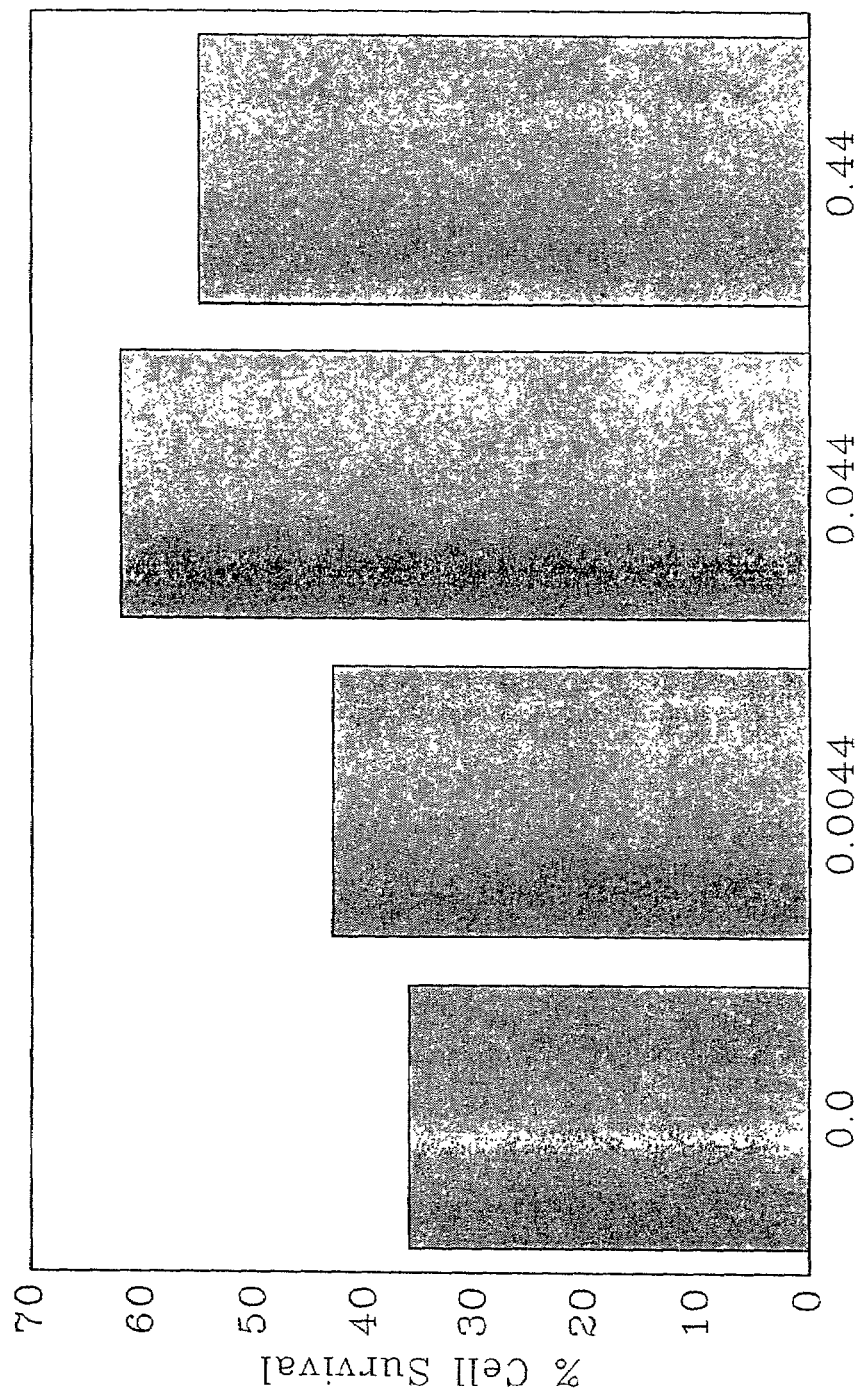
Figure 13C:
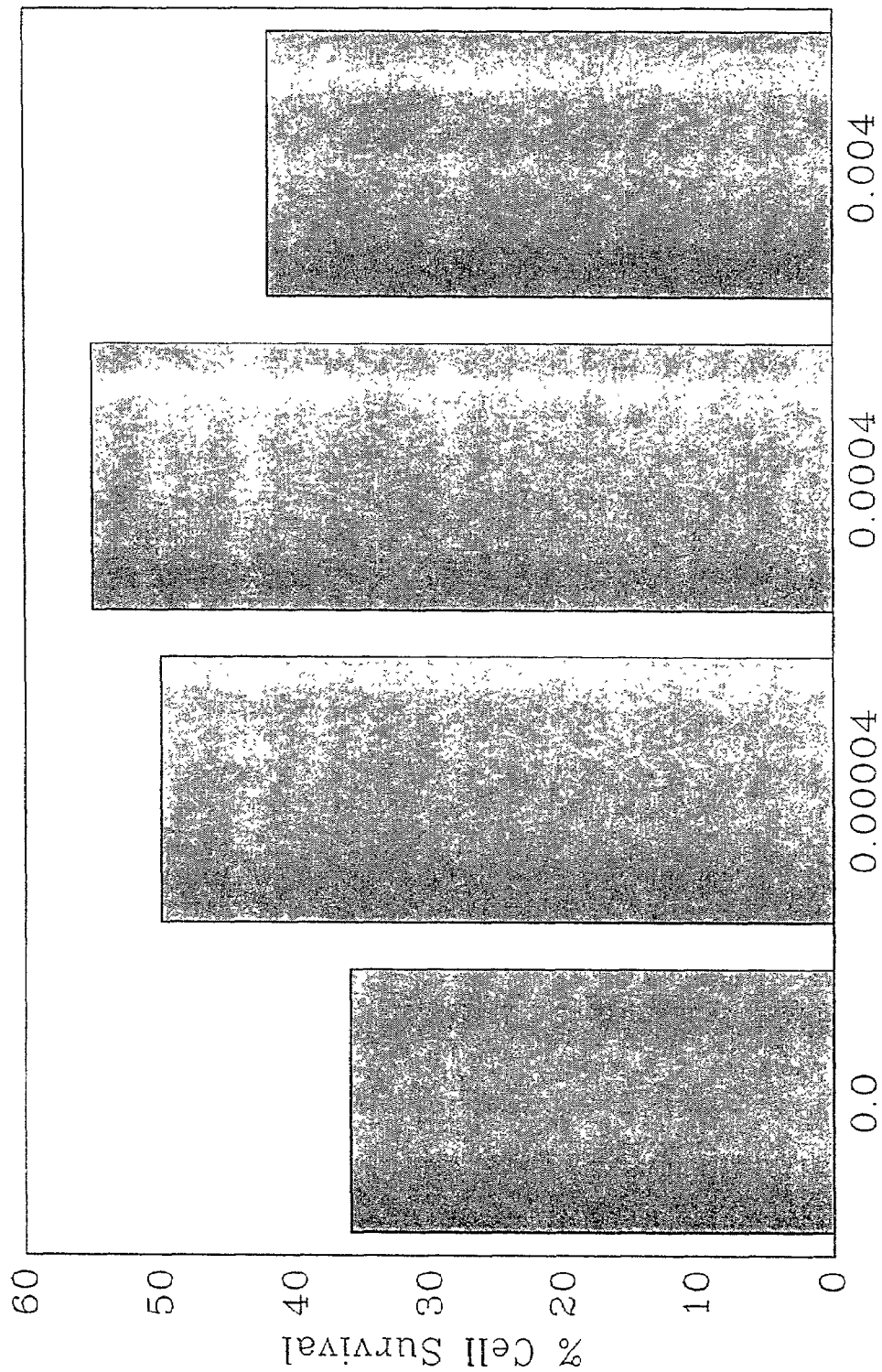
Figure 14A:
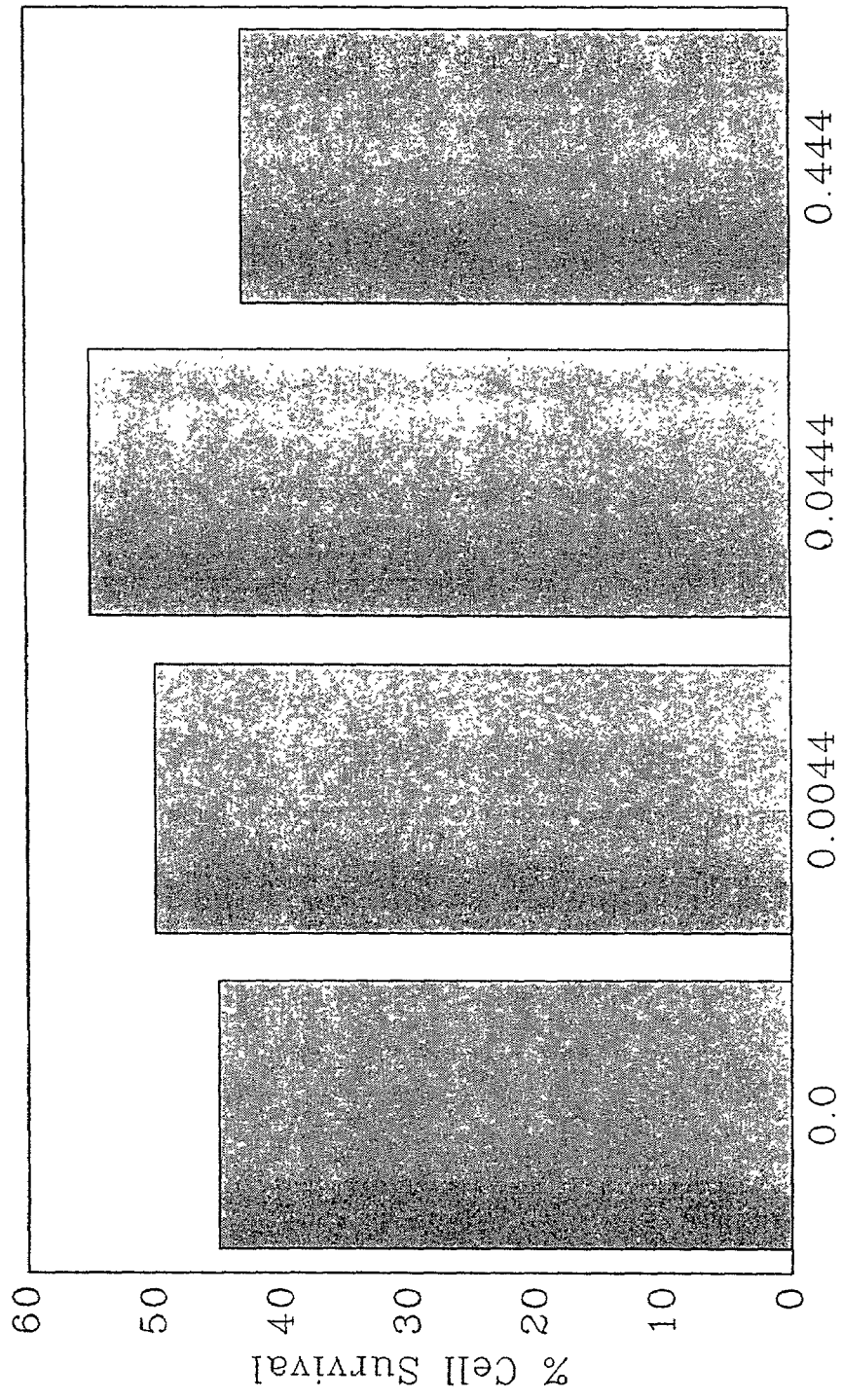
Figure 14B:
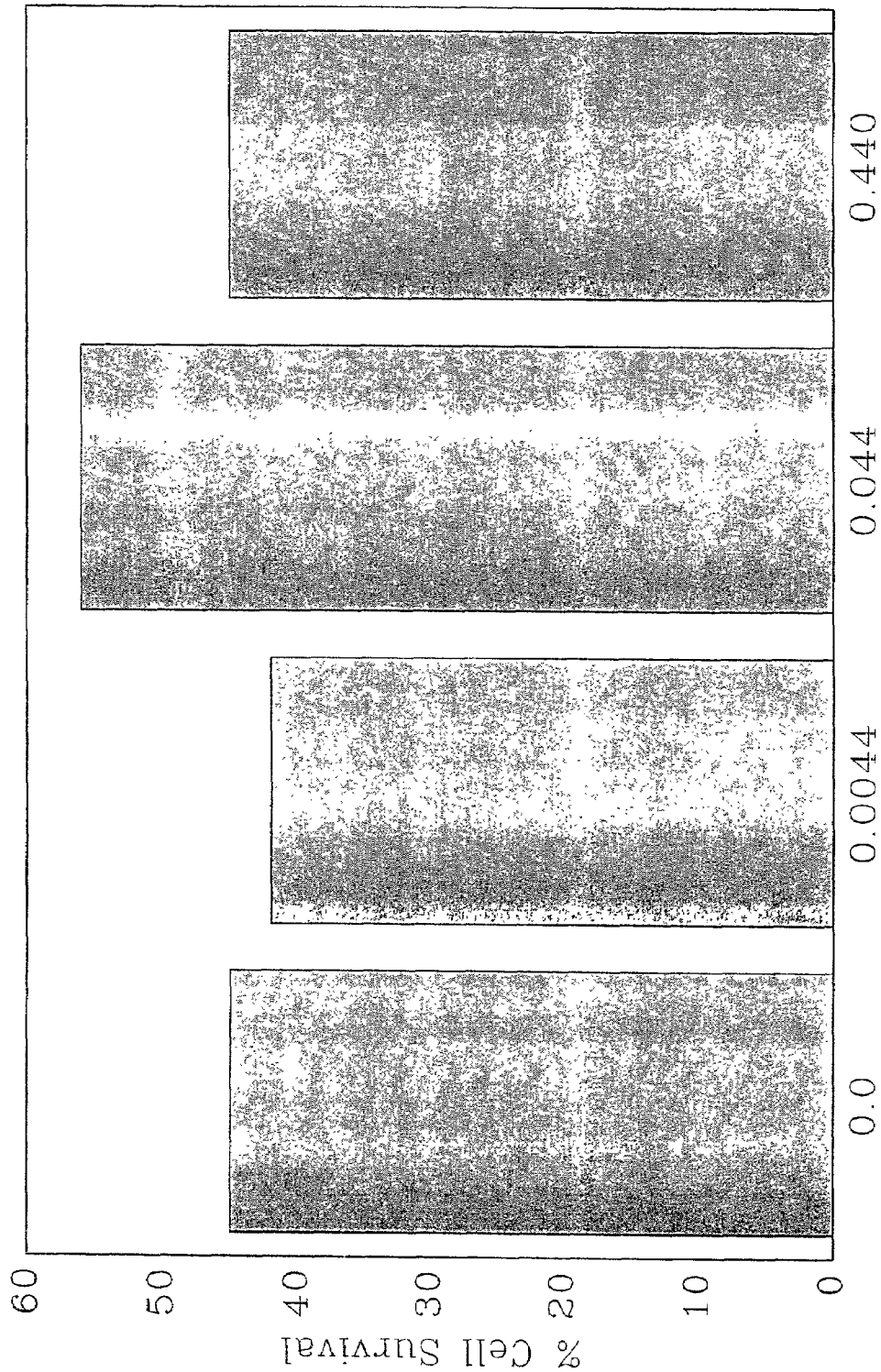
Figure 14C:
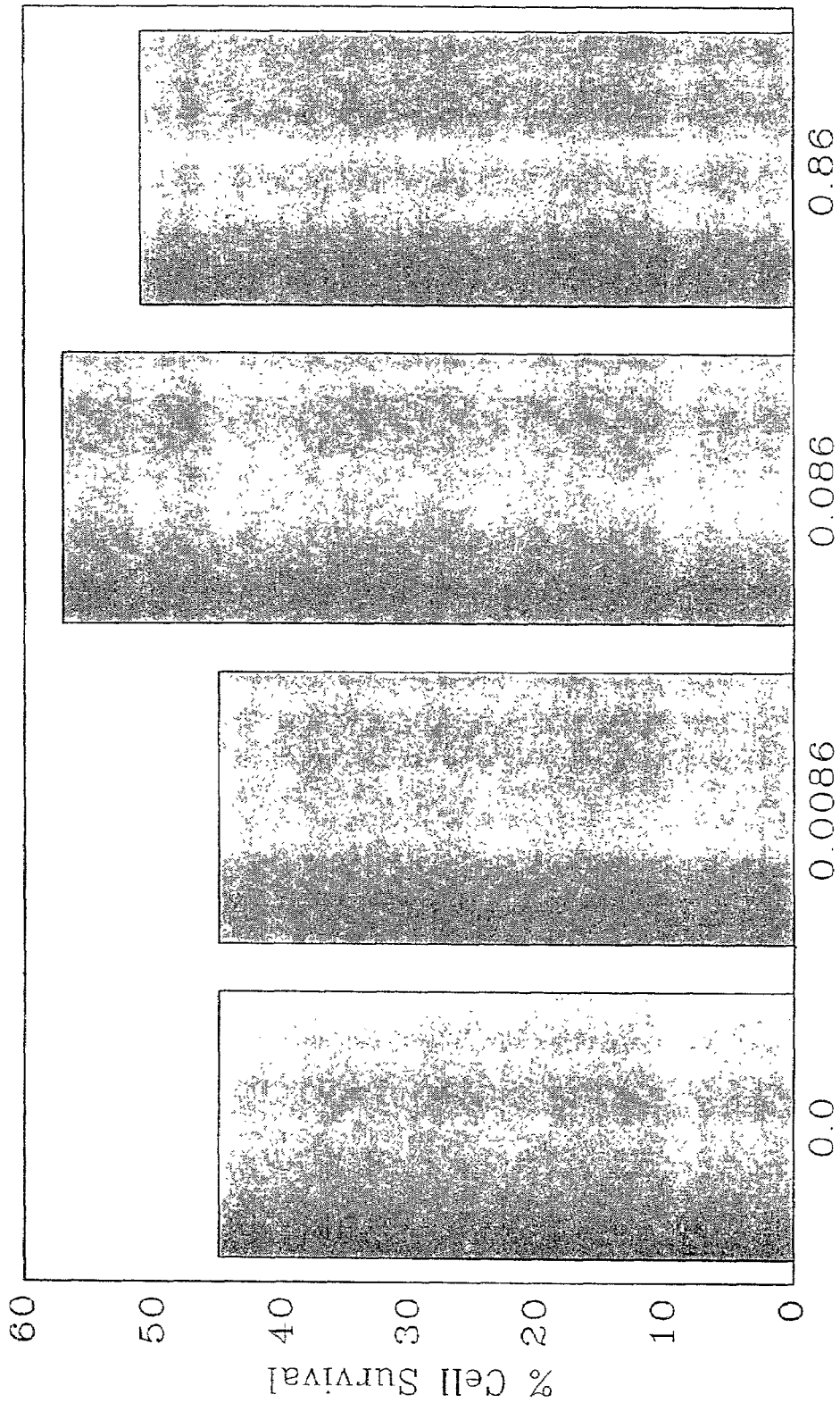
Figure 14D:
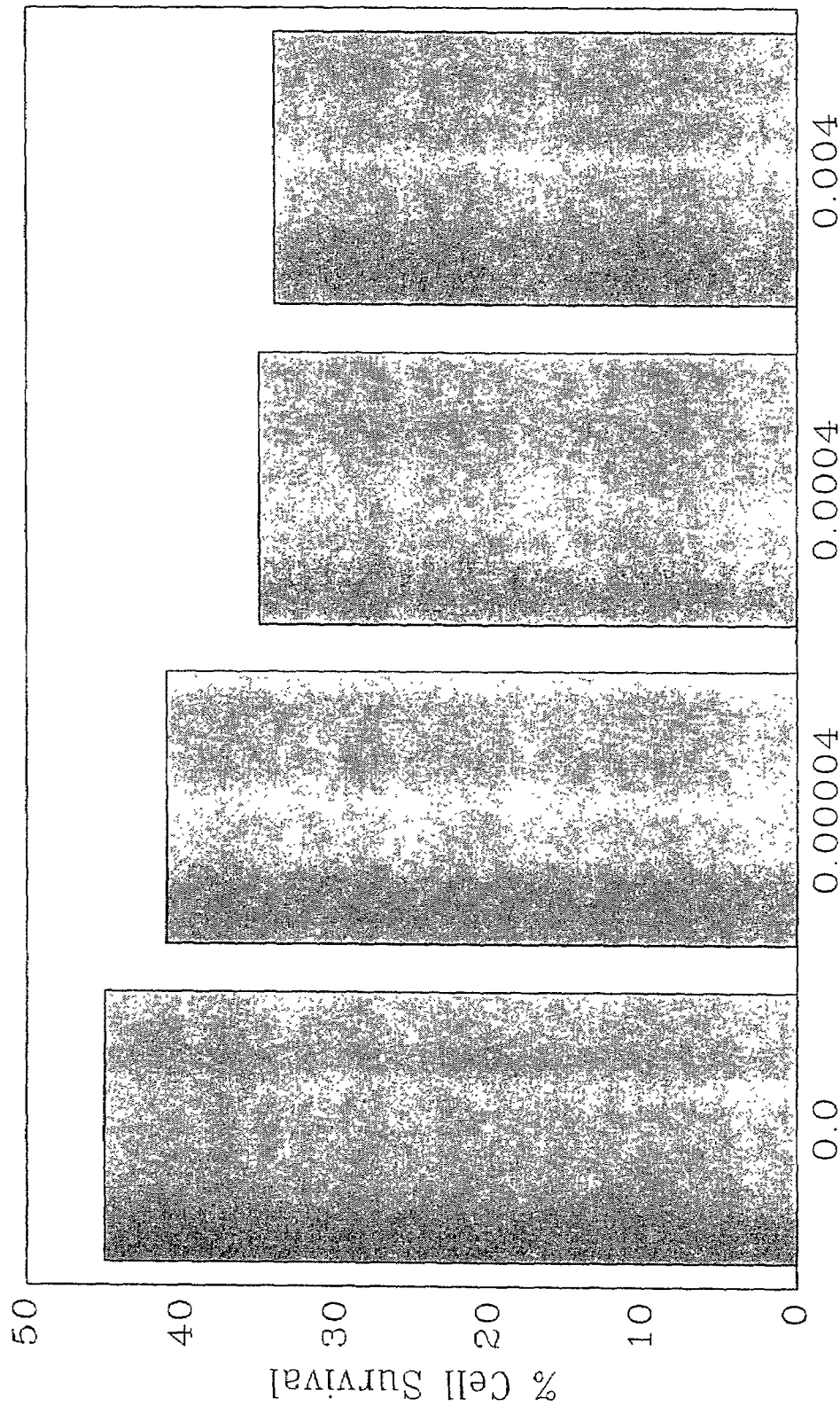
Figure 14E:
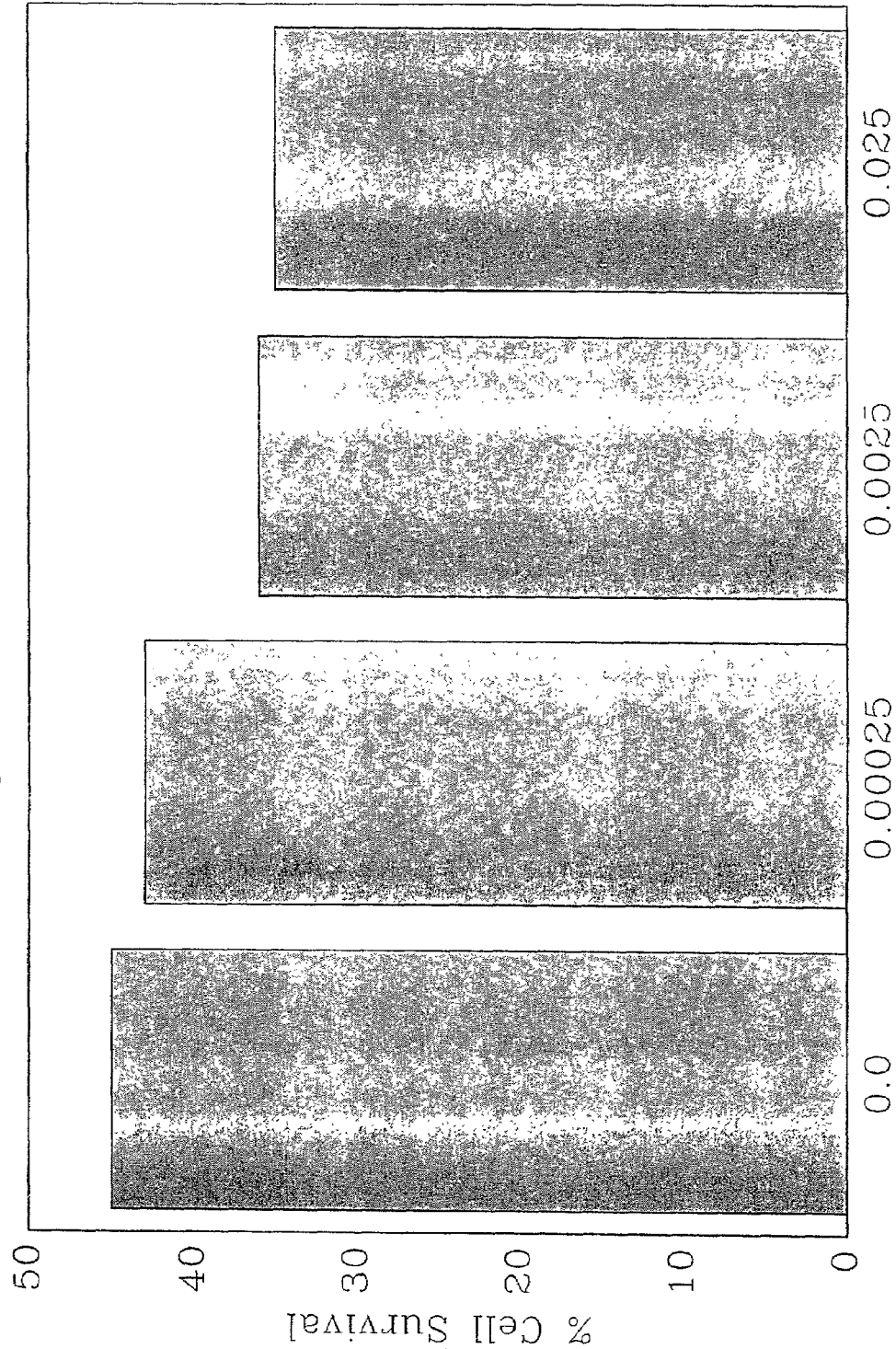
Figure 15A:
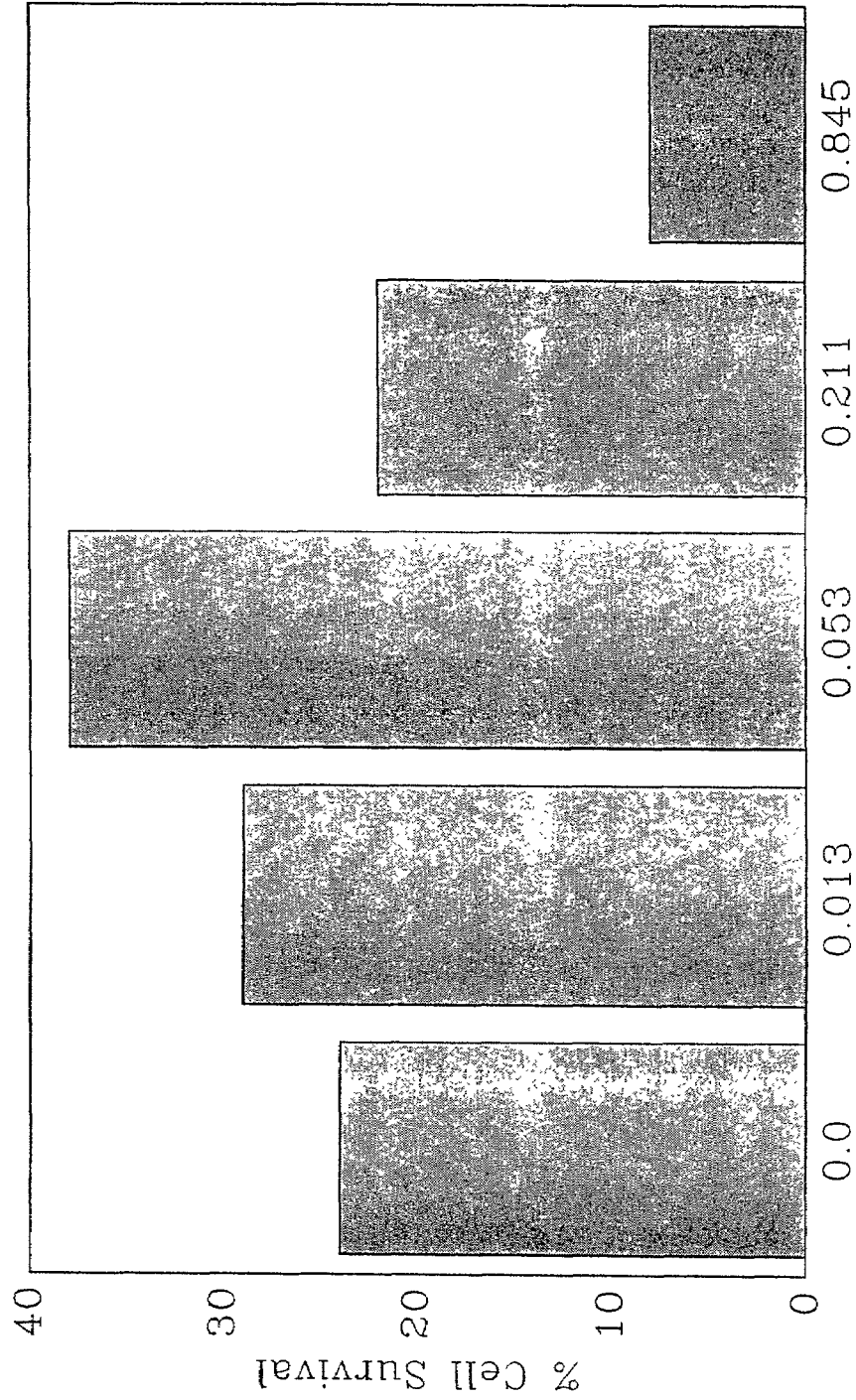
Figure 15B:
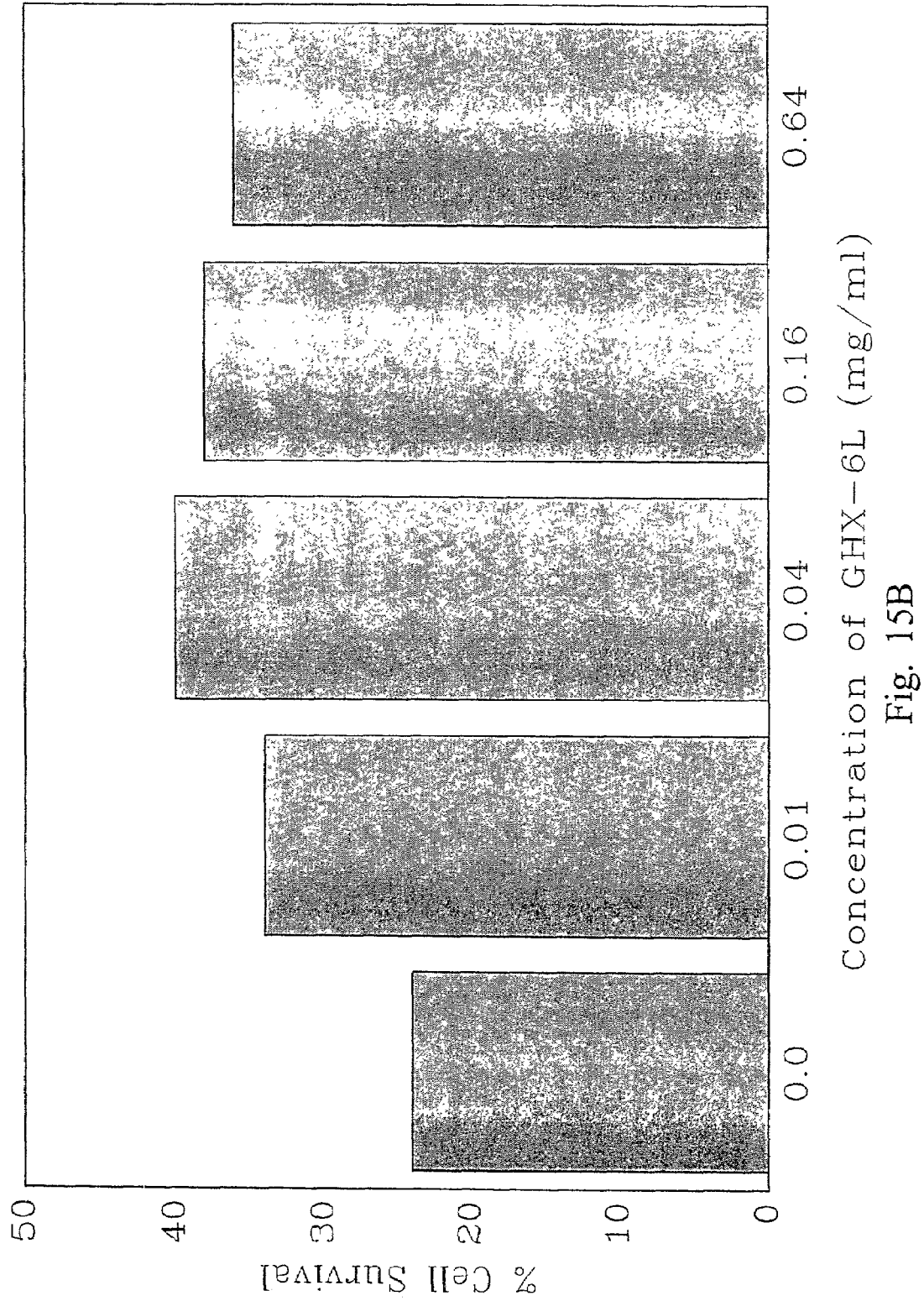
Figure 15C:
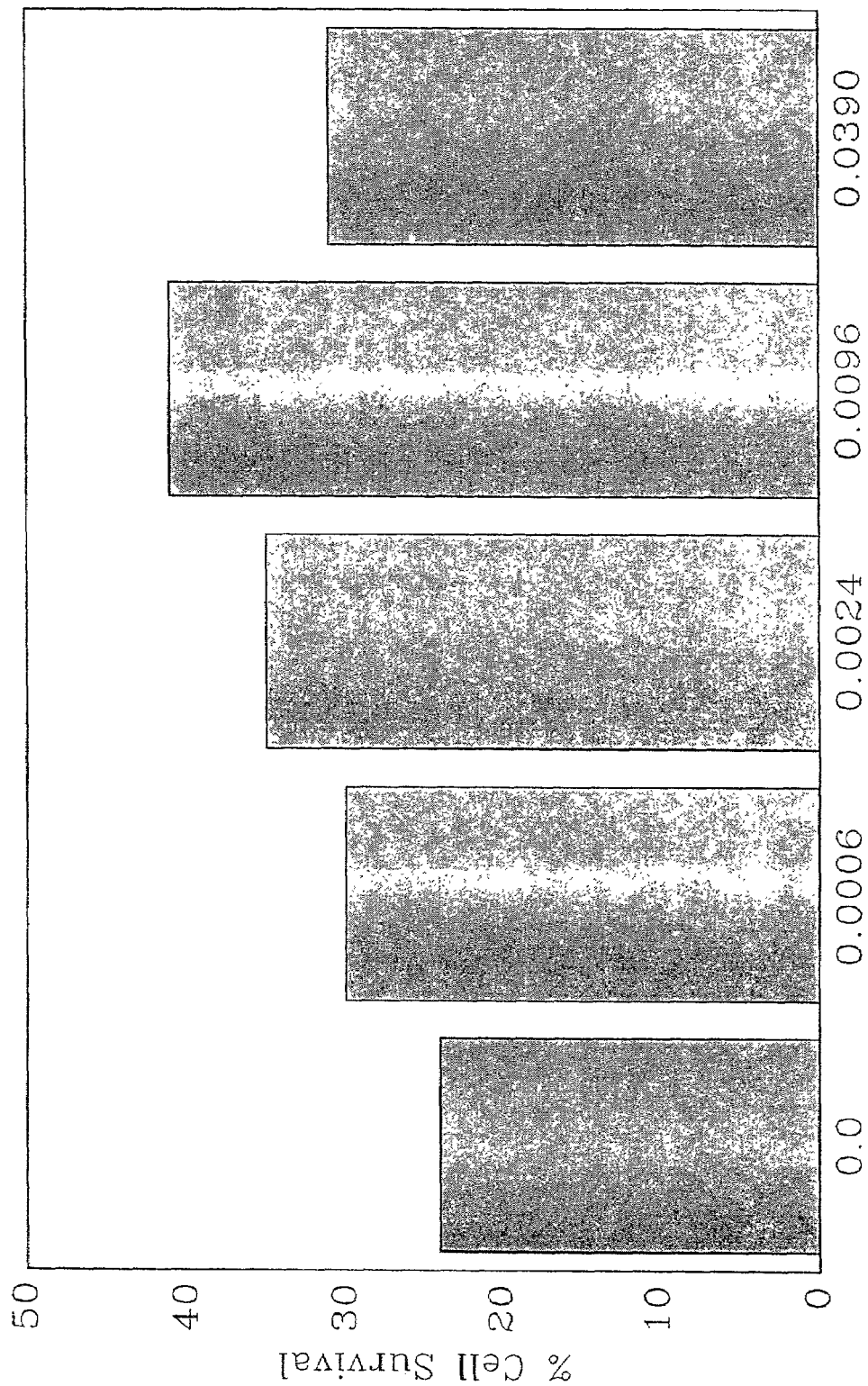
Figure 15D:
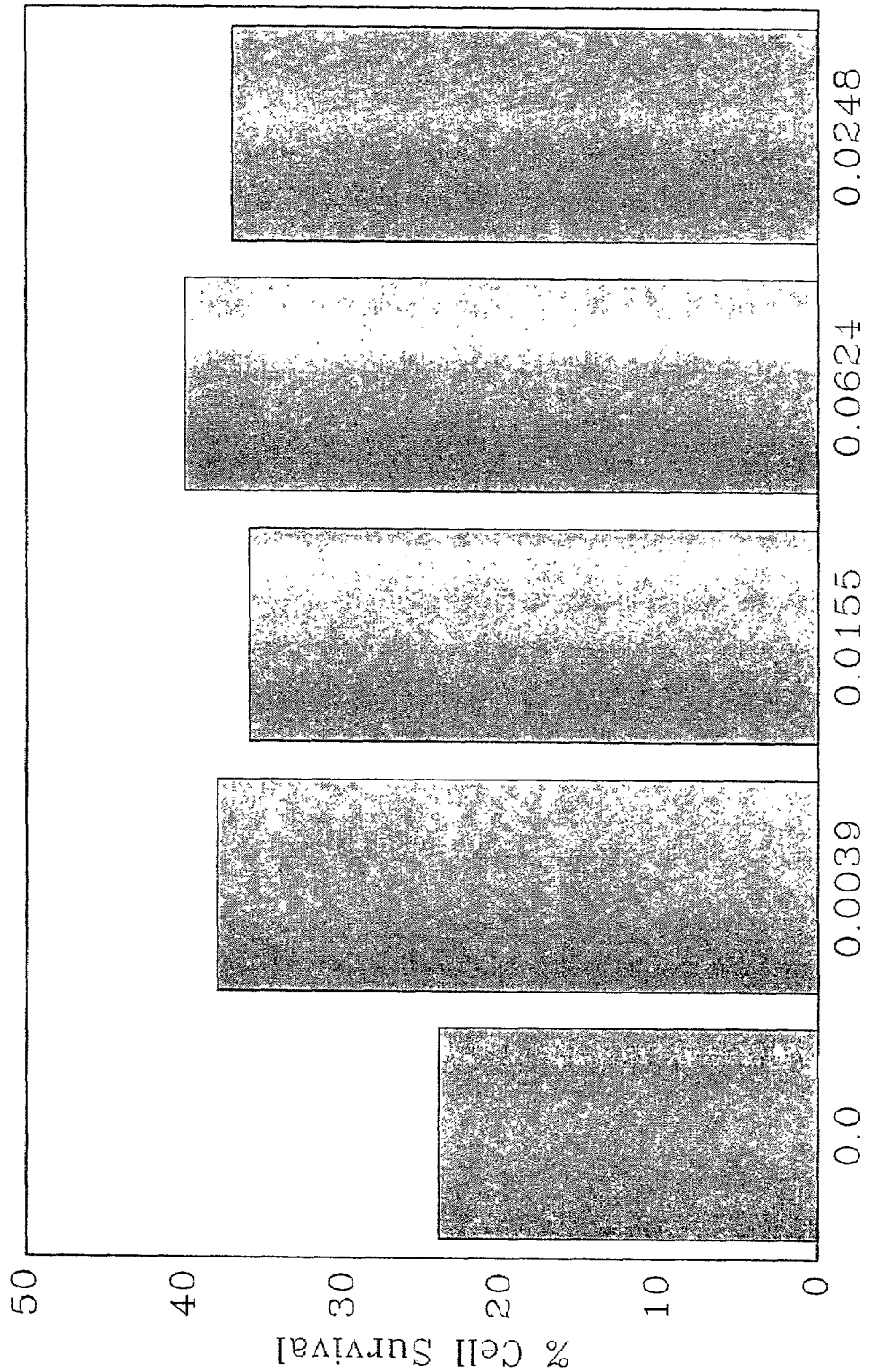

The results of plant extract toxicity controls incorporated in examples 4 and 5 are hereby analysed in FIGS. 9 and 10. Uninfected cells were exposed to various concentrations of plant extracts similar to what is described in 4. After 5 days of incubation, tetrazolium-based colorimetry was done on the cultures. The optical density (O.D.) values from treated wells without cells were subtracted from treated wells with cells. The resultant values were then expressed as percentages of control untreated wells with cells. These values were then plotted against the concentrations of the plant extracts (FIGS. 9 and 10).

The EC50 values of the plant extracts against HIV-1 and 2 determined in examples 4 and 5, did not cause any adverse effects to the cells tested. The EC90 values caused minimal or no toxicity to the cells. From FIGS. 9 and 10, the 50% cytotoxic concentrations (CC50) were determined and used in the calculation of antiviral indices in tables 4 and 5 which show that the plant extracts are indeed selective anti-HIV agents.

11. Ex vivo Effects of Plant Extracts on Peripheral Blood Mononuclear Cells (PBMCs).

Accelerated death of PBMCs in HIV infected patients, particularly the CD4+ fraction, has been shown to be due to increased programmed cell death or apoptosis (Oyaizu et al, 1993). In vitro culturing of PBMCs enhances this phenomenon. Thus the ability of a drug or plant extract to slow down the accelerated death of cultured PBMCs may reflect their potentials in maintaining steady PBMC levels in HIV infected patients.

FIGS. 11, 12, 13, 14, and 15 show the effects of the plant extracts on culture induced cell death in the PBMCs of one healthy person and four AIDS patients. For comparison, ddCyd and ddIno were included in the tests. ddCyd, ddIno, and GHX-7L showed no toxicity towards PBMCs from the healthy person at all the concentrations tested. Plants GHX-2, GHX-6, and GHX-7 slowed down the accelerated culture induced death of PBMCs from all four AIDS patients at noncytotoxic concentrations. Likewise, ddCyd and ddIno were effective in these patients except one AIDS patient where the two drugs failed to slow down the accelerated culture induced death of the PBMCs. The plant extracts therefore have the potential of slowing the accelerated death of PBMCs in HIV infected patients and thus restore immunocompetence.

12. Effects of Plant Extracts on Bacteria Growth.

In addition to viral opportunistic infections in the immunosuppressed, bacterial opportunistic infections, especially tuberculosis and *Salmonella bacteremia*, have become major medical problems in the immunosuppressed states like AIDS. In the absence of facilities to test the plant extracts against *Mycobacterium tuberculosis* in vitro, the extracts were tested against *Staphylococcus aureus, Salmonella typhimurium, Klebsiella pneumonia*, and an *Edwardsiella* species.

Various inoculi of bacteria were cultured in maintainance minimal essential medium without antibiotics in the presence of various concentrations of plant extracts. After 18 hrs of incubation, the tetrazolium-based colorimetry was done on the cultures. The O.D. readings from treated wells without bacteria were subtracted from O.D. readings from treated wells with bacteria. The results were expressed as percentages of control untreated wells with bacteria. These values were then plotted against the concentrations of plant extracts and the 50% inhibition concentrations determined.

Plant extracts GHX-8, X-20, and X-26 were invariably inhibitory to the bacteria tested (Table 11, 12, 13, and 14). Other plant extracts had minimal activities against bacteria. The ability of a drug to inhibit HIV and some opportunistic viruses and bacteria is an added advantage in the treatment of AIDS. Drugs that act on only opportunistic viruses and bacteria would also be beneficial in combination therapies for AIDS.

13. Rationalized Combination Therapy Against HIV Infections.

Based on the foregoing examples, it would seem appropriate to combine extracts from different plants for maximum effects. Plants GHX-6 and GHX-27 (hereby designated group A) are most effective against HIV when treatment is started early after infection. Highly significant activities against HIV are however obtained for plants GHX-2 and GHX-26 (hereby designated group B) even in chronically infected cells. In addition, plant GHX-27 (hereby desinated group C) selectively kills HIV/Molt4 chronically infected cells at concentrations with no effects on uninfected Molt4 cells. The different modes of action of the plants should allow for combinations with enhanced activities. Thus a combination of drugs selected from groups A (inhibitors of early viral events), B (inhibitors of late viral events), and C (a killer of HIV infected cells), would be ideal for treating HIV infections.

TABLE 1

Plants with anti-infective activities.

| Plant | | Antiviral* | Antibacterial* |
|---|---|---|---|
| GHX-2 | (*Ocimum gratissimum*) | + | + |
| GHX-4 | (*Sanseviera liberica*) | + | − |
| GHX-6 | (*Ficus polita*) | + | − |
| GHX-7 | (*Clausena anisata*) | + | − |
| GHX-8 | (*Rauwolfia vomitoria*) | − | + |
| GHX-20 | (*Combretum aphanopetalum*) | + | + |
| GHX-26 | (*Alchornea cordifolia*) | + | + |
| GHX-27 | (*Elaeophorbia drupifera*) | + | + |

*See tables 2 to 14 for specific viruses and bacteria used in tests.

TABLE 2

Effects of plant extracts on virus CPE production in Vero cells. Amount of virus used was 100 TCID50/well and treatment was started 2 hrs after virus adsorption.

| Virus | GHX-2L | GHX-2R | GHX-4R | GHX-6L | GHX-7L | GHX-20L | GHX-26F |
|---|---|---|---|---|---|---|---|
| | EC50 (mg/ml) of plant aqueous extracts | | | | | | |
| HSV-2,A | 0.70 | 0.48 | 1.50 | 0.50 | 1.80 | 0.30 | 0.30 |
| HSV-1,G | 0.26 | 0.24 | 0.76 | 0.30 | NT | NT | NT |
| | EC100 (mg/ml) of plant aqueous extracts | | | | | | |
| HSV-2,A | 1.60 | 1.20 | 2.50 | 1.20 | 3.00 | 0.80 | 1.20 |
| USV-1,G | 1.10 | 0.60 | 2.00 | 0.80 | NT | NT | NT |
| | EC50 (mg/ml) of plant aqueous extracts | | | | | | |
| Polio, I | 1.20 | 0.90 | 2.04 | 1.10 | | | |
| II | 0.23 | <0.23 | <<0.05 | 0.30 | | | |
| III | NE | NE | 0.075 | 0.90 | | | |
| Measles | 0.85 | NE | 5.70 | NE | | | |
| Yellow Fever | 0.60 | 0.27 | 2.00 | NE | | | |

NT - Not tested
NE - Not effective

TABLE 3

Effects of 90% methanol extracts on HSV-2 strain A CPE and virus yield in Vero cells. 50 TCID50/ml of virus per well used. Drug treatment was started 2 hrs after virus adsorption.

| Concentration (mg/ml) | CPE (%) | Virus yield ($\log_{10} TCID_{50}$/ml) |
|---|---|---|
| A. Plant extract GHX-20L | | |
| 0.000 | 100 | 6.5 |
| 0.088 | 100 | 6.5 |
| 0.175 | 50 | 4.5 |
| 0.350 | 0 | 2.0 |
| 0.700 | 0 | 0.0 |
| 1.400 | 0 | <0.0 |
| B. Plant extract GHX-6L | | |
| 0.000 | 100 | 6.0 |
| 0.074 | 100 | 6.0 |
| 0.148 | 80 | 5.0 |
| 0.295 | 40 | 3.5 |
| 0.590 | 0 | 1.5 |
| 1.180 | 0 | 0.0 |

TABLE 4

Effects of aqueous extracts of plants against HIV-1 strain HTLVIIIB in Molt4 clone 8 infected at a multiplicity of infection of 0.00357. Drug treatment was started at 40 mins after virus adsorption.

| Plant extract | EC50 (mg/ml) | CC50 (mg/ml) | AI |
|---|---|---|---|
| GHX-2L | 0.01 | 1.1 | 110.0 |
| GHX-6L | 0.03 | 1.3 | 43.3 |
| GHX-7L | 0.70 | >>1.4* | >>2.0 |
| GHX-26S | 0.02 | >1.8* | >90.0 |
| GHX-26F | 0.01 | 0.18 | 18.0 |
| GHX-26S + F | 0.01 | 0.71 | 71.0 |
| GHX-27L | 0.014 | 0.45 | 32.0 |

*Highest concentration tested.
EC50 - Fifty percent effective concentration.
CC50 - Fifty percent cytotoxic concentration.
AI - Antiviral index defined as CC50/EC50

TABLE 5

Effects of plant extracts against HIV-1 strains HTLVIIIB and GH3 in M8166 cells infected at a multiplicity of infection of 0.00375. Drug treatment was started after 2 hrs of virus adsorption.

| | Strain HTLVIIIB | | | Strain GH3 | | |
|---|---|---|---|---|---|---|
| | EC50 | CC50 | AI | EC50 | CC50 | AI |
| Plant extract# | (mg/ml) | | | (mg/ml) | | |
| GHX-2L | 0.07 | 1.00 | 14.3 | 0.06 | 1.00 | 16.7 |
| GHX-6L | 0.03 | 0.99 | 33.0 | 0.045 | 0.99 | 22.2 |
| GHX-7L | 0.93 | >1.40* | >1.5 | 0.20 | >1.40 | >7.0 |

*Highest concentration tested.

TABLE 6

Effects of aqueous extracts of plants against HIV-2 strain GH1 in Molt 4 clone 8 cell line. Multiplicity of infection was 0.018 and treatment was started after 40 mins of virus adsorption.

| Plant extract | EC50 (mg/ml) | EC90 (mg/ml) |
|---|---|---|
| GHX-2L | 0.075 | 0.21 |
| GHX-2R | 0.065 | 0.15 |
| GHX-6L | <0.005* | 0.17 |
| GHX-7L | 0.110 | 0.40 |
| GHX-27L | <0.005* | 0.02 |
| AZT | <0.0000003* | 0.0003 |

*Lowest concentration tested

TABLE 7

Effects of plant extracts against HIV-2 strain GH1 in Molt 4 clone 8 cells. Multiplicity of infection used was 0.018 and treatment was started 2 hrs after virus adsorption.

| Plant extracts# | EC50 (mg/ml) | EC90 (mg/ml) |
|---|---|---|
| GHX-2L | 0.13 | 0.32 |
| GHX-2R | 0.08 | 0.27 |
| GHX-6L | 0.025 | 0.40 |
| GHX-7L | 0.12 | 1.25 |
| AZT | 0.000001 | NE |

TABLE 8

Effects of aqueous extract of plant GHX-6L on HIV-1 strain HTLVIIIB virus yield in Molt 4 clone 8 cells when treatment was started 40 mins after virus adsorption. Multiplicity of infection was 0.00375.

| | Titre ($\times 10^3$ $TCID_{50}$/ml) * | | |
|---|---|---|---|
| Concentration (mg/ml) | 24 hrs | 48 hrs | 72 hrs |
| 0.00 | 0.060 | 3.10 | 39.00 |
| 0.106 | 0.00 | 0.32 | 2.00 |
| 0.211 | 0.00 | 0.20 | 1.00 |
| 0.423 | 0.00 | 0.14 | 0.64 |
| 0.845 | 0.00 | 0.00 | 0.16 |

* Supernatants were collected at 24, 48, and 72 hrs post virus infection and titrated.

TABLE 9

Effects of aqueous extracts of plants on HIV-1 strain GH1 virus yield in Molt 4 clone 8 when treatment was started after 40 mins of virus adsorption. Multiplicity of infection was 0.009.

| | Concentration (mg/ml) | *Titre ($\times 10^3$ $TCID_{50}$/ml) |
|---|---|---|
| A. GHX-2L | 0.00 | 10.40 |
| | 0.066 | 1.26 |
| | 0.132 | 0.61 |
| | 0.264 | 0.57 |
| | 0.528 | 0.12 |
| B. GHX-6L | 0.00 | 10.40 |
| | 0.053 | 0.82 |
| | 0.106 | 0.78 |
| | 0.213 | 0.61 |
| | 0.425 | 0.00 |

*Supernatants were collected at 120 hrs post virus infection and titrated.

TABLE 10

Effects of plant extracts on HIV-1 reverse transcriptase activity.

| Drug | Concentration (mg/ml) | CPM# |
|---|---|---|
| Negative Contol | 0.0 | 4316.6 + 535.0 |
| Positive Control | 0.0 | 261020.7 + 37929.3 |
| Blank | 0.0 | 518.2 + 196.6 |
| GHX-2L | 0.013 | 27623.3 + 5385.3 |
|  | 0.038 | 11289.0 + 10239.8 |
|  | 0.114 | 4871.2 + 917.1 |
|  | 0.342 | 2503.2 + 686.7 |
| GHX-6L | 0.004 | 110301.9 + 113586.0 |
|  | 0.011 | 56957.4 + 17907.0 |
|  | 0.033 | 13551.0 + 5694.5 |
|  | 0.100 | 3105.5 + 137.5 |
|  | 0.299 | 3218.7 + 2420.0 |
| GHX-26F | 0.005 | 118624.9 + 8628.4 |
|  | 0.010 | 50799.0 + 41135.7 |
|  | 0.020 | 11278.3 + 1598.8 |
|  | 0.041 | 5796.2 + 416.6 |
|  | 0.081 | 5455.2 + 144.0 |
| GHX-27L | 0.008 | 265405.8 + 155310.8 |
|  | 0.017 | 144706.5 + 7651.4 |
|  | 0.033 | 111681.5 + 47123.6 |
|  | 0.067 | 59043.4 + 9510.3 |
|  | 0.133 | 51252.6 + 4209.2 |

CPM - Counts per minute

TABLE 11

Effects of plant extracts, sodium penicillin G, and streptomicin sulfate on the growth of *Staphylococcus aureus*.

| Plant extract/drug | Inoculum (CID50) | EC50 (mg/ml) | EC90 (mg/ml) |
|---|---|---|---|
| GHX-8R | $10^1$ | 0.114 | 0.455–0.91* |
|  | $10^2$ | 0.228 | NE |
|  | $10^3$ | 0.228–0.445 | NE |
| GHX-20L | $10^1$ | 0.075 | 0.149 |
|  | $10^2$ | 0.075–0.149 | 0.149–0.298 |
|  | $10^3$ | 0.149–0.298 | 0.149–0.298 |
| GHX-26F | $10^1$ | 0.0038 | 0.061 |
|  | $10^2$ | 0.0077 | 0.124 |
|  | $10^3$ | 0.124 | 0.124–0.248 |
| GHX-27L | $10^1$ | 0.520* | NE |
|  | $10^2$ | 0.520 | NE |
|  | $10^3$ | 0.520 | NE |
| Penicillin G | $10^1$ | <0.0005 | <0.0005 |
|  | $10^2$ | <0.0005 | <0.0005 |
|  | $10^3$ | 0.002 | 0.002–0.004 |
| Streptomycin sulfate | $10^1$ | <0.0004 | <0.0004 |
|  | $10^2$ | <0.0004 | <0.0004 |
|  | $10^3$ | <0.0004 | <0.0004 |

*Highest concentration tested.
NE - not effective
CID50 - Culture infectious dose of 50% of the wells.

TABLE 12

Effects of plant extracts, sodium penicillin G, and streptomicin sulfate on the growth of *Salmonella typhimurium*.

| Plant extract/drug | Inoculum (CID50) | EC50 (mg/ml) | EC90 (mg/ml) |
|---|---|---|---|
| GHX-20L | $10^1$ | 0.149–0.298* | 0.149–0.298 |
|  | $10^2$ | NE |  |
|  | $10^3$ | NE |  |
| GHX-26F | $10^1$ | 0.03–0.06 | 0.124–0.248 |
|  | $10^2$ | 0.124 | 0.248 |
|  | $10^3$ | 0.248* | NE |
| Penicillin G | $10^1$ | 0.157–0.314 | 0.157–0.314* |
|  | $10^2$ | NE |  |
|  | $10^3$ | NE |  |
| Streptomycin sulfate | $10^1$ | 0.016–0.032 | 0.016–0.032 |
|  | $10^2$ | 0.016–0.032 | 0.016–0.032 |
|  | $10^3$ | 0.016–0.032 | 0.016–0.032 |

*Highest concentration tested.
NE - not effective
CID50 - Culture infectious dose of 50% of the wells.

TABLE 13

Effects of plant extracts, sodium penicillin G, and streptomicin sulfate on the growth of *Klebsiella pneumoniae*.

| Plant extract/drug | Inoculum (CID50) | EC50 (mg/ml) | EC90 (mg/ml) |
|---|---|---|---|
| GHX-20L | $10^2$ | 0.040 | 0.085 |
| GHX-26F | $10^2$ | 0.124–0.248 | 0.124–0.248 |
| Penicillin G | $10^2$ | 0.075 | 0.13 |
| Streptomicin sulfate | $10^2$ | <0.001 | <0.001 |

CID50-Culture infectious dose of 50% of the wells.

TABLE 14

Effects of plant extracts, sodium penicillin G, and streptomicin sulfate on the growth of *Edwardsiella* species isolated as a tissue culture contaminant.

| Plant extract/drug | Inoculum (CID50) | EC50 (mg/ml) | EC90 (mg/ml) |
|---|---|---|---|
| GHX-2L | $10^1$ | 0.047-0.095 | 0.095–0.189 |
|  | $10^2$ | 0.095 | 0.095–0.189 |
|  | $10^3$ | 0.189–0.379 | 0.189–0.379 |
| GHX-8R | $10^1$ | 0.036 | 0.073 |
|  | $10^2$ | 0.147 | 0.587 |
|  | $10^3$ | 0.587–1.300 | 1.300 |
| GHX-20L | $10^1$ | 0.003 | 0.012 |
|  | $10^2$ | 0.006 | 0.012 |
|  | $10^3$ | 0.006–0.012 | 0.012–0.024 |
| Penicillin G | $10^1$ | 0.196–0.392 | 0.392 |
|  | $10^2$ | 0.196–0.392 | 0.392–0.784 |
|  | $10^3$ | >0.784* | >0.784 |
| Streptomycin sulfate | $10^1$ | 0.063 | 0.063–0.125 |
|  | $10^2$ | 0.063 | 0.500 |
|  | $10^3$ | >0.500* | >0.500 |

*Highest concentration tested.
CID50-Culture infectious dose of 50% of the wells.

REFERENCES

1. Sarngadharan et al, 1994. Science; 224:506–508.
2. Wong-Staal F & Gallo R C, 1985. Nature; 317:395–403.
3. Egbert et al, 1980. Ann. Int. Med.; 93:664–670.
4. Mintz et al, 1983. Ann. Int. Med.; 99:326–329.
5. Frank D & Raicht R F, 1984. Amer. J. Gastro.; 79:201–205.
6. Lerner C W & Tapper M L, 1984. Medicine (Baltimore); 63:155–164.
7. Meiselman et al,1985. Gastroenterology; 88:171–175.
8. De Clercq E, 1986. J. Med. Chem.; 29:1561–1569.
9. Tuazon C U & Labriola A M, 1987. Drugs; 33:66–84.
10. Sandstrom E G & Kapln J C, 1987. Drugs; 34:372–390.
11. Eriksson et al, 1989. Antimicrob Agents Chemother.; 33:1729–1734.

12. Donovan et al, 1991. J. Acq. Imm. Def. Synd.; 4:765–769.
13. Dickover et al, 1992. J. Acq. Imm. Def. Synd.; 5:31–36.
14. Meng et al, 1992. Ann. Int. Med.; 166:13–20.
15. Hudson J B & Towers G H N, 1991. Pharmac. Ther.; 49:181–222.
16. Hudson et al, 1991. Antiviral Res.; 15:101–112.
17. Eriksson E & Oberg B, 1979. Antimicrob. Agents Chemother.; 15:758–762.
18. Hovi T, 1980. Med. Biol.; 58:5–7.
19. Lai et al, 1990. AIDS Res. Hum. Retro.; 6:205–217.
20. Takayama et al, 1991. AIDS Res. Hum. Retro.; 7:349–357.
21. Balzarini et al, 1992. Antiviral Res.; 18:191–207.
22. Skinner G R & Ezra M., 1993. Int. Patent Public. No. WO 93/11779.
23. Ho D D & Li X S, 1991. Int. Patent Public. No. WO 91/19507.
24. Ayisi et al, 1980. Antimicrob. Agents Chemother.; 17:558–566.
25. Ayisi et al, 1983. Antiviral Res.; 3:161–174.
26. Ayisi et al, 1985. Antiviral Res.; 5:13–27.
27. Ayisi et al, 1991. J. Virol. Methods; 33:335–344.

The invention claimed is:

1. A method comprising: contacting a virus-infected cell with an extract from *Ocimum gratissimum* in an amount effective to inhibit cytopathic effects of the virus in the cell.

2. The method according to claim 1 wherein the virus is human immunodeficieney virus (WV), herpes simplex virus (HSV), human cytomegalovirus (HCMV), poliovirus (PV), measles virus (MV) or yellow fever virus (YMY).

3. The method according to claim 2, wherein the virus is HIV.

4. The method according to claim 2, wherein the virus is HIV-1, HCMV, HSV-1 or HSV-2.

* * * * *

UNITED STATES PATENT AND TRADEMARK OFFICE
CERTIFICATE OF CORRECTION

PATENT NO.       : 7,220,437 B2
APPLICATION NO.  : 09/978593
DATED            : May 22, 2007
INVENTOR(S)      : Nana K. Ayisi It is certified that error appears in the above-identified patent and that said Letters Patent is hereby corrected as shown below:

Column 16, Claim 2, line 12, "(WV)" should be corrected to read -- (HIV) --

Signed and Sealed this

Sixth Day of November, 2007

JON W. DUDAS
*Director of the United States Patent and Trademark Office*